(12) United States Patent
van der Burg

(10) Patent No.: US 11,491,272 B2
(45) Date of Patent: Nov. 8, 2022

(54) ENDOVASCULAR IMPLANTS AND DEVICES AND METHODS FOR ACCURATE PLACEMENT

(71) Applicant: Venova Medical, Inc., Los Gatos, CA (US)

(72) Inventor: Erik van der Burg, Los Gatos, CA (US)

(73) Assignee: Venova Medical, Inc., Los Gatos, CA (US)

( * ) Notice: Subject to any disclaimer, the term of this patent is extended or adjusted under 35 U.S.C. 154(b) by 0 days.

(21) Appl. No.: 17/512,464

(22) Filed: Oct. 27, 2021

(65) Prior Publication Data

US 2022/0143289 A1 May 12, 2022

Related U.S. Application Data

(60) Provisional application No. 63/245,114, filed on Sep. 16, 2021, provisional application No. 63/111,548, filed on Nov. 9, 2020.

(51) Int. Cl.
*A61M 1/36* (2006.01)
*A61F 2/06* (2013.01)
(Continued)

(52) U.S. Cl.
CPC ........... *A61M 1/3655* (2013.01); *A61F 2/966* (2013.01); *A61M 1/3661* (2014.02); *A61M 27/002* (2013.01); *A61F 2002/061* (2013.01)

(58) Field of Classification Search
CPC .............. A61M 1/3655; A61M 1/3661; A61M 27/002; A61F 2/966; A61F 2002/061;
(Continued)

(56) References Cited

U.S. PATENT DOCUMENTS 5,755,778 A 5/1998 Kleshinski
5,830,222 A 11/1998 Makower
(Continued)

FOREIGN PATENT DOCUMENTS

WO WO 2016/131822 A1 8/2016
WO WO 2018/236835 A1 12/2018
WO WO-2021087294 A1 * 5/2021 ............. A61B 17/11

OTHER PUBLICATIONS

PCT Invitation to Pay Additional Fees in PCT/US2021/072064 dated Feb. 11, 2022.
(Continued)

*Primary Examiner* — Philip R Wiest
*Assistant Examiner* — Alessandro R Del Priore
(74) *Attorney, Agent, or Firm* — Knobbe, Martens, Olson & Bear, LLP

(57) ABSTRACT

Various systems, devices, and methods for endovascular implants and placement thereof are disclosed. The implants include a proximal implant segment, a distal implant segment, connector struts connecting the proximal implant segment to the distal implant segment, and a side opening between the proximal implant segment and the distal implant segment. The implants can be used to create an arteriovenous fistula or connect one vessel of the body to another by placement of the proximal implant segment and the distal implant segment within the vessels to be connected. The implants can include one or more anchors for securing the implant in place with respect to the vessels of the body it is connecting. The implants can also include a continuous strut or ring at a distal edge of the proximal implant segment. Also disclosed are methods for percutaneous placement of the implants, and a device for percutaneous delivery.

30 Claims, 47 Drawing Sheets

(51) Int. Cl.
*A61F 2/966* (2013.01)
*A61M 27/00* (2006.01)

(58) Field of Classification Search
CPC .. A61F 2/856; A61F 2/848; A61B 2017/1135; A61B 17/11
See application file for complete search history.

(56) References Cited

U.S. PATENT DOCUMENTS

| | | |
|---|---|---|
| 5,830,224 A | 11/1998 | Cohn et al. |
| 6,068,638 A | 5/2000 | Makower |
| 6,099,542 A | 8/2000 | Cohn et al. |
| 6,159,225 A | 12/2000 | Makower |
| 6,165,185 A | 12/2000 | Shennib et al. |
| 6,190,353 B1 | 2/2001 | Makower et al. |
| 6,231,587 B1 | 5/2001 | Makower |
| 6,251,116 B1 | 6/2001 | Shennib et al. |
| 6,283,983 B1 | 9/2001 | Makower et al. |
| 6,330,884 B1 | 12/2001 | Kim |
| 6,336,937 B1 | 1/2002 | Vonesh et al. |
| 6,352,543 B1 | 3/2002 | Cole |
| 6,432,127 B1 | 8/2002 | Kim et al. |
| 6,458,140 B2 | 10/2002 | Akin et al. |
| 6,464,709 B1 | 10/2002 | Shennib et al. |
| 6,517,558 B2 | 2/2003 | Gittings et al. |
| 6,579,311 B1 | 6/2003 | Makower |
| 6,613,081 B2 | 9/2003 | Kim et al. |
| 6,616,675 B1 | 9/2003 | Evard et al. |
| 6,652,540 B1 | 11/2003 | Cole et al. |
| 6,655,386 B1 | 12/2003 | Makower et al. |
| 6,669,709 B1 | 12/2003 | Cohn et al. |
| 6,673,107 B1 | 1/2004 | Brandt et al. |
| 6,709,440 B2 | 3/2004 | Callol et al. |
| 6,746,464 B1 | 6/2004 | Makower |
| 6,756,565 B2 | 6/2004 | Suenaga et al. |
| 6,863,684 B2 | 3/2005 | Makower et al. |
| 6,929,009 B2 | 8/2005 | Makower et al. |
| 7,059,330 B1 | 6/2006 | Makower et al. |
| 7,134,438 B2 | 11/2006 | Makower et al. |
| 7,159,592 B1 | 1/2007 | Makower et al. |
| 7,179,270 B2 | 2/2007 | Makower |
| 7,351,247 B2 | 4/2008 | Kupiecki et al. |
| 7,374,567 B2 | 5/2008 | Heuser |
| 7,387,636 B2 | 6/2008 | Cohn et al. |
| 7,407,506 B2 | 8/2008 | Makower |
| 7,431,727 B2 | 10/2008 | Cole et al. |
| 7,628,768 B2 | 12/2009 | Faul et al. |
| 7,828,814 B2 | 11/2010 | Brenneman et al. |
| 7,846,172 B2 | 12/2010 | Makower |
| 7,849,860 B2 | 12/2010 | Makower et al. |
| 7,892,246 B2 | 2/2011 | Akin et al. |
| 7,967,769 B2 | 6/2011 | Faul et al. |
| 8,016,782 B2 | 9/2011 | Brenneman et al. |
| 8,048,016 B2 | 11/2011 | Faul et al. |
| 8,062,321 B2 | 11/2011 | Heuser et al. |
| 8,075,580 B2 | 12/2011 | Makower |
| 8,088,171 B2 | 1/2012 | Brenneman |
| 8,128,685 B2 | 3/2012 | Das |
| 8,142,454 B2 | 3/2012 | Harrison et al. |
| 8,226,592 B2 | 7/2012 | Brenneman et al. |
| 8,236,014 B2 | 8/2012 | Brenneman et al. |
| 8,273,095 B2 | 9/2012 | Brenneman et al. |
| 8,382,697 B2 | 2/2013 | Brenneman et al. |
| 8,439,963 B2 | 5/2013 | Dickinson et al. |
| 8,510,832 B2 | 8/2013 | Liu et al. |
| 8,523,800 B2 | 9/2013 | Brenneman et al. |
| 8,551,032 B2 | 10/2013 | Faul et al. |
| 8,574,185 B2 | 11/2013 | Faul et al. |
| 8,641,724 B2 | 2/2014 | Brenneman et al. |
| 8,641,747 B2 | 2/2014 | Brenneman et al. |
| 8,734,472 B2 | 5/2014 | Brenneman et al. |
| 8,926,545 B2 | 1/2015 | Brenneman et al. |
| 8,932,341 B2 | 1/2015 | Brenneman |
| 8,968,233 B2 | 3/2015 | Duffy et al. |
| 9,011,362 B2 | 4/2015 | Brenneman et al. |
| 9,023,097 B2 | 5/2015 | Brenneman et al. |
| 9,108,018 B2 | 8/2015 | Dickinson et al. |
| 9,179,916 B2 | 11/2015 | Brenneman et al. |
| 9,314,329 B2 | 4/2016 | Dickinson et al. |
| 9,326,792 B2 | 5/2016 | Dickinson et al. |
| 9,463,269 B2 | 10/2016 | Cully et al. |
| 9,468,441 B2 | 10/2016 | Brenneman |
| 9,510,832 B2 | 12/2016 | Brenneman |
| 9,532,803 B2 | 1/2017 | Dickinson et al. |
| 9,545,263 B2 | 1/2017 | Lenihan et al. |
| 9,550,022 B2 | 1/2017 | Brenneman et al. |
| 9,669,148 B2 | 6/2017 | Brenneman et al. |
| 9,687,239 B2 | 6/2017 | Consigny et al. |
| 9,706,997 B2 | 7/2017 | Brenneman |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 9,814,869 B1 | 11/2017 | DiFiore |
| 9,820,745 B2 | 11/2017 | Brenneman et al. |
| 9,955,970 B2 | 5/2018 | Brenneman et al. |
| 9,993,633 B2 | 6/2018 | DiFiore |
| 10,004,508 B2 | 6/2018 | Orion et al. |
| 10,098,643 B2 | 10/2018 | Brenneman |
| 10,111,998 B2 | 10/2018 | Brenneman et al. |
| 10,136,987 B2 | 11/2018 | Dickinson et al. |
| 10,232,098 B2 | 3/2019 | Brenneman et al. |
| 10,238,816 B2 | 3/2019 | Matsubara et al. |
| 10,245,371 B2 | 4/2019 | Cully et al. |
| 10,285,800 B2 | 5/2019 | Dickinson et al. |
| 10,299,794 B2 | 5/2019 | Orion et al. |
| 10,307,164 B2 | 6/2019 | Orion et al. |
| 10,390,933 B2 | 8/2019 | Dickinson et al. |
| 10,405,967 B1 | 9/2019 | Dickinson et al. |
| 10,524,894 B1 | 1/2020 | Dickinson et al. |
| 10,596,356 B2 | 3/2020 | Lenihan et al. |
| 10,751,057 B2 | 8/2020 | Brenneman et al. |
| 10,835,366 B2 | 11/2020 | Donadio, III et al. |
| 10,835,367 B2 | 11/2020 | Dickinson et al. |
| 10,881,429 B2 | 1/2021 | Dickinson et al. |
| 2002/0062146 A1 | 5/2002 | Makower et al. |
| 2002/0138087 A1 | 9/2002 | Shennib et al. |
| 2002/0161383 A1 | 10/2002 | Akin et al. |
| 2003/0130671 A1 | 7/2003 | Duhaylongsod et al. |
| 2004/0249335 A1 | 12/2004 | Faul et al. |
| 2005/0080439 A1 | 4/2005 | Carson et al. |
| 2006/0047337 A1 | 3/2006 | Brenneman |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2008/0161901 A1 | 7/2008 | Heuser et al. |
| 2008/0161904 A1 | 7/2008 | Heuser et al. |
| 2009/0234428 A1 | 9/2009 | Snow et al. |
| 2010/0022940 A1 | 1/2010 | Thompson |
| 2011/0295104 A1 | 12/2011 | Teitelbaum et al. |
| 2012/0010556 A1 | 1/2012 | Faul et al. |
| 2012/0065652 A1* | 3/2012 | Cully ............... A61B 17/11 623/1.13 |
| 2012/0116500 A1* | 5/2012 | Jang ............... A61F 2/856 623/1.35 |
| 2013/0226067 A1 | 8/2013 | Ward et al. |
| 2015/0057687 A1 | 2/2015 | Gittard et al. |
| 2015/0148825 A1 | 5/2015 | Orion et al. |
| 2015/0289875 A1* | 10/2015 | Consigny ............... A61F 2/856 623/1.11 |
| 2016/0058452 A1 | 3/2016 | Brenneman et al. |
| 2016/0058453 A1 | 3/2016 | Orion et al. |
| 2016/0100840 A1 | 4/2016 | Brenneman et al. |
| 2016/0151056 A1 | 6/2016 | Lederman et al. |
| 2017/0232241 A1 | 8/2017 | Brenneman et al. |
| 2017/0258470 A1 | 9/2017 | Brenneman |
| 2017/0348004 A1 | 12/2017 | Brenneman et al. |
| 2018/0049742 A1 | 2/2018 | Brenneman et al. |
| 2018/0116522 A1 | 5/2018 | Brenneman et al. |
| 2018/0133441 A1 | 5/2018 | Kellerman |
| 2018/0206845 A1 | 7/2018 | Brenneman et al. |
| 2018/0280667 A1 | 10/2018 | Keren |
| 2018/0344322 A9 | 12/2018 | Orion et al. |
| 2018/0361127 A1 | 12/2018 | Gray et al. |
| 2019/0015103 A1 | 1/2019 | Sharma |

(56) References Cited

U.S. PATENT DOCUMENTS

| | | |
|---|---|---|
| 2019/0029685 A1 | 1/2019 | Brenneman |
| 2019/0083717 A1 | 3/2019 | Matsubara et al. |
| 2019/0099185 A1 | 4/2019 | Kahana et al. |
| 2019/0125349 A1 | 5/2019 | Kahana et al. |
| 2019/0143011 A1 | 5/2019 | Brenneman et al. |
| 2019/0223872 A1 | 7/2019 | Orion et al. |
| 2019/0231514 A1* | 8/2019 | Arbefeuille ............... A61F 2/07 |
| 2019/0240391 A1 | 8/2019 | Brenneman et al. |
| 2019/0298909 A1 | 10/2019 | Cully et al. |
| 2019/0358020 A1 | 11/2019 | Dickinson et al. |
| 2020/0114060 A1 | 4/2020 | Vartanian |

OTHER PUBLICATIONS

PCT International Search Report and Written Opinion in PCT/US2021/072064 dated Apr. 4, 2022.

* cited by examiner

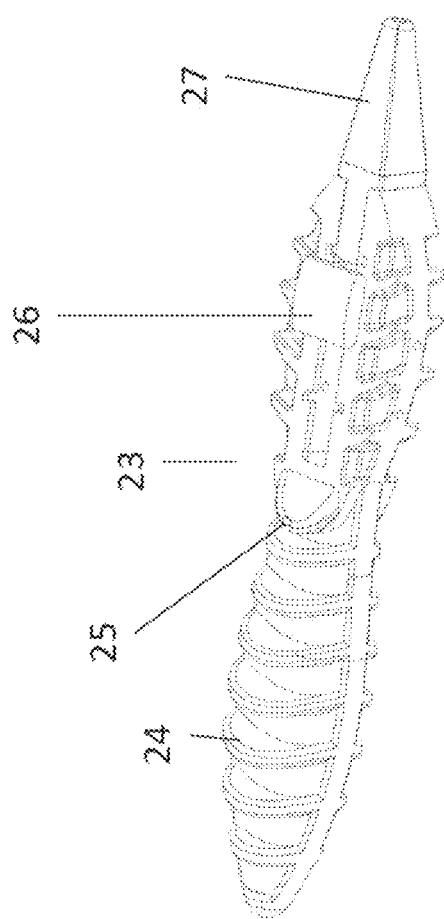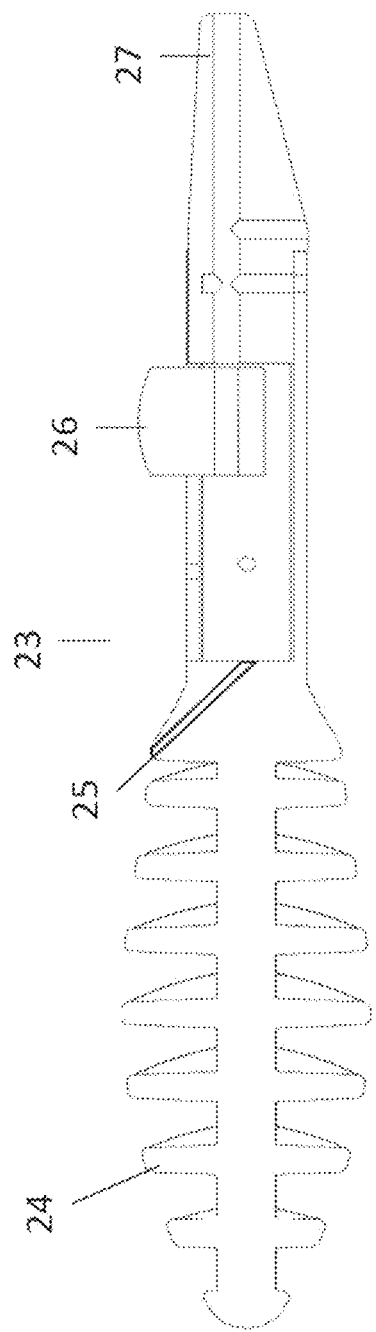
FIG. 21A
FIG. 21B

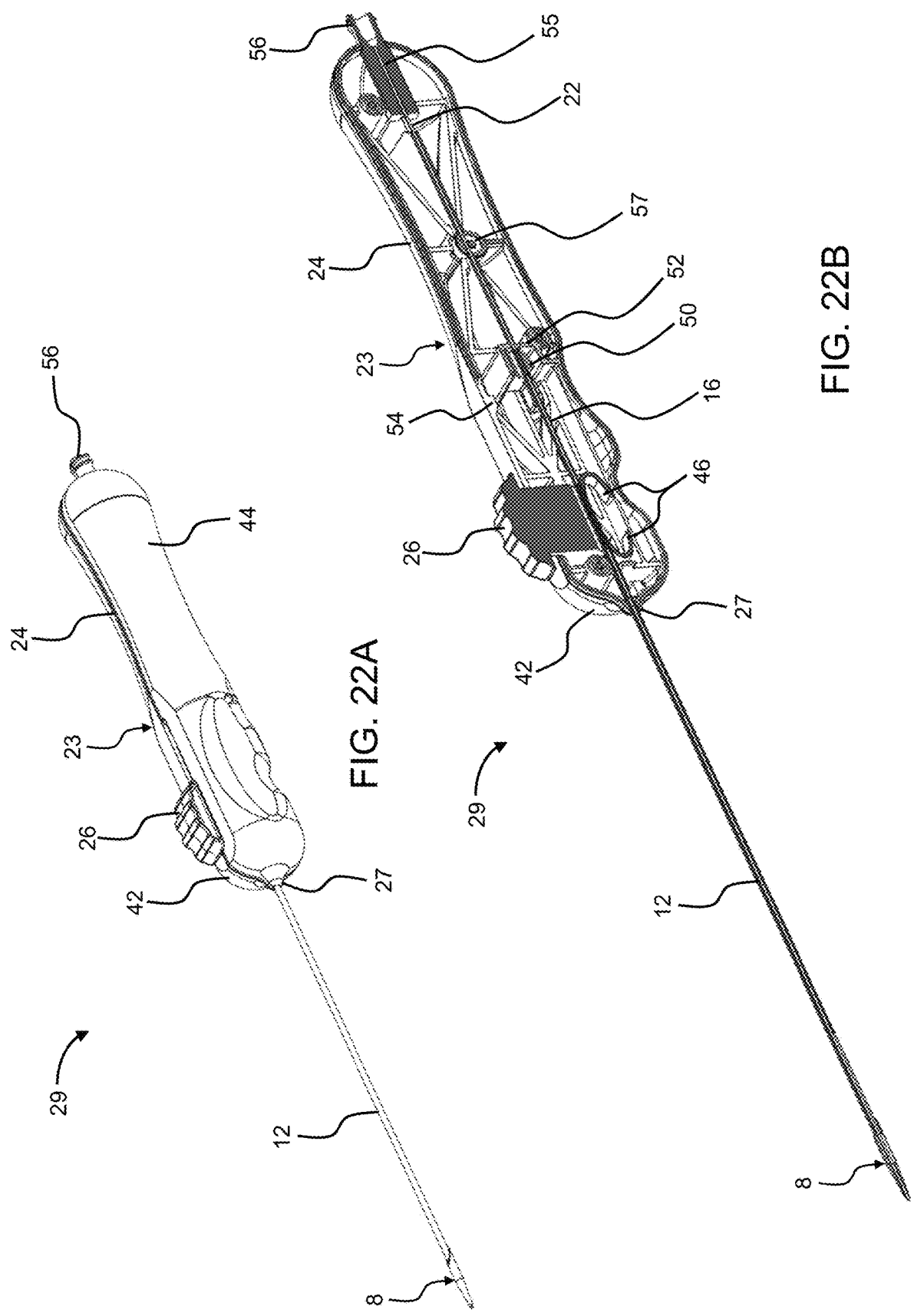

ENDOVASCULAR IMPLANTS AND DEVICES AND METHODS FOR ACCURATE PLACEMENT

CROSS-REFERENCE TO RELATED APPLICATIONS

This application claims priority to U.S. Provisional Patent Application No. 63/111,548, filed Nov. 9, 2020, and to U.S. Provisional Patent Application No. 63/245,114, filed Sep. 16, 2021, the entire contents of each of which are incorporated by reference herein in its entirety and for all purposes.

BACKGROUND

Field

Some aspects herein relate to endovascular implant systems, methods and devices which provide for accurate percutaneous placement in the vasculature.

Description of the Related Art

There are numerous interventional endovascular procedures that have been developed and are performed which require the accurate placement of implants such as endovascular stents, filters and covered stents (stent-grafts), to name a few. These endovascular procedures treat conditions such as vascular occlusive disease, vascular aneurysmal disease and other abnormalities of the vasculature. They may also be used to treat hypertension, both portal vein hypertension and systemic hypertension by shunting blood flow from the hypertensive vasculature to the lower pressure venous system. Another possible treatment that could be performed through an endovascular procedure is the creation of an arteriovenous fistula by placing a vascular implant between a vein and artery to create vascular access for hemodialysis.

These endovascular implant procedures typically rely on expensive radiographic imaging, such as fluoroscopy, and significant skill of the operator to precisely position the catheter-based delivery system prior to deployment and delivery of the implant. These techniques require special procedure rooms, the requirement to wear lead based protective equipment and the injection of toxic contrast media into the patient which can cause undue stress on the renal system. Transdermal ultrasound imaging does not provide the needed image resolution to ensure accurate positioning during these procedures. Improved implants and procedures are needed.

Hemodialysis in particular may benefit from improved implants and methods. Hemodialysis is a life-saving treatment for kidney failure that uses a machine, called a dialyzer, to filter a patient's blood outside the body. Vascular access is required to remove and return blood during the procedure. During hemodialysis, blood from the patient will flow from one point of the access (e.g., from a needle pierced into an access vein), through a tube to the dialyzer where waste and extra fluid are filtered out, then back through a different tube to a separate point of the access (e.g., through another needle pierced into the same access vein or another) in order to return it to the patient. Vascular access allows large amounts of blood to flow continuously during hemodialysis treatment so that as much blood as possible can be filtered during the procedure. Vascular access generally consists of two types: long-term use which includes arteriovenous fistulas and arteriovenous grafts, and short-term use which includes a venous catheter.

An arteriovenous (AV) fistula for use in hemodialysis is generally a connection between an artery and a vein made by a vascular surgeon. In the creation of an AV fistula, the vascular surgeon will connect an artery of the patient to a vein of the patient. Placement of the AV fistula is generally in the forearm or upper arm, and it is desired to connect an artery (which are located within muscle near deep veins) to a superficial vein (which are located atop/external the muscle and closer to the surface) for ease of access. The AV fistula exposes the vein to increased pressure and blood flow, causing it to grow large and strong. An enlarged vein provides an easier and more reliable target for vascular access, increased blood flow allows for single vein access and more blood to be filtered, and increased strength enables the vein to handle the repeated needle insertions of serial treatments as well as prevents the vein from collapsing during the procedure.

An AV graft for use in hemodialysis is generally a looped, plastic tube implanted in the patient (e.g., it does not exit the skin) that connects an artery and a vein, installed surgically by a vascular surgeon. As opposed to a patient's vein being used for vascular access during hemodialysis, the AV graft is used for access to the vasculature (e.g., access needles are pierced through the graft tubing instead of a patient's vein).

A venous catheter for use in hemodialysis is a tube inserted into a vein in the patient's neck, chest, or leg near the groin, usually only for short-term hemodialysis due to the increased risk of sepsis and mortality by this approach. The tube splits in two after exiting the body to allow for the two connections typical of hemodialysis treatment (e.g., blood out, filtered blood in). If a patient's disease has progressed quickly, a patient may not have time for placement of an AV fistula or an AV graft before starting hemodialysis treatments, as both generally require 2-3 months to develop/mature before they can be used for hemodialysis; in this situation, a venous catheter may be required until longer-term vascular access is developed.

Among the ways to create access for hemodialysis, an AV fistula is preferred over the other types mentioned because it provides for good blood flow for dialysis, it lasts longer, and is less likely to get infected or cause blood clots than the other types of access. Although preferred, there remain drawbacks to the current practices of creating an AV fistula. One of the main drawbacks includes the requirement for a vascular surgeon to surgically create the AV fistula, which requires appropriate personnel, facilities and infrastructure to perform.

More recent methods for creating an AV fistula, such as by catheter electrocautery, may allow for a more non-invasive approach but they do not overcome all the drawbacks of the traditional surgical method and can introduce new drawbacks. Namely, due to the anatomical requirement that the AV fistula be created in adjacent vessels by a catheter electrocautery approach, an AV fistula will be created between an artery and a deep vein, not an artery and a superficial vein directly which is the desired type of access vein for hemodialysis. While perforating veins do extend between and connect deep veins to superficial veins, deep veins also have multiple branching points in the anatomical areas typically used for the creation of an AV fistula. Thus, an AV fistula created by a catheter electrocautery approach may disperse blood flow from the artery through multiple venous branches, and only a portion may be directed to a desired superficial vein which may not be enough to induce the required anatomical changes in the superficial vein as discussed above or provide the required blood flow for a hemodialysis treatment procedure. Secondary procedures such as band ligation and embolization of the connected branching veins may be required to direct blood from the artery to the desired superficial vein, which delay the availability of long-term vascular access for the patient and require extended access via a venous catheter, subjecting the patient to the increased risks of that access modality. There remains a need for improved methods, systems and devices for creating an AV fistula for hemodialysis.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

In some embodiments, disclosed herein is a system for creating an arteriovenous fistula in an arm of a patient, the system comprising: an endovascular delivery device configured for access into the arm of the patient, wherein the endovascular delivery device is configured to be advanced into a superficial vein, into a perforator vein, into a deep vein, and into an artery adjacent to the deep vein; and an intraluminal implant, wherein the endovascular delivery device is configured to carry the intraluminal implant in a radially compressed configuration into the arm of the patient, the intraluminal implant comprising: a proximal implant segment comprising a proximal end and a distal end, the proximal implant segment being releasable from the endovascular delivery device to transform from a radially compressed configuration to a radially expanded configuration in which the proximal implant segment extends through the perforator vein and the deep vein with the proximal end of the proximal implant segment positioned within the perforator vein; and a distal implant segment connected to the proximal implant segment, the distal implant segment being releasable from the endovascular delivery device to transform from a radially compressed configuration to a radially expanded configuration in which the distal implant segment is positioned within the artery, wherein the distal end of the proximal implant segment is configured to be at an angle relative to an axis of the distal implant segment; wherein when the proximal implant segment is in the radially expanded configuration extending through the perforator vein and the deep vein and the distal implant segment is in the radially expanded configuration within the artery, the proximal implant segment is configured to divert flow from the artery into the superficial vein.

In the above system or in other embodiments as described herein, one or more of the following features may also be provided. In some embodiments, the distal implant segment is configured to anchor against a wall of the artery. In some embodiments, the distal implant segment comprises a tubular body configured to provide radial support to the artery. In some embodiments, the proximal implant segment comprises a tubular body configured to radially engage a wall of the perforator vein. In some embodiments, the distal end of the proximal implant segment is configured to be secured to a wall of the artery. In some embodiments, the distal end of the proximal implant segment comprises an anchor configured to anchor against the wall of the artery. In some embodiments, one or both of the proximal implant segment and the distal implant segment is covered with a graft material. In some embodiments, the implant comprises a side opening between the distal end of the proximal implant segment and a proximal end of the distal implant segment, wherein when the proximal implant segment is in the radially expanded configuration extending through the perforator vein and the deep vein and the distal implant segment is in the radially expanded configuration within the artery, blood flowing through the artery enters the side opening and (i) flows through the proximal end of the distal implant segment and out a distal end of the distal implant segment, and (ii) flows through the distal end of the proximal implant segment and out the proximal end of the proximal implant segment. In some embodiments, the distal end of the proximal implant segment comprises an anastomotic ring. In some embodiments, the distal end of the proximal implant segment is configured to be angled relative to an axis of the distal implant segment by between about 0 degrees to about 90 degrees. In some embodiments, the distal implant segment is connected to the proximal implant segment by at least one connecting strut. In some embodiments, the delivery device comprises a sheath configured to constrain the intraluminal implant in a radially compressed configuration within a distal end of the sheath. In some embodiments, the delivery device further comprises a nose cone advanceable into the artery, and wherein the distal end of the sheath is configured to be inserted within a cavity of the nose cone for advancement with the nose cone into the artery. In some embodiments, the nose cone comprises a tapered proximal end configured to engage a near wall of the artery. In some embodiments, the delivery device is configured such that, after the distal end of the sheath is advanced with the nose cone into the artery: the sheath is retractable in a proximal direction relative to the nose cone to expand the proximal implant segment within the deep vein and the perforator vein; and the nose cone is distally advanceable relative to the distal implant segment after the proximal implant segment is expanded within the deep vein and the perforator vein to expand the distal implant segment within the artery. In some embodiments, the delivery device is configured such that, after the distal implant segment is expanded within the artery, the sheath is advanceable through the expanded proximal implant segment and the expanded distal implant segment into engagement with the nose cone to facilitate removal of the nose cone with the sheath from the artery. In some embodiments, the delivery device further comprises a guidewire shaft configured to be advanced over a guidewire, wherein the nose cone is fixed to the guidewire shaft.

In some embodiments, disclosed herein is a method of creating an arteriovenous fistula in an arm of a patient, comprising: delivering an intraluminal implant in a collapsed configuration into the patient, the intraluminal implant comprising a proximal implant segment and a distal implant segment, wherein the proximal implant segment is connected to the distal implant segment; extending the intraluminal implant between a deep vein and an artery adjacent the deep vein, wherein the proximal implant segment extends through a perforator vein and the deep vein and the distal implant segment is positioned within the artery; and radially expanding the proximal implant segment to cause the proximal implant segment to engage a wall of the perforator vein and radially expanding the distal implant segment to cause the distal implant segment to engage a wall of the artery and provide radial support for the artery, such that blood flowing through the artery is diverted from the artery into a superficial vein connected to the perforator vein.

In the above method or in other embodiments as described herein, one or more of the following features may also be provided. In some embodiments, the intraluminal implant comprises a side opening between a distal end of the proximal implant segment and a proximal end of the distal implant segment, such that after the proximal implant segment is radially expanded to engage the wall of the perforator vein and the distal implant segment is radially expanded to engage the wall of the artery, blood flowing through the artery enters the side opening and (i) flows through the proximal end of the distal implant segment and a distal end of the distal implant segment to continue through the artery, and (ii) flows through the distal end of the proximal implant segment and out a proximal end of the proximal implant segment to flow into the perforator vein and into the superficial vein. In some embodiments, the proximal implant segment and the distal implant segment comprise tubular bodies. In some embodiments, the method further comprises anchoring a distal end of the proximal implant segment to the wall of the artery. In some embodiments, after the proximal implant segment is radially expanded to engage the wall of the perforator vein and the distal implant segment is radially expanded to engage the wall of the artery, the proximal implant segment is angled relative to an axis of the distal implant segment. In some embodiments, the proximal implant segment is angled relative to an axis of the distal implant segment by between about 0 degrees to about 90 degrees. In some embodiments, the intraluminal implant is delivered into the patient within a sheath constraining the intraluminal implant at a distal end of the sheath. In some embodiments, the distal end of the sheath is advanced into the artery within a cavity of a nose cone. In some embodiments, the proximal implant segment is released from the sheath to radially expand into engagement with the wall of the perforator vein by proximally retracting the sheath relative to the nose cone. In some embodiments, the distal implant segment is radially expanded into engagement with the wall of the artery by distally advancing the nose cone relative to the distal implant segment. In some embodiments, the method further comprises distally advancing the sheath through the radially expanded proximal implant segment and the radially expanded distal implant segment into engagement with the nose cone, and proximally retracting the sheath engaged with the nose cone through the radially expanded proximal implant segment and the radially expanded distal implant segment. In some embodiments, the nose cone comprises a tapered proximal end that engages with a wall of the artery while the sheath is proximally retracted to release the proximal implant segment. In some embodiments, the nose cone is rotated within the artery after the nose cone has been distally advanced to release the distal implant segment and before proximally retracting the sheath engaged with the nose cone through the radially expanded proximal implant segment and the radially expanded distal implant segment.

In some embodiments, disclosed herein is a method of creating an arterio-venous fistula, comprising: accessing a superficial vein; advancing an access tool into the superficial vein, into a perforator vein, and into a deep vein; advancing the access tool through a luminal wall of the deep vein, through an or any interstitial space, and through an adventitial wall of an artery (also sometimes referred to herein as a "deep artery"); advancing a guidewire through the access tool into the artery; withdrawing the access tool over the guidewire; and/or advancing a device (also referred to herein as a "delivery device") over the guidewire such that a distal end of the device is within the artery and a more proximal segment of the device spans the or any interstitial space.

In the above method or in other embodiments as described herein, one or more of the following features may also be provided. In some embodiments, the method can include, wherein advancing the access tool through the luminal wall of the deep vein, through the or any interstitial space, and through the adventitial wall of an artery comprises actuating a port proximate the proximate end of the access tool, thereby causing a sharpened needle tip to extend distally from a distal end of the access tool. In some embodiments, actuating a port comprises depressing the port and compressing a spring element operably connected to the sharpened needle tip. In some embodiments, the method further comprises releasing the port, thereby allowing the spring element to recoil and cause the sharpened needle tip to retract proximally into the distal end of the access tool. In some embodiments, the device or delivery device comprises a nose cone. In some embodiments, the nose cone comprises a proximal tapered end, a central lumen, a distal tapered end, and a longitudinal axis. In some embodiments, the device or delivery device comprises a flexible sheath comprising a longitudinal axis. In some embodiments, an implant is carried within the flexible sheath in a radially compressed configuration. In some embodiments, after advancing the device or delivery device over the guidewire, a distal end of the flexible sheath resides within the central lumen of the nose cone, and a gap is formed between the proximal tapered end of the nose cone and a sidewall of the flexible sheath as it enters the central lumen of the nose cone at the proximal tapered end of the nose cone, and wherein the longitudinal axis of the flexible sheath is not coaxial with the longitudinal axis of the nose cone. In some embodiments, the length of the gap is between about 5% and about 50% of a diameter of the proximal tapered end of the nose cone. In some embodiments, no gap between the proximal tapered end of the nose cone and a sidewall of the flexible sheath is formed and/or required. In some embodiments, the method further comprises withdrawing the nose cone and the flexible sheath proximally such that the nose cone engages a near wall of the artery. In some embodiments, the method further comprises withdrawing the sheath proximally, thereby allowing a proximal segment of the implant to transform from the radially compressed configuration to a radially expanded configuration. In some embodiments, withdrawing the sheath proximally releases an anchor that engages the proximal segment of the implant with respect to the near wall of the artery. In some embodiments, a distal segment of the implant remains within the nose cone in a radially compressed configuration while the proximal segment of the implant is in the radially expanded configuration. In some embodiments, the method further comprises advancing the nose cone with respect to the distal segment of the implant, thereby transforming the distal segment of the implant to a radially expanded configuration. In some embodiments, advancing the nose cone releases an anchor that engages the proximal segment of the implant with respect to the near wall of the artery. In some embodiments, withdrawing the sheath proximally releases an anchor that engages the proximal segment of the implant with respect to the near wall of the artery. In some embodiments, the method further comprises advancing the sheath distally through the distal segment of the implant in the radially enlarged configuration, thereby engaging the nose cone. In some embodiments, the method further comprises rotating the nose cone around its longitudinal axis. In some embodiments, the method further comprises withdrawing the nose cone and the flexible sheath proximally out of the artery, the or any interstitial space, the deep vein, the perforator vein, and the superficial vein, leaving the implant in place.

In some embodiments, disclosed herein is a method of creating a fistula, comprising: advancing an access tool through a luminal wall of a first lumen, through an or any interstitial space, and through an outer wall of a second lumen; advancing a guidewire through the access tool into the second lumen; withdrawing the access tool over the guidewire; and/or advancing a device (also referred to herein as a "delivery device") over the guidewire such that a distal end of the device is within the second lumen and a more proximal segment of the device spans the or any interstitial space, wherein the device comprises a nose cone comprising a proximal tapered end, a central lumen, a distal tapered end, and a longitudinal axis, and a flexible sheath comprising a longitudinal axis, wherein after advancing the device over the guidewire, a distal end of the flexible sheath resides within the central lumen of the nose cone, and a gap is formed between the proximal tapered end of the nose cone and a sidewall of the flexible sheath as it enters the central lumen of the nose cone at the proximal tapered end of the nose cone, and wherein the longitudinal axis of the flexible sheath is not coaxial with the longitudinal axis of the nose cone.

In the above method or in other embodiments as described herein, one or more of the following features may also be provided. In some embodiments, the length of the gap is between about 5% and about 50% of a diameter of the proximal tapered end of the nose cone. In some embodiments, the gap is formed at least partially by deflecting the nose cone with respect the flexible sheath. In some embodiments, no gap between the proximal tapered end of the nose cone and a sidewall of the flexible sheath is formed and/or required. In some embodiments, deflecting the nose cone comprises actuating at least one pullwire. In some embodiments, the method further comprises withdrawing the nose cone and the flexible sheath proximally such that the nose cone engages a near wall of the second lumen. In some embodiments, an implant is carried within the flexible sheath in a radially compressed configuration. In some embodiments, the method further comprises withdrawing the sheath proximally, thereby allowing a proximal segment of the implant to transform from the radially compressed configuration to a radially expanded configuration. In some embodiments, withdrawing the sheath proximally releases an anchor that engages the proximal segment of the implant with respect to the near wall of the second lumen. In some embodiments, a distal segment of the implant remains within the nose cone in a radially compressed configuration while the proximal segment of the implant is in the radially expanded configuration. In some embodiments, the method further comprises advancing the nose cone with respect to the distal segment of the implant, thereby transforming the distal segment of the implant to a radially expanded configuration. In some embodiments, advancing the nose cone releases an anchor that engages the proximal segment of the implant with respect to the near wall of the second lumen.

In some embodiments, disclosed herein is an intraluminal delivery system or device comprising: a nose cone comprising a proximal tapered end, a central lumen, a distal tapered end, and a longitudinal axis, and a flexible sheath comprising a longitudinal axis, wherein the device is configured such that a distal end of the flexible sheath is configured to reside within the central lumen of the nose cone such that a gap is formed between the proximal tapered end of the nose cone and a sidewall of the flexible sheath as it enters the central lumen of the nose cone at the proximal tapered end of the nose cone when the longitudinal axis of the flexible sheath is not coaxial with the longitudinal axis of the nose cone.

In the above system or device or in other embodiments as described herein, one or more of the following features may also be provided. In some embodiments, the nose cone comprises a slit. In some embodiments, the slit is on the proximal tapered end of the nose cone. In some embodiments, no gap between the proximal tapered end of the nose cone and a sidewall of the flexible sheath is formed and/or required.

In some embodiments, disclosed herein is an intraluminal implant, comprising: a proximal implant segment, a distal implant segment, and at least one axially-oriented connecting strut connecting the proximal implant segment and the distal implant segment, the proximal implant segment and the distal implant segment comprising a flow lumen therethrough, wherein the at least one axially-oriented connecting strut serves as the only connection between the proximal implant segment and the distal implant segment, wherein an axial length of the proximal implant segment is greater than an axial length of the distal implant segment, wherein the implant comprises a shape memory material.

In the above implant or in other embodiments as described herein, one or more of the following features may also be provided. In some embodiments, the implant is configured such that the distal implant segment comprises a diameter different than a diameter of the proximal implant segment when the implant is in an unstressed state. In some embodiments, the implant is configured such that the distal implant segment comprises a diameter smaller than a diameter of the proximal implant segment when the implant is in an unstressed state. In some embodiments, the implant is configured such that the distal implant segment comprises a perimeter different than a perimeter of the proximal implant segment when the implant is in an unstressed state. In some embodiments, the implant is configured such that the distal implant segment comprises a perimeter smaller than a perimeter of the proximal implant segment when the implant is in an unstressed state. In some embodiments, the implant is configured such that the distal implant segment comprises a cross-sectional area different than a cross-sectional area of the proximal implant segment when the implant is in an unstressed state. In some embodiments, the implant is configured such that the distal implant segment comprises a cross-sectional area smaller than a cross-sectional area of the proximal implant segment when the implant is in an unstressed state. In some embodiments, the implant is configured such that the proximal implant segment comprises a variable diameter and/or cross-sectional area when the implant is in an unstressed state. In some embodiments, the implant is configured such that a distal edge of the proximal implant segment comprises a continuous strut and/or ring. In some embodiments, the implant is configured such that a distal edge of the proximal implant segment comprises a continuous strut and/or ring with one or more anchors. In some embodiments, the implant is configured such that the proximal implant segment comprises struts of uniform lengths. In some embodiments, the implant is configured such that the proximal implant segment comprises struts of variable lengths and/or variable widths. In some embodiments, the implant is configured such that the proximal implant segment comprises struts with lengths different than lengths of struts of the distal implant segment. In some embodiments, the implant is configured such that the distal implant segment is longitudinally offset from the proximal implant segment when the implant is in an unstressed state. In some embodiments, the proximal implant segment comprises a biocompatible graft material. In some embodiments, the distal implant segment comprises a biodegradable graft material. In some embodiments, the implant comprises a porous or non-porous laminating layer. In some embodiments, the implant comprises a coating comprising heparin and/or a therapeutic agent.

In some embodiments, disclosed herein is an intraluminal implant for creating an arteriovenous fistula, comprising: a proximal implant segment comprising a proximal end and a distal end, the proximal implant segment configured to extend through a perforator vein and a deep vein with the proximal end of the proximal implant segment configured to be positioned within the perforator vein; and a distal implant segment connected to the proximal implant segment and configured to be positioned within an artery adjacent to the deep vein, wherein the distal end of the proximal implant segment is configured to be angled relative to an axis of the distal implant segment; wherein the proximal implant segment is configured to divert flow from the artery into a superficial vein connected to the perforator vein.

In the above implant or in other embodiments as described herein, one or more of the following features may also be provided. In some embodiments, the proximal implant segment and the distal implant segment comprise expandable tubular bodies. In some embodiments, the intraluminal implant comprises a side opening between the distal end of the proximal implant segment and a proximal end of the distal implant segment, such that blood flowing through the artery enters the side opening and (i) flows through the proximal end of the distal implant segment and out a distal end of the distal implant segment to continue through the artery, and (ii) flows through the distal end of the proximal implant segment and out the proximal end of the proximal implant segment to flow into the perforator vein and into the superficial vein. In some embodiments, the proximal implant segment is angled relative to an axis of the distal implant segment by between about 0 to about 90 degrees.

In some embodiments, disclosed herein is an intraluminal implant for creating an arterio-venous fistula, comprising: a venous implant segment comprising a first expandable tubular body having a first end and a second end and a lumen extending therethrough, wherein the first expandable tubular body is configured to be collapsed for delivery into a patient and is expandable to radially engage an inner wall of a vein; and an arterial implant segment comprising a second expandable tubular body having a first end and a second end and a lumen extending therethrough, wherein the second expandable tubular body is configured to be collapsed for delivery into the patient and is expandable to radially engage an inner wall of an artery located adjacent to the vein; wherein the second end of the venous implant segment is connected to the first end of the arterial implant segment to allow for the arterial implant segment to be angled relative to the venous implant segment when the venous implant segment and the arterial implant segment are in expanded configurations, and wherein angling of the arterial implant segment relative to the venous implant segment increases a distance between the second end of the venous implant segment and the first end of the arterial implant segment along one side of the implant to provide a side opening into the implant; and wherein when the venous implant segment radially engages the inner wall of the vein and the arterial implant segment radially engages the inner wall of the artery adjacent to the vein, blood flowing through the artery enters the side opening and (i) flows through the first end of the arterial implant segment and out the second end of the arterial implant segment, and (ii) flows through the second end of the venous implant and out the first end of the venous implant segment.

In some embodiments, disclosed herein is a delivery device for delivering a vascular implant between a vein and an artery, comprising: an outer sheath configured to constrain the implant in a low-profile configuration at a distal end of the outer sheath; and a nose cone comprising a proximal end and a distal end and a cavity, wherein the distal end of the outer sheath is insertable into the cavity for advancement of the nose cone and the distal end of the outer sheath through the vein and into the artery; wherein the outer sheath is retractable in a proximal direction relative to the nose cone to expand a distal segment of the implant within the cavity; wherein the outer sheath is further retractable in a proximal direction relative to the nose cone to expand a proximal segment of the implant within the vein; and wherein the nose cone is distally advanceable relative to the distal segment of the implant after the proximal segment is expanded within the vein to release the distal segment of the implant from the cavity within the artery.

In the above device or in other embodiments as described herein, one or more of the following features may also be provided. In some embodiments, the distal end of the nose cone is tapered. In some embodiments, the proximal end of the nose cone is tapered. In some embodiments, the proximal end of the nose cone is at an angle relative to a longitudinal length of the nose cone. In some embodiments, a tapered proximal end of the nose cone is configured to engage a near wall of the artery after the nose cone is advanced into the artery. In some embodiments, the distal end of the outer sheath is advanceable through the distal segment of the implant and into the cavity after the release of the distal segment of the implant within the artery. In some embodiments, the distal end of the outer sheath is advanceable through the distal segment of the implant after the release of the distal segment of the implant within the artery to engage the proximal end of the nose cone, such that the nose cone enters the distal end of the outer sheath. In some embodiments, the delivery device further comprises a guidewire shaft configured to be advanced over a guidewire, wherein the nose cone is fixed to the guidewire shaft. In some embodiments, the delivery device further comprises a control knob connected to a proximal end of the outer sheath configured to retract and/or advance the outer sheath upon proximal and/or distal movement of the control knob, the control knob at least partially disposed within a handle of the delivery device. In some embodiments, the control knob is configured to releasably lock into a proximal most and/or a distal most position within the handle. In some embodiments, the delivery device further comprises a middle shaft within the outer sheath configured to prevent the implant from slipping proximally during retraction of the outer sheath. In some embodiments, a distal end of the middle shaft leads the distal end of the outer sheath when the outer sheath is advanced into the cavity. In some embodiments, the delivery device further comprises a middle shaft connector disposed within the handle and connected to a proximal end of the middle shaft, the middle shaft connector configured to engage with the control knob and cause the middle shaft to advance with the outer sheath when the outer sheath is advanced into the cavity. In some embodiments, the implant is constrained within the distal end of the outer sheath.

In some embodiments, disclosed herein is a method of creating an arteriovenous fistula between an artery and a vein of a patient, comprising: delivering an intraluminal implant in a collapsed configuration into the patient, the intraluminal implant comprising a venous implant segment comprising a first tubular body and an arterial implant segment comprising a second tubular body, wherein the venous implant segment is connected to the arterial implant segment; extending the intraluminal implant across any interstitial space between the artery and the vein; and radially expanding the venous implant segment to radially engage the vein and radially expanding the arterial implant segment to radially engage the artery; wherein when the venous and arterial implant segments are radially engaged with the vein and the artery, respectively, the arterial implant segment is angled relative to the venous implant segment to provide a side opening into the intraluminal implant that allows blood flowing through the artery to enter the side opening and (i) flow through the second tubular body of the arterial implant segment to continue through the artery, and (ii) flow through the first tubular body of the venous implant segment to flow into the vein.

In some embodiments, disclosed herein is a method, system or device comprising, consisting essentially of, consisting of, and/or not comprising any number of features of the disclosure.

BRIEF DESCRIPTION OF THE DRAWINGS

The foregoing and other features, aspects, and advantages of the embodiments of the systems, devices, and methods described herein are described in detail below with reference to the drawings of various embodiments, which are intended to illustrate and not to limit the embodiments of the invention. The drawings comprise the following figures in which:

FIG. 21A depicts a perspective view of a handle of a delivery system according to some embodiments.

FIG. 21B depict a cross-sectional view of a handle of a delivery system according to some embodiments.

FIG. 22A depicts a perspective view of a delivery system according to some embodiments.

FIG. 22B depicts a cross-sectional perspective view of a delivery system according to some embodiments.

Throughout the drawings, unless otherwise noted, reference numbers may be re-used to indicate a general correspondence between referenced elements. The drawings are provided to illustrate example embodiments described herein and are not intended to limit the scope of the disclosure.

DETAILED DESCRIPTION

Embodiments disclosed herein relate generally to medical devices and methods. More particularly, some embodiments relate to endovascular implants and methods and devices to efficiently and accurately place them in the vasculature. In some embodiments the devices, methods and systems described herein allow for the precise placement of devices such as stents, including covered stents, and other implants and anastomotic devices for the creation of arteriovenous fistulas (AVF) while minimizing or eliminating the need for radiographic imaging, thus allowing them to be performed in a clinical setting with only the use of non-invasive imaging techniques, such as transdermal ultrasound. Some embodiments utilize novel means for temporarily engaging anatomical structures while delivering endovascular implants. Furthermore, in some embodiments the implants, devices, systems, and/or methods described herein advantageously overcome some or all of the drawbacks of existing implants, devices, systems, and/or methods for the creation of an AVF, including the bypassing of deep vein branching that may undesirably divert arterial blood flow away from a desired superficial vein, and the prevention or reduction of secondary procedures such as ligation and embolization.

Figure 1:
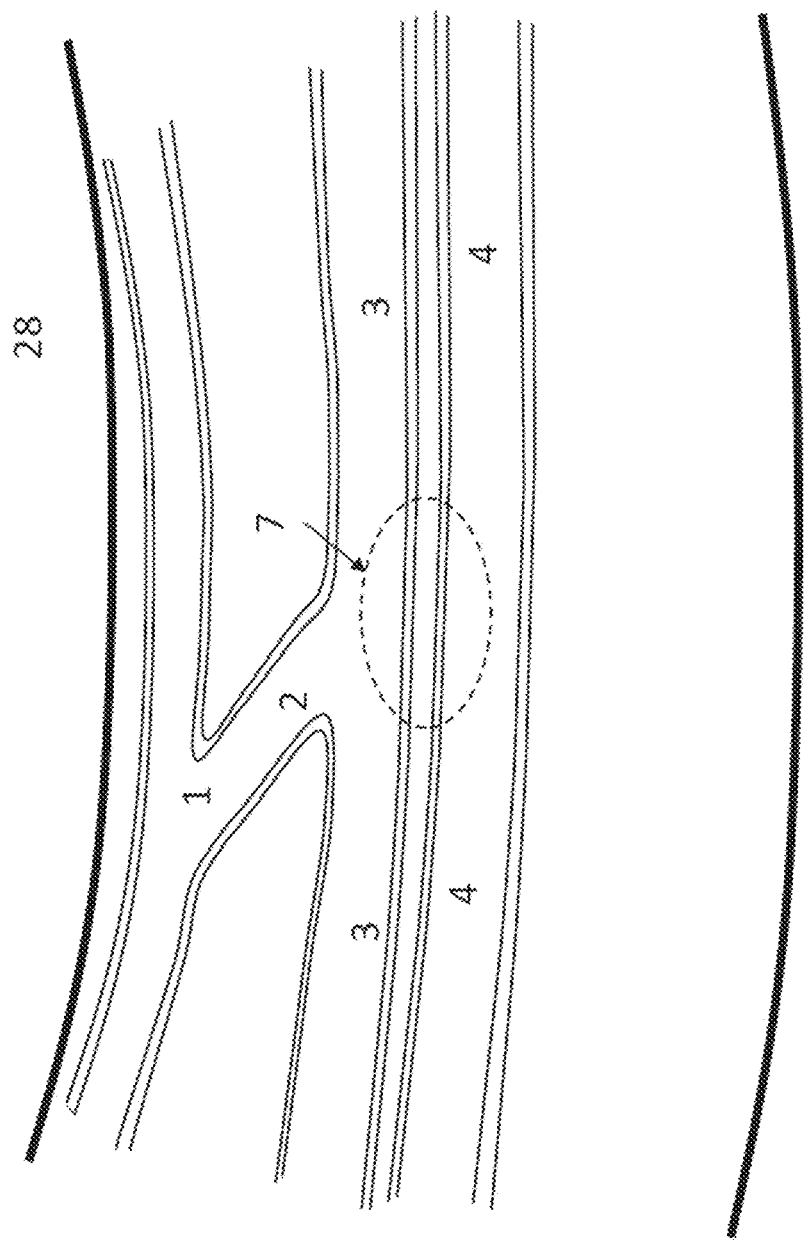
FIG. 1 depicts a simplified representation of a portion of the vasculature of the human arm indicating a potential area to create an anastomotic connection according to some embodiments.

FIG. 1 depicts a simplified representation of a portion of the vasculature of the human arm with skin surface, e.g., dermal surface 28. Location 7 is a potential area to create an anastomotic connection between a first body lumen and a second body lumen, such as, for example, an artery and a vein, such as an AVF between deep vein 3 and adjacent deep artery 4. Perforator vein 2 connects the superficial vein 1 to the deep vein 3 which lies adjacent and provides a conduit for accessing location 7. An AVF may be made between perforator vein 2 and artery 4, bypassing deep vein 3. In some embodiments, an AVF between perforator vein 2 and artery 4 may divert blood from the artery into superficial vein 1 connected to the perforator vein 2.

Figure 2A:
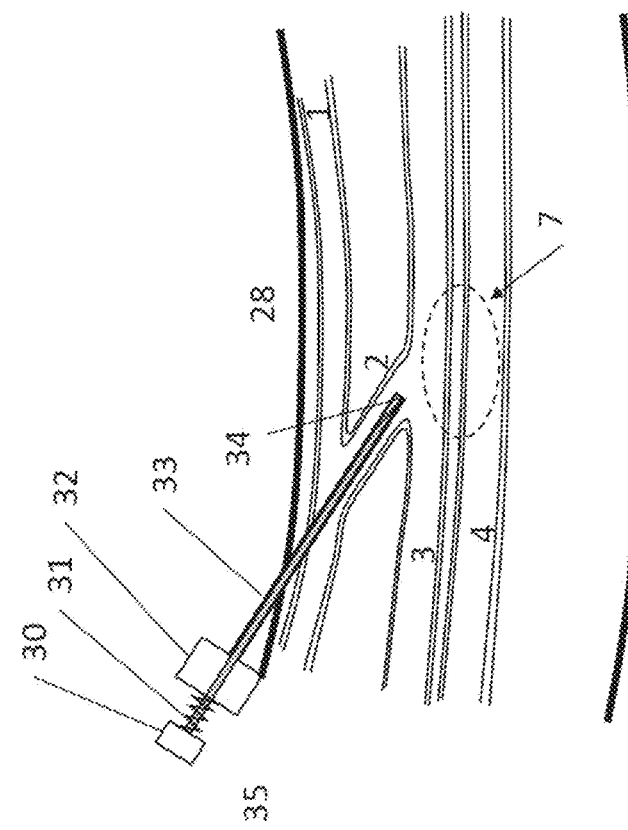
FIGS. 2A-2D depict a method of percutaneously introducing an endovascular guidewire according to some embodiments.
Figure 2B:
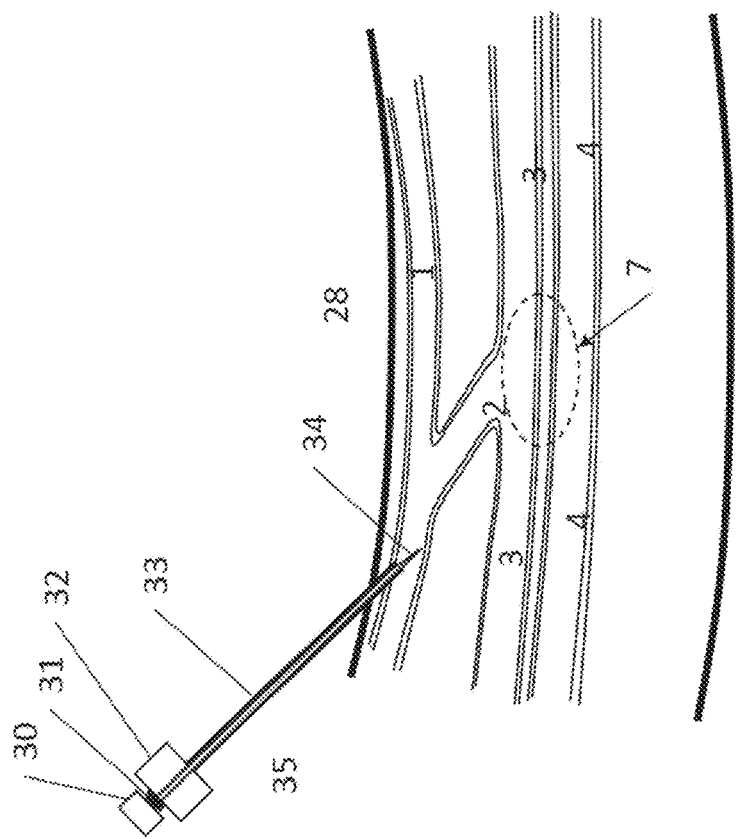
Figure 2D:
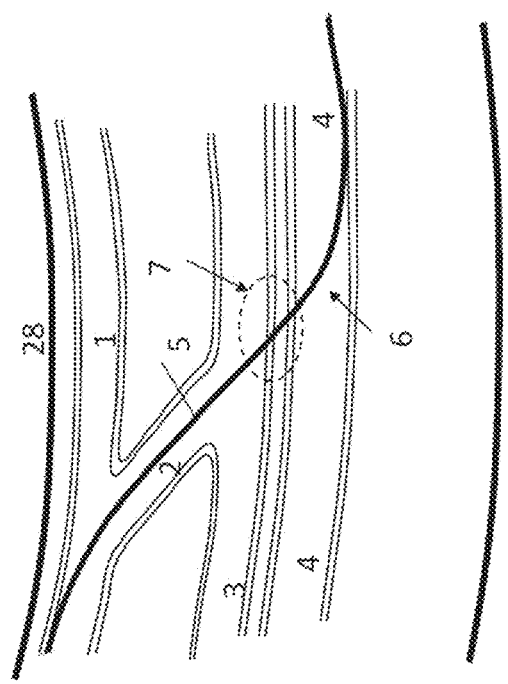
Figure 2C:
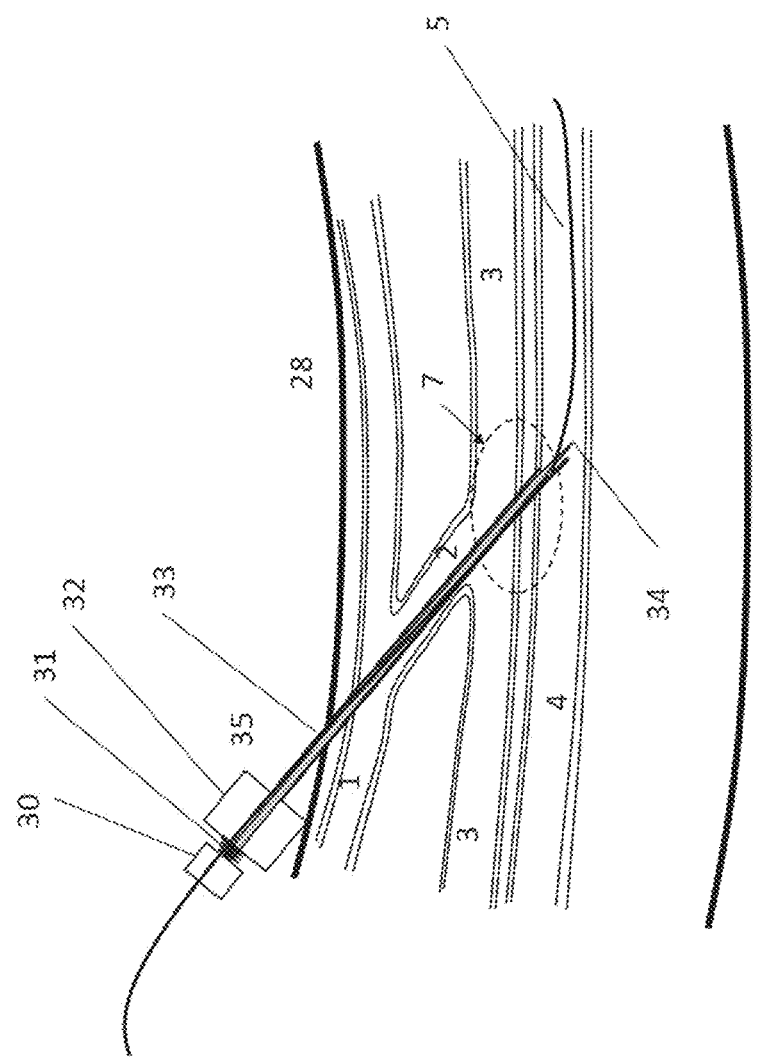

FIGS. 2A, 2B, 2C and 2D depict some embodiments of a method to percutaneously introduce endovascular guidewire 5 into deep artery 4 using needle access tool 35. Needle access tool 35 can include a hollow needle with proximal port 30 and distal sharpened tip 34 slidably deposed within sheath 33. Sheath 33 is connected to hub 32 that has compression element, such as compression spring 31 placed between port 30 and hub 32. When port 30 is depressed, needle tip 34 is exposed distally of the distal end of sheath 33 and able to puncture tissue such as skin and blood vessels. When port 30 is not depressed, spring 31 will decompress and move needle tip 34 proximally so that it is not exposed. In this configuration, the needle access device can navigate the vasculature with reduced risk of inadvertent punctures and trauma to the vasculature. Using this feature of the needle access tool 35 and appropriate imaging techniques, such as transdermal ultrasound, the needle access tool is first introduced into superficial vein 1 as shown in FIG. 2A. With needle tip 34 retracted within sheath 33, the needle access tool is navigated to location 7 using appropriate imaging as shown in FIG. 2B. While at location 7, the proximal port 30 is actuated (e.g., depressed) to expose needle tip 34 and the needle access tool 35 is then advanced to penetrate the vascular walls and any interstitial tissues between deep vein 3 and deep artery 4 until the distal end of sheath 33 enters the lumen of deep artery 4. While maintaining this position, guidewire 5 is introduced into proximal port 30 and advanced through the needle access tool 35 until the distal end of guidewire 5 exits the distal end of the needle access tool 35 and enters the lumen of deep artery 4 as shown in FIG. 2C. FIG. 2D shows guidewire 5 with curvature 6 which forms when guidewire 5 conforms to the particular vascular anatomy. Needle access tool 35 can have alternative embodiments which may include curved distal ends to allow for easier navigation through the vasculature, hemostasis valves attached to the proximal port 30 and a spring-loaded hollow needle that can aid in puncturing mobile structures. Alternative sites might also be chosen to location 7 to create the AVF. For example, a location more distal along deep vein 3 may prove more advantageous if the distance between deep vein 3 and deep artery 4 is less than at location 7. Some embodiments are not limited to connections between deep veins and deep arteries, such as in the upper extremities or the lower extremities, for example, such as in the hand, forearm, arm, foot, calf, thigh, or other areas. Some embodiments may be used to precisely locate implants in other luminal structures such as superficial veins and superficial arteries, coronary arteries, gynecological structures (e.g., the vagina, cervix, uterus, or fallopian tubes), urological structures (e.g., the ureters, bladder, or urethra) and gastrointestinal structures (e.g., esophagus, stomach, small intestine, large intestine, rectum, biliary tree, and others for example.

Figure 3:
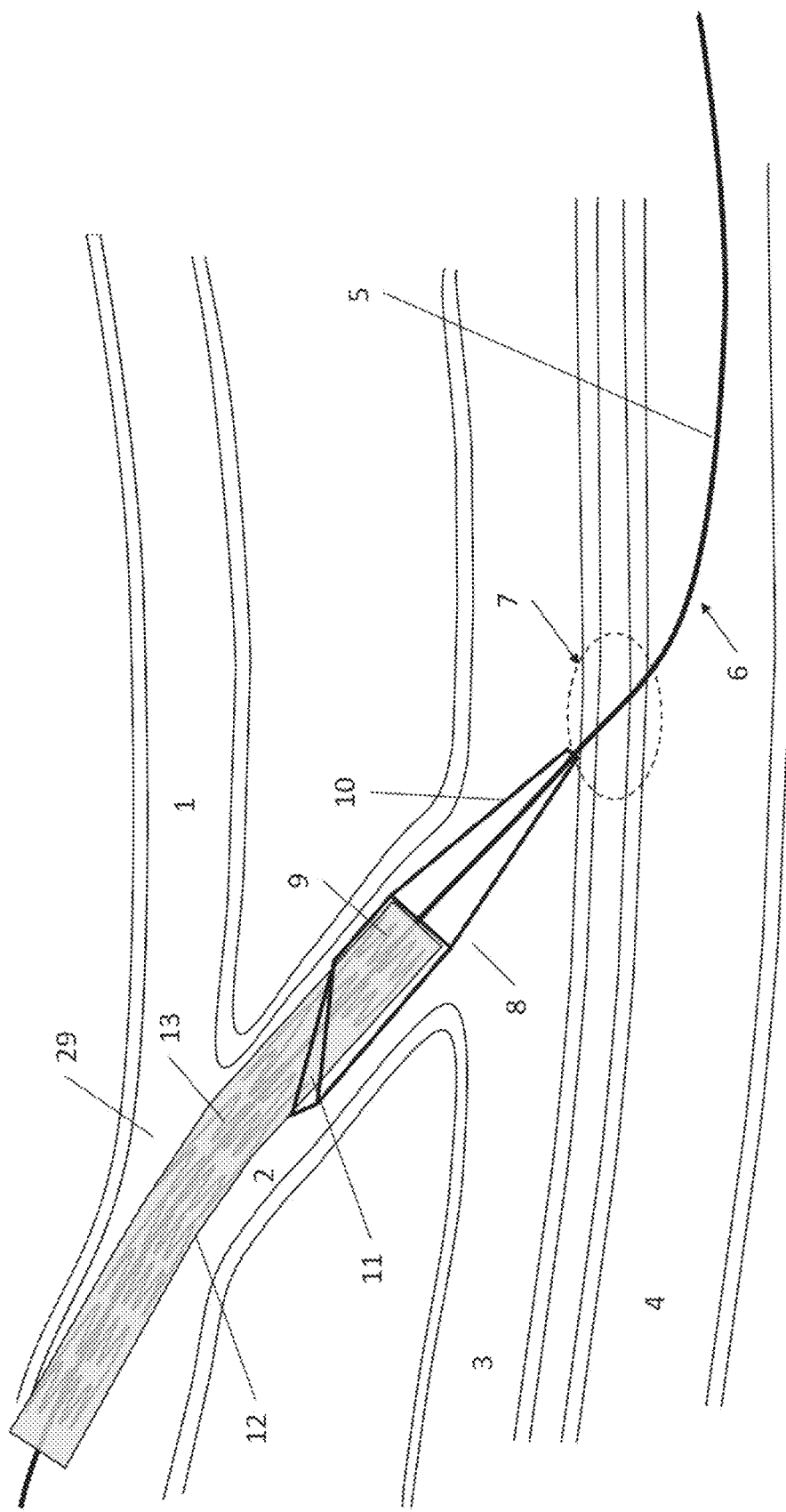
FIGS. 3-15 depict methods of percutaneously implanting an endovascular implant according to some embodiments.
Figure 8:
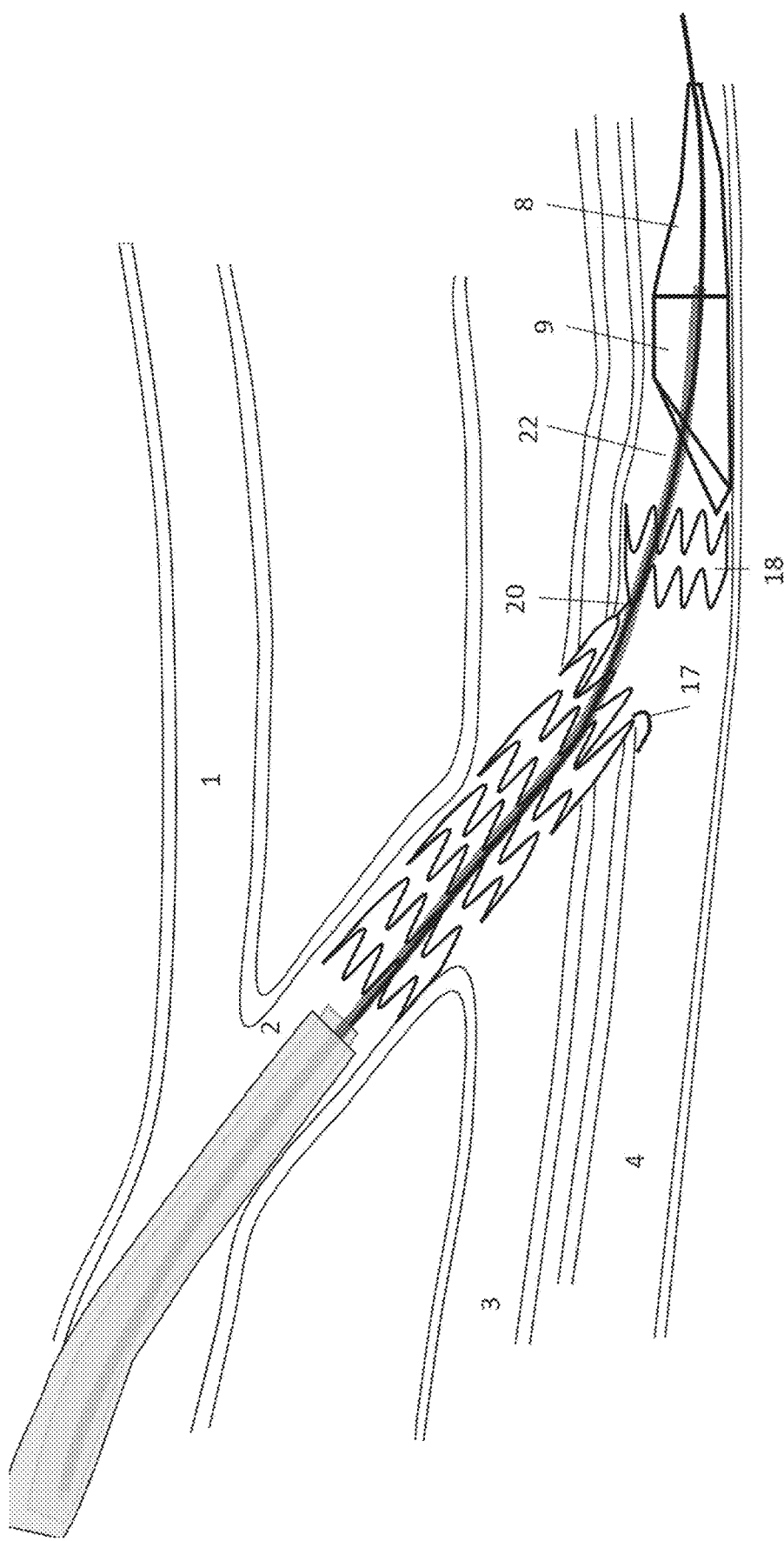

FIG. 3 depicts the distal end of an endovascular delivery system 29 with a distal nose cone 8 that has a distal taper 10, a cavity 9 (e.g., a central lumen) and tapered proximal end 11 being introduced into the vascular system and approaching AVF location 7 over guidewire 5 with a curvature 6. An outer sheath 12 is shown constraining an implant 13 in a low-profile configuration with the distal end of outer sheath 12 inserted into cavity 9. Delivery system 29 is shown with a bend conforming to guidewire 5 and the shape of the vascular anatomy. Delivery system 29 can be flexible or relatively stiff compared to the surrounding vascular structures and guidewire 5. Nose cone 8 has as a distal taper 10 so that it can more easily penetrate the vascular walls and any interstitial tissues at AVF location 7. In one embodiment, the very distal end of the distal taper 10 may have a sharpened point to further facilitate penetration of the various tissues. Nose cone 8 has features to accommodate guidewire 5 and in this embodiment is bonded or otherwise fixed to an inner guide wire shaft 22 as shown in FIG. 8, but not shown in FIG. 3.

Figure 4:
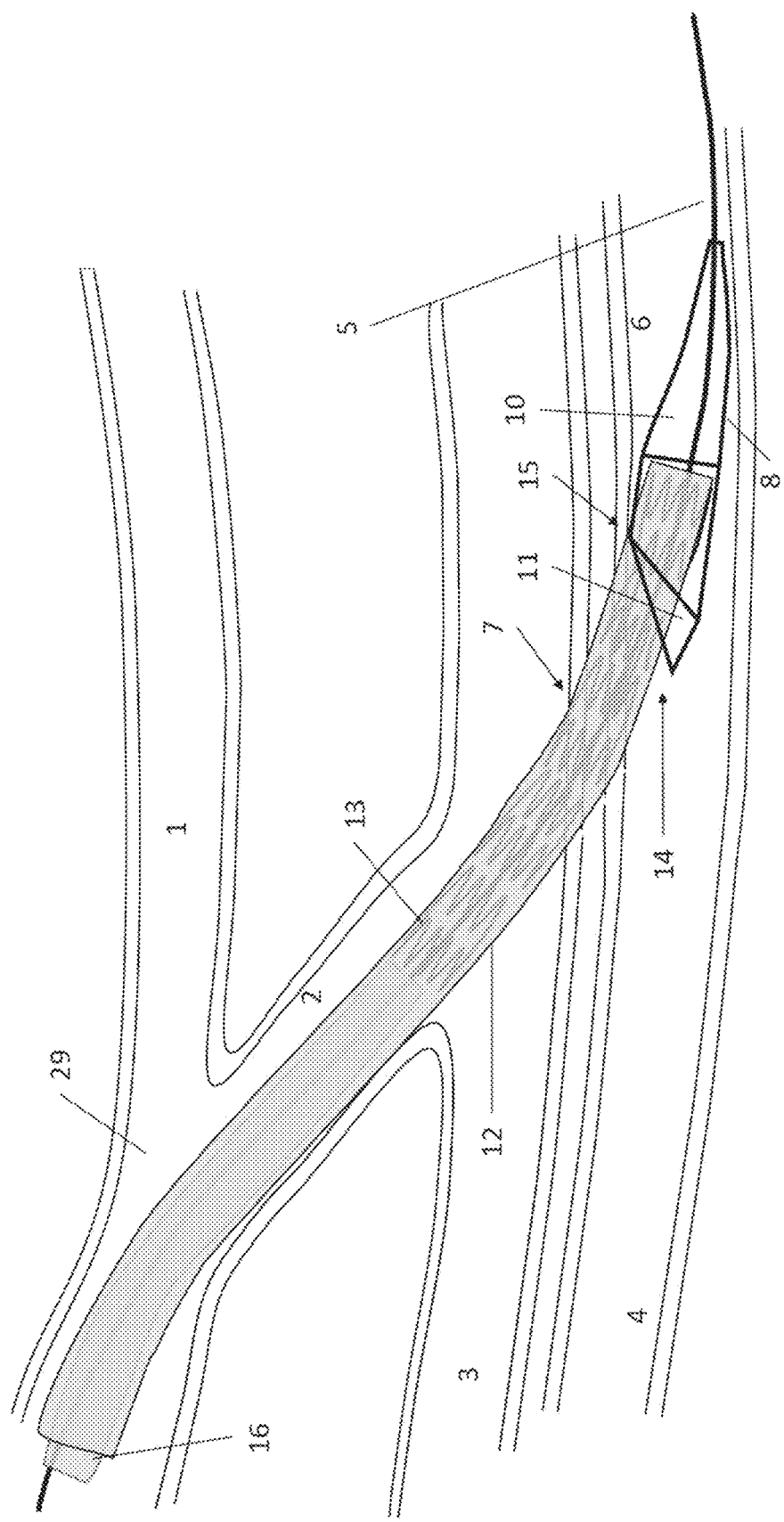

FIG. 4 depicts the nose cone 8 of delivery system 29 advanced across AVF location 7 and within deep artery 4. Middle shaft 16 is shown slidably disposed within outer sheath 12. Middle shaft 16 is slidably disposed around guidewire shaft 22 which is not shown in FIG. 4. Also depicted is gap 14 which may form when the delivery system 29 follows guidewire curvature 6 and the nose cone 8 and outer sheath 12 are no-longer coaxial. The gap 14 can be defined in some embodiments as an open space between the proximal opening of the nose cone 8 and a sidewall of the outer sheath 12 as it enters the proximal opening of the nose cone 8. In some embodiments, the gap defines about, at least about, or no more than about 5%, 10%, 15%, 20%, 25%, 30%, 35%, 40%, 45%, 50%, or more or less in length and/or diameter of the respective length and/or diameter of the proximal opening of the nose cone 8, or ranges including any two of the foregoing values. In some embodiments, no gap between the proximal opening of the nose cone 8 and a sidewall of the outer sheath 12 is formed and/or required.

Angle 15 between the central (e.g., longitudinal) axis of nose cone 8 and the central (e.g., longitudinal) axis of outer sheath 12 may form when the distal end of delivery system 29 is in a curved configuration where the proximal end of tapered proximal end 11 is on the outside of the curve as shown in FIG. 4. In some embodiments, the angle 15 can be, for example, about, at least about, or no more than about 5, 10, 15, 20, 25, 30, 35, 40, 45 degrees, or more or less, and ranges including any two of the foregoing values. To facilitate greater flexibility between nose cone 8 and outer sheath 12, nose cone 8 may have a slit in the wall that forms cavity 9. In some embodiments, the curvature of guidewire 5 may be used to form angle 15 and thus gap 14. Alternative means of forming angle 15 and gap 14 can be utilized. An alternative embodiment could be, for example, to use one, two, or more pull wires to deflect the distal end of delivery system 29 so that gap 14 is formed. A wide variety of steerable and/or deflectable elements can be utilized depending on the desired clinical result. In some cases, a gap 14 may be formed by a difference between an outer diameter of the outer sheath 12 and an inner diameter of the cavity 9 of the nose cone 8.

Figure 5:
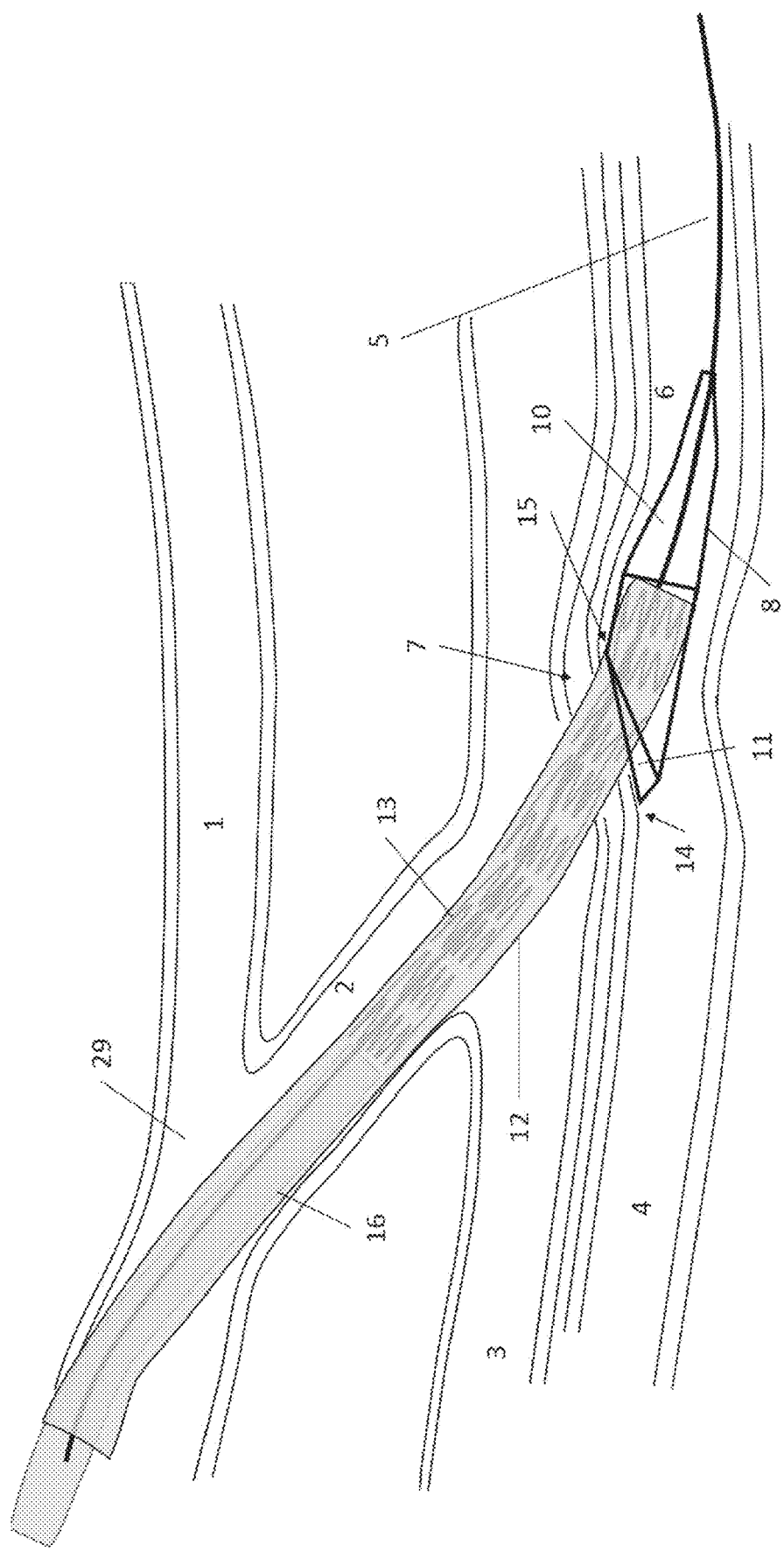

FIG. 5 depicts nose cone 8 engaging the near wall of deep artery 4 after delivery system 29 has been pulled proximally from its location in FIG. 4. The engagement between nose cone 8 and the near wall of deep artery 4 can be due to gap 14 which can be formed when delivery system 29 was urged into a curved configuration with proximal end of tapered proximal end 11 on the outside of the curvature. In some embodiments, the nose cone 8 can engage the near wall of the artery without a gap 14 required. For example, the proximal end of tapered proximal end 11 may engage the near wall of the artery 4 without a gap 14 between the tapered proximal end 11 and the outer sheath 12. Also depicted is the deformation of the anatomy at AVF location 7 which is a result of the apposition forces between the near wall of deep artery 4 and tapered proximal end 11 of nose cone 8. This deformation of the anatomy at AVF location 7 may be visualized by ultrasound and used to verify proper tissue engagement and/or implant placement before delivery.

Figure 6A:
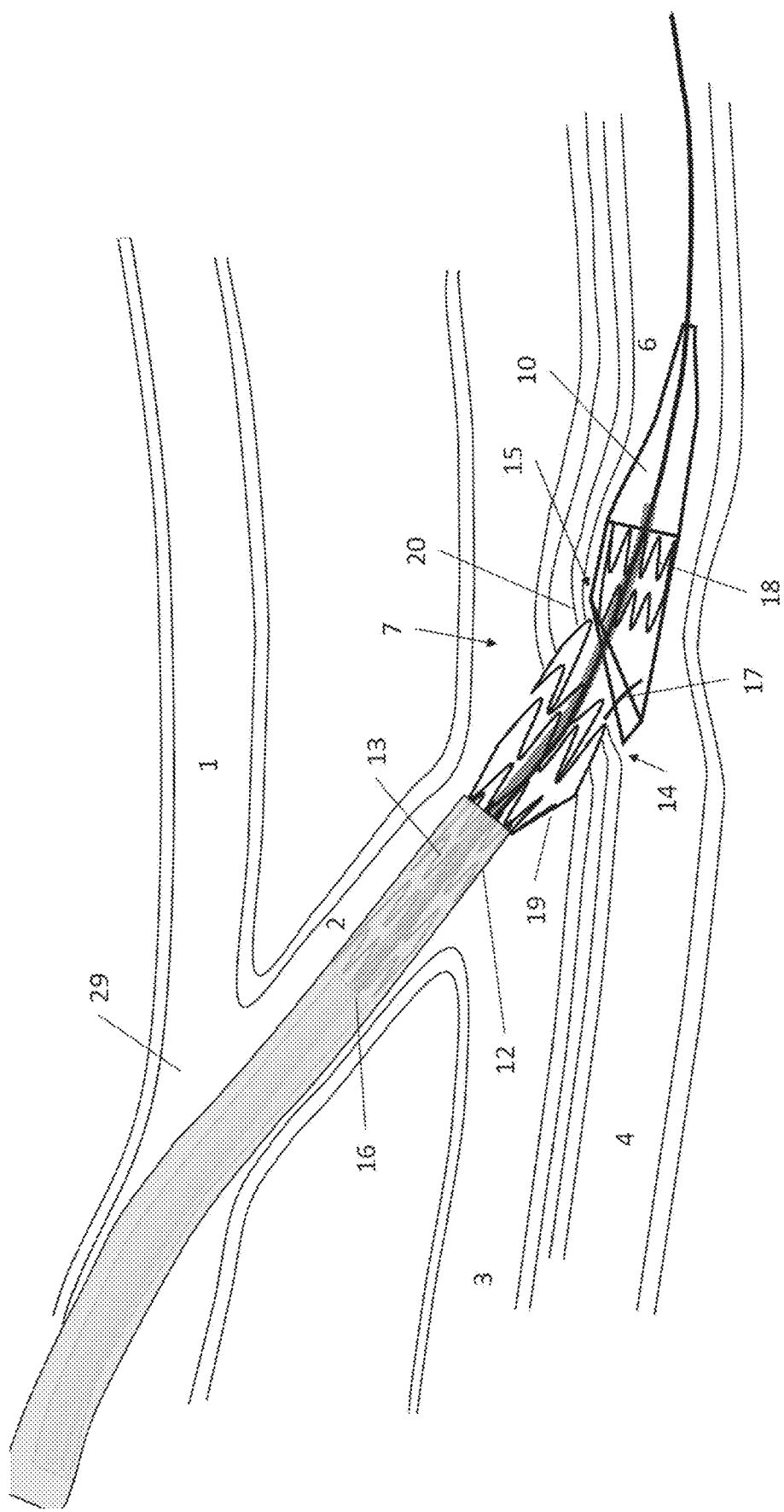
Figure 6B:
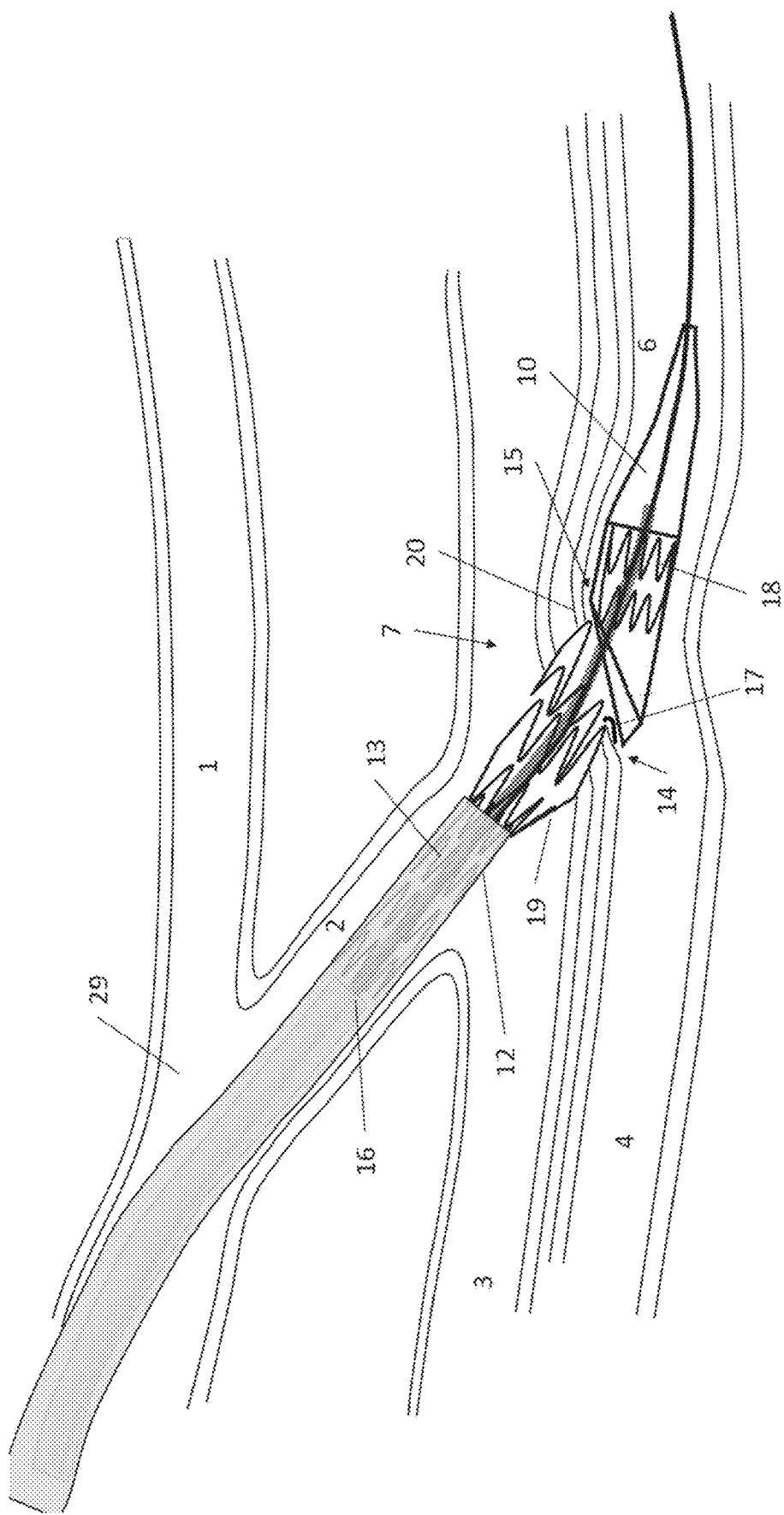

FIG. 6A depicts an initial step of the first stage of delivery of elastically constrained implant 13, according to some embodiments. While nose cone 8 is held in apposition against the near wall of deep artery 4, outer sheath 12 is retracted proximally so that the elastically constrained implant 13 is allowed to expand with the precise location defined due to the engagement between nosecone 8 and the near wall of deep artery 4. The distal end of middle shaft 16 is held fixed during delivery so that elastically constrained implant 13 does not slip proximally during the retraction of outer sheath 12. Also depicted is distal implant segment 18 being held partially constrained by cavity 9. Connector struts 20 that can be, for example, axially oriented as illustrated connect distal implant segment 18 to proximal implant segment 19 which has not yet been fully released in FIG. 6A. Also partially constrained in cavity 9 is one or more proximal anchors 17. Depicted in FIG. 6A is the radial expansion at AVF location 7 due to the radial stiffness of the elastically expanding implant 13. The distal end of proximal implant segment 19 may be angled with respect to an axis of the distal implant segment 18 of the implant so that it does not obstruct deep artery 4 while still fully within and supporting the area between the vascular walls of deep vein 3 and deep artery 4. In some embodiments, the distal end of proximal implant segment 19 may be at an angle of between about 0 degrees to about 90 degrees with respect to the axis of the distal implant segment 18. In some embodiments, and as shown in FIG. 6B, retraction of outer sheath 12 proximally may release one or more proximal anchors 17. Proximal anchor(s) 17 may engage the near wall of deep artery 4 (as shown in FIG. 6B), a wall of deep vein 3, a wall of perforator vein 2, a wall of superficial vein 1, and/or the or any interstitial tissues.

Figure 7A:
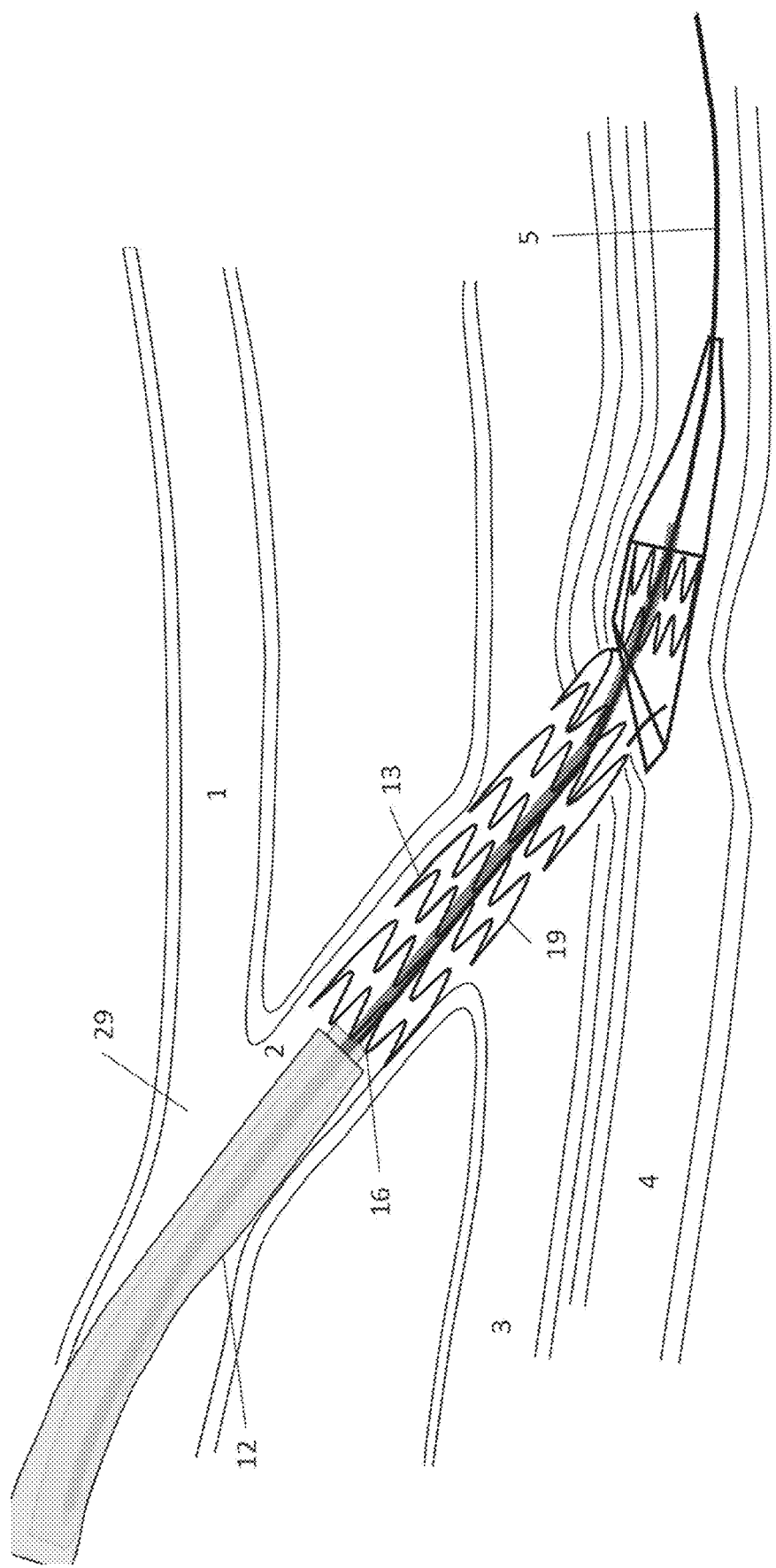
Figure 7B:
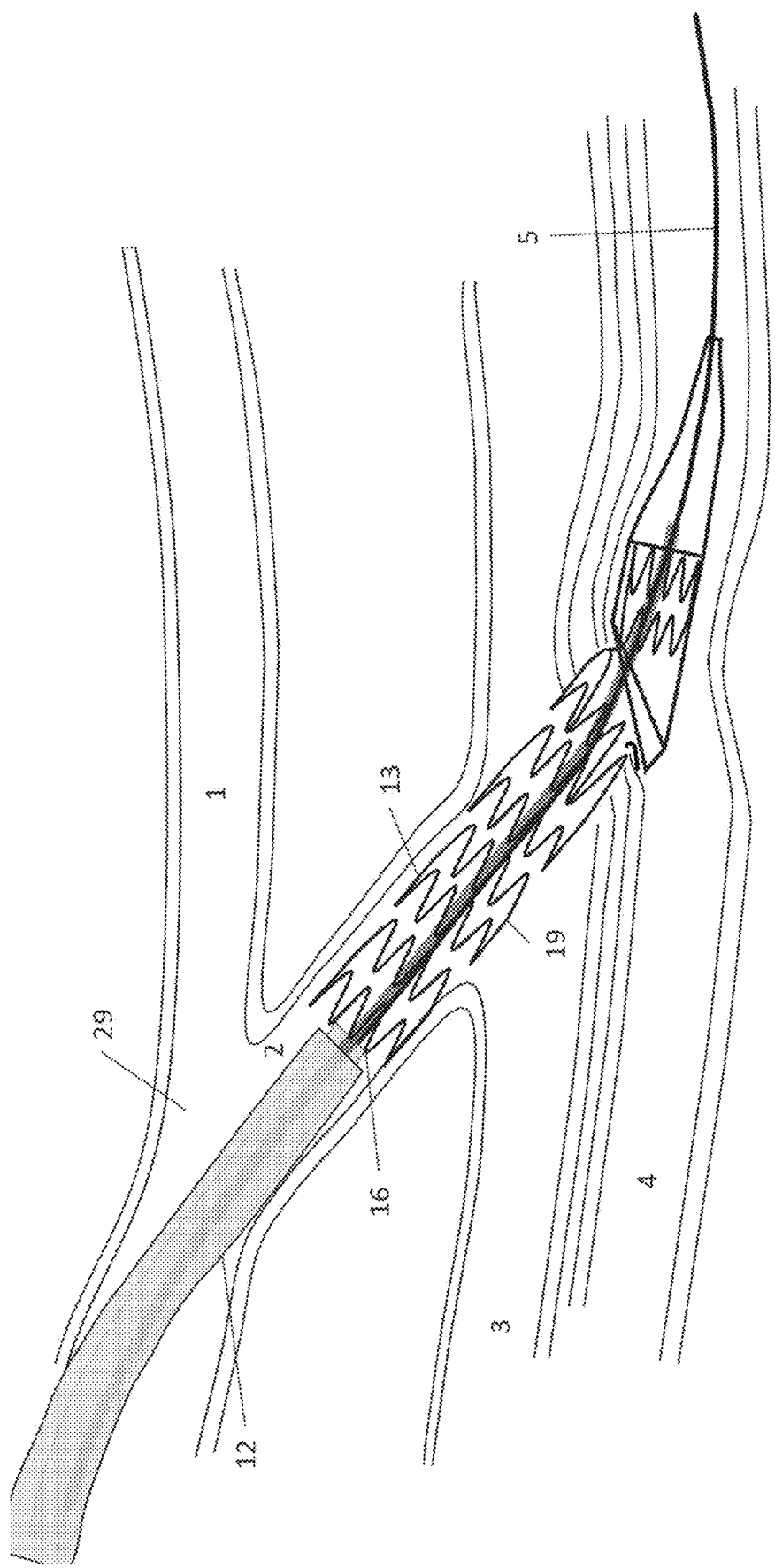

FIG. 7A follows from FIG. 6A and depicts continuing delivery of elastically constrained implant 13 with the further retraction of outer sheath 12 until proximal implant segment 19 is fully released from outer sheath 12. FIG. 7B follows from FIG. 6B and depicts continuing delivery of elastically constrained implant 13 with the further retraction of outer sheath 12 until proximal implant segment 19 is fully released from outer sheath 12.

FIG. 8 depicts the delivery of distal implant segment 18 of implant 13 and, in some embodiments, the release of proximal anchor(s) 17. When nose cone 8 is advanced distally by advancing guidewire shaft 22 distally, distal implant segment 18 is held in its axial position by connector struts 20 and thus is slidably released from cavity 9. In some embodiments, proximal anchor(s) 17, which may be shaped into, for example, a hook configuration, may also be elastically released from cavity 9 with advancement of nose cone 8 and assume their hook shape to secure the most proximal portion of the distal edge of proximal implant segment 19 to the near wall of deep artery 4. In some embodiments, proximal anchor(s) 17 may be released upon retraction of outer sheath 12 proximally and upon nose cone 8 advancement distally. In alternative embodiments, there are no proximal anchor(s) 17 due to sufficient anchoring provided by the apposition between the struts of implant 13 and the surrounding anatomy. In the embodiment shown, distal implant segment 18 provides a means of securing the most distal portion of the distal edge of proximal implant segment 19 so that it does not encroach into the luminal space of deep artery 4. Distal implant segment 18 can also provide radial support for deep artery 4 to ensure patency and sufficient distal blood flow after implantation of the implant 13. Distal implant segment 18 can be sized to be accommodated by the deep artery 4. In some embodiments, the diameter of distal implant segment 18 is 0-50% larger than the deep artery 4. In other embodiments, the diameter of distal implant segment 18 is 5-25% larger than the deep artery 4. In some embodiments, the proximal implant segment 19 has a diameter of between about 2 mm to about 7 mm. In some embodiments, the distal implant segment 18 has a diameter of between about 2 mm to about 7 mm. In some embodiments, the proximal implant segment 19 and the distal implant segment 18 may have about the same diameter. In some embodiments, the proximal implant segment 19 and the distal implant segment 18 may have different diameters. In some embodiments, the proximal implant segment 19 has a diameter of about 5 mm and the distal implant segment 18 has a diameter of about 4 mm. In some embodiments, the proximal implant segment 19 and/or the distal implant segment 18 may not be circular in cross-sectional shape, and thus they may instead have cross-sectional areas and/or perimeters that can be the same or different. In some embodiments, there is no distal implant segment 18 portion of implant 13. In some embodiments, there is no distal implant segment 18 portion of implant 13 and the distal end of proximal implant segment 19 may comprise a continuous strut and/or ring, which may also be referred to as an anastomotic ring. In some embodiments, there is no distal implant segment 18 portion of implant 13 and the distal end of proximal implant segment 19 may comprise a continuous strut and/or ring with a skirt and/or flange that extends into the deep artery 4 and seals against the near wall of deep artery 4 upon deployment.

Figure 9:
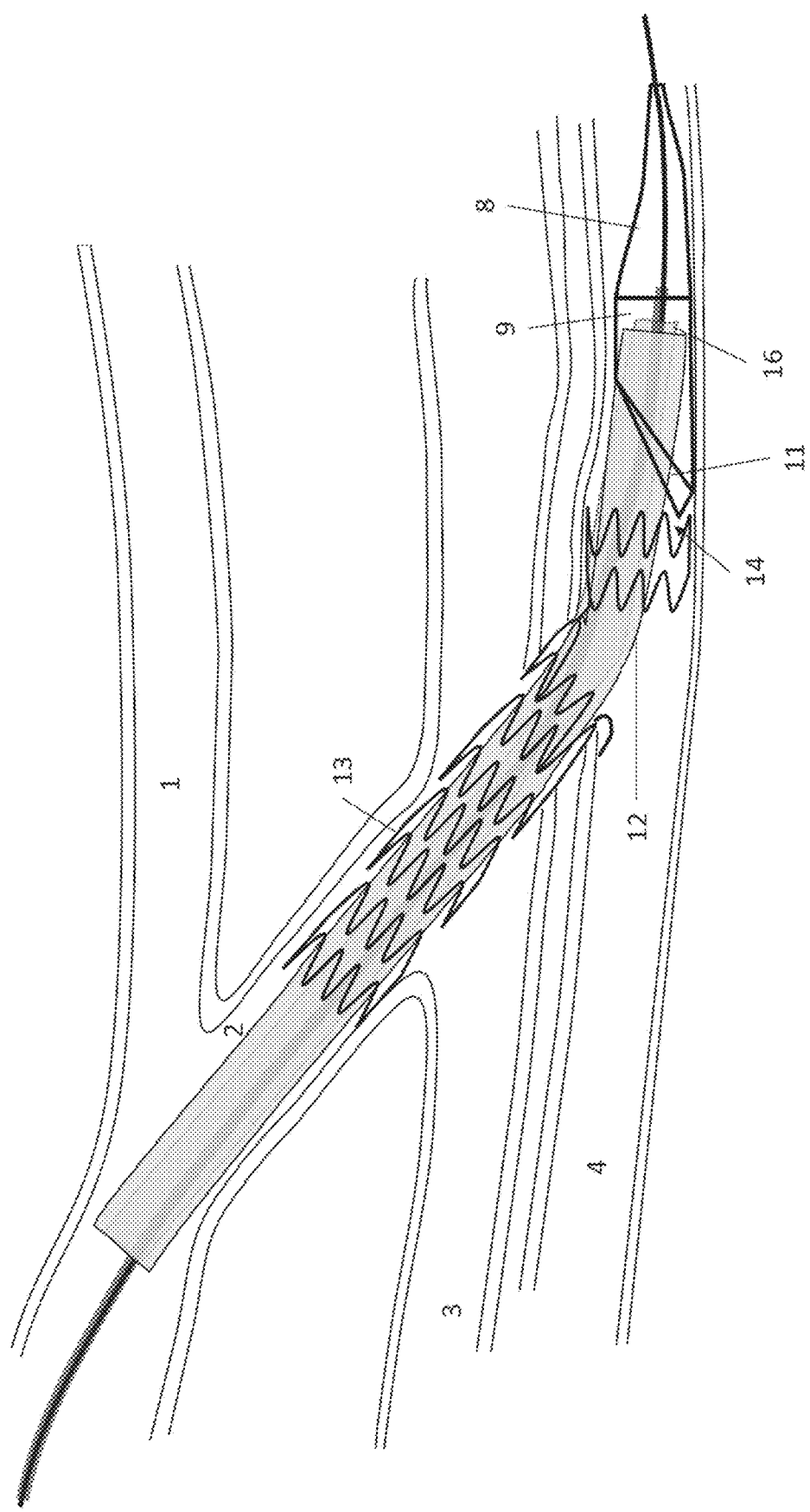

FIG. 9 depicts the initial step of removal of delivery system 29 with the advancement of outer sheath 12 and middle shaft 16 distally through the delivered implant 13 and into cavity 9, according to some embodiments. In some embodiments, middle shaft 16 leads outer sheath 12 during this advancement step to facilitate reliable engagement of outer sheath 12 into cavity 9 without outer sheath 12 catching the proximal end 11 of distal nose cone 8.

Figure 10A:
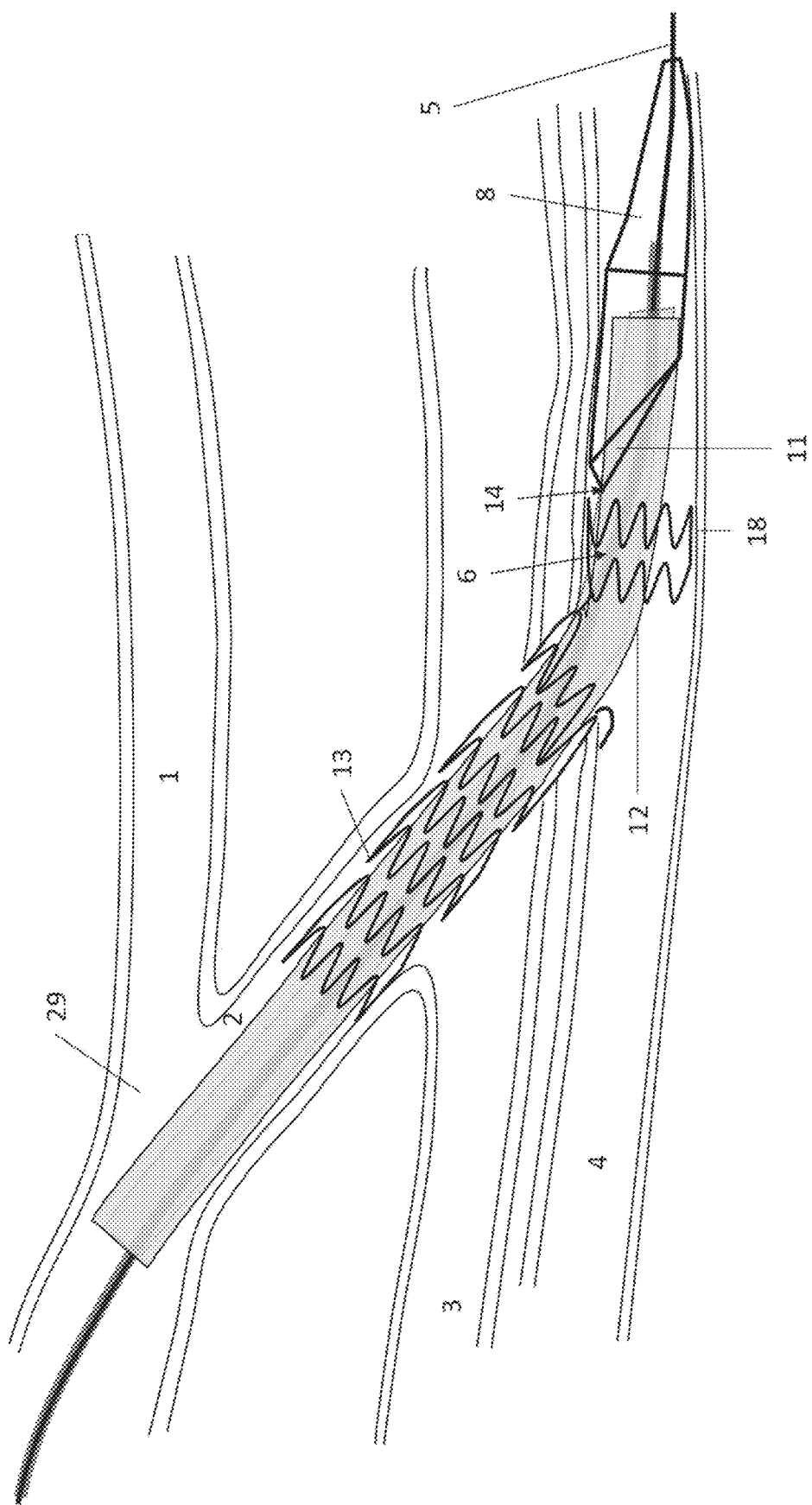

FIG. 10A depicts a continuation of the removal of delivery system 29 with the rotation of delivery system 29 around its axis of, e.g., approximately 180 degrees such that the proximal portion of tapered proximal end 11 of nose cone 8 is on the inside of curvature 6. In this orientation, gap 14 is minimized, eliminated, or substantially eliminated and there is flush contact between proximal tapered end 11 and outer sheath 12. This low-profile configuration facilitates removal of nose cone 8 without engagement of delivered implant 13 or any of the anatomical features near AVF location 7.

Figure 10B:
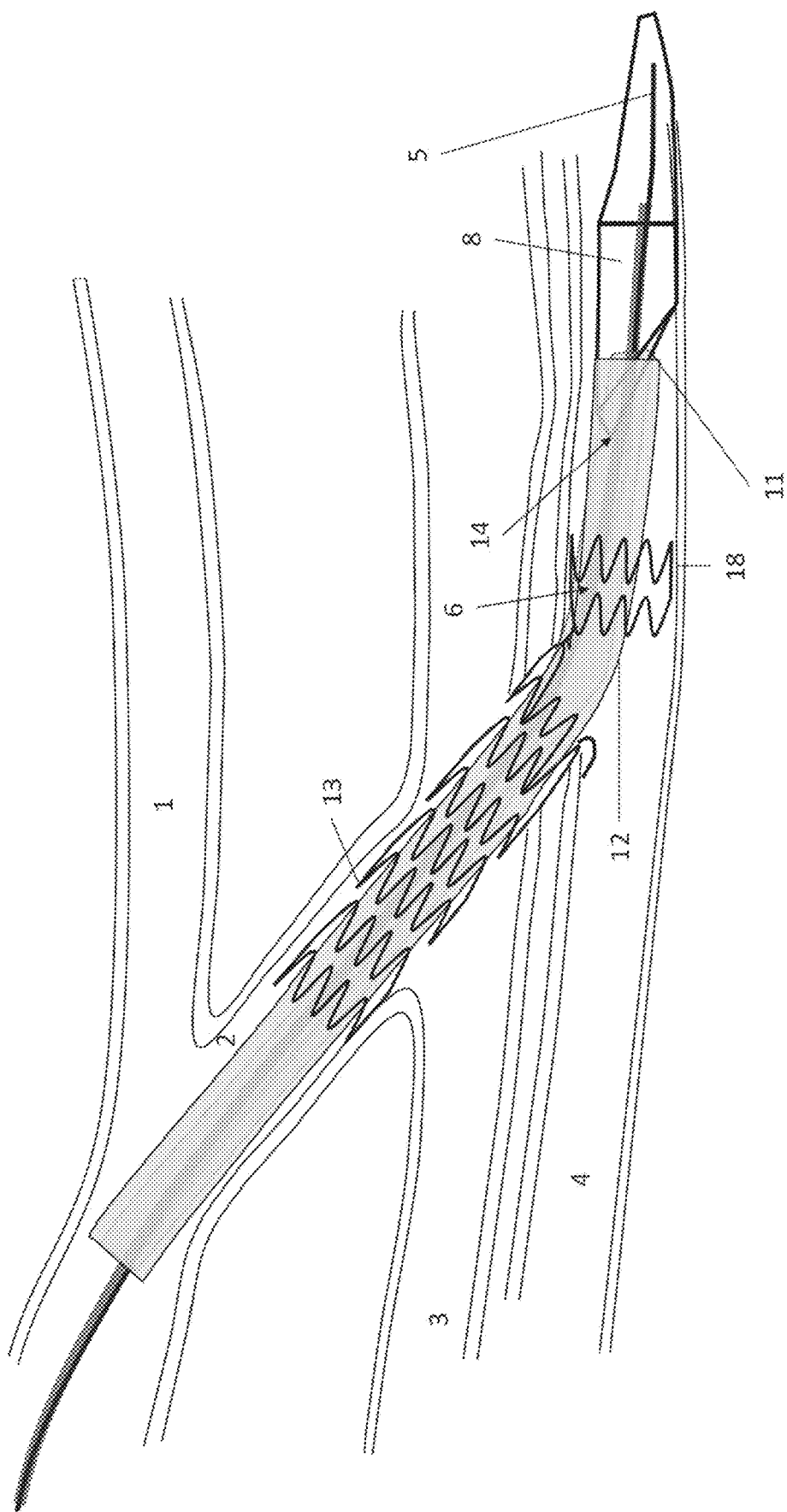

FIG. 10B depicts an alternative embodiment for providing a low-profile removal configuration for delivery system 29. In this embodiment, prior to advancing outer sheath 12 through implant 13, nose cone 8 is rotated, e.g., approximately 180 degrees around its axis. After rotation of nose cone 8, outer sheath 12 is advanced through implant 13 until it engages with the proximal end of tapered proximal end 11. Due to the tapered structure of tapered proximal end 11, it may enter the inner diameter of outer sheath 12 when outer sheath 12 is advanced. In this configuration, there are no structures on delivery system 29 that can interfere with its removal from the body. To complete removal in this embodiment, the delivery system is retracted while maintaining the overlap of outer sheath 12 over nose cone 8 until it exits the body.

Figure 11:
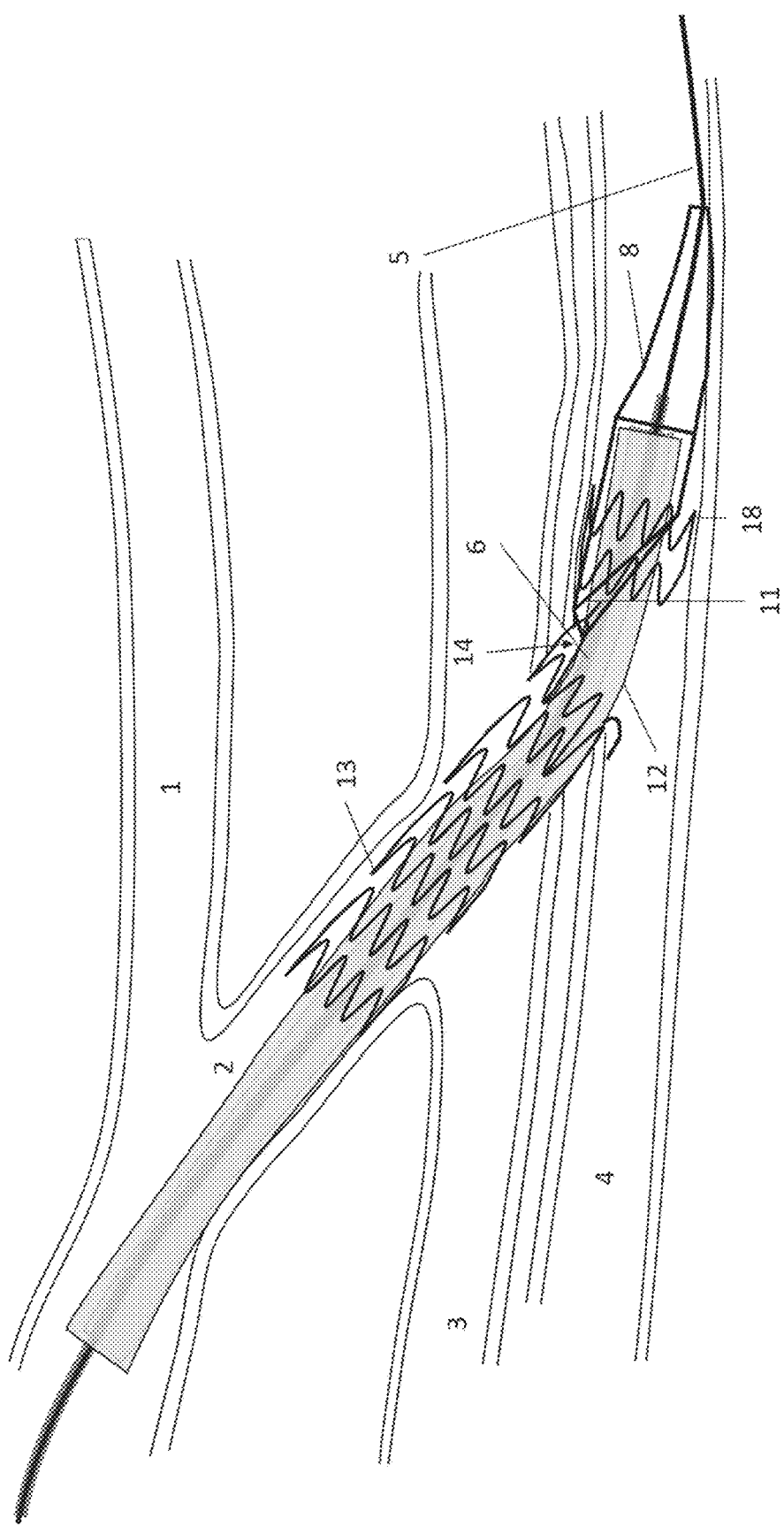

FIG. 11 depicts continuing of the removal of delivery system 29 in the configuration depicted in FIG. 10A. The tapered proximal end has entered within delivered distal implant segment 18 without interference due to the low-profile configuration. A preferred embodiment is where implant 13 has an unconstrained delivered internal dimension which is greater than the outer dimension of nose cone 8 so that nose cone 8 does not experience excessive resistance or interference with implant 13 upon removal through implant 13.

Figure 12:
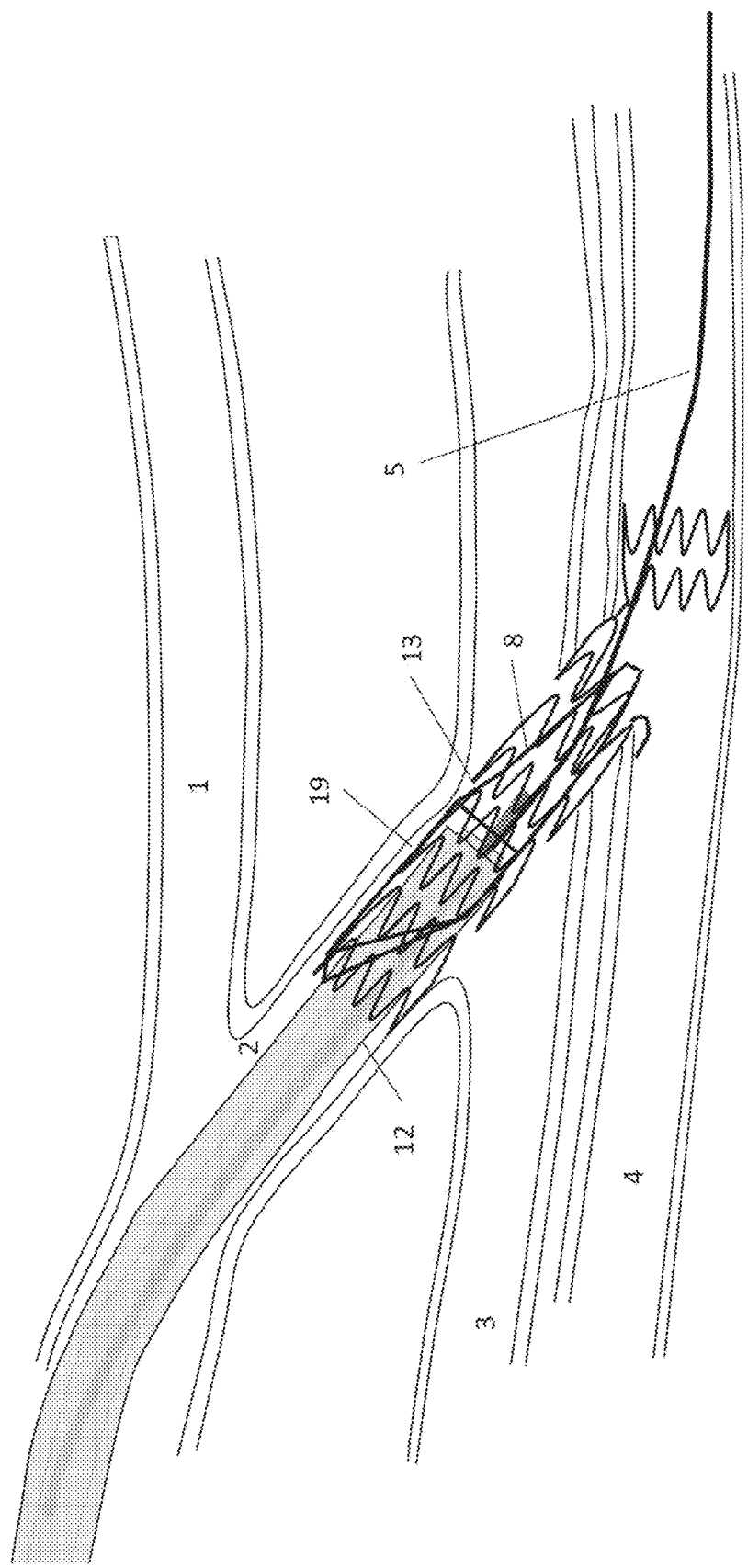

FIG. 12 depicts a further continuation of the removal of delivery system 29. Delivery system 29 has been further retracted and nose cone 8 has travelled partway through proximal implant segment 19 of implant 13.

Figure 13:
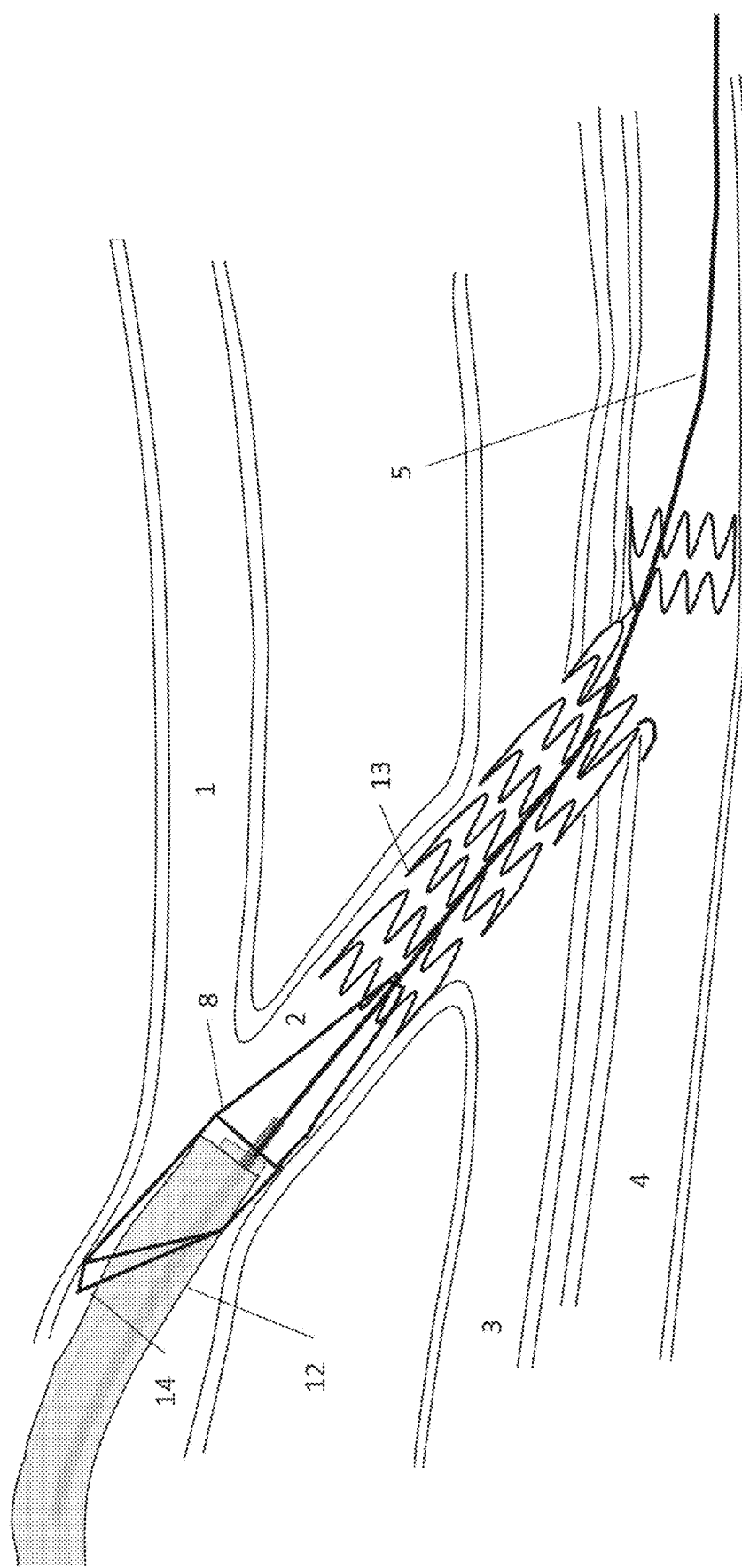

FIG. 13 depicts a continuation of the removal of delivery system 29. Delivery system 29 has been retracted completely through implant 13. Due to the curvature of the anatomy at this location, gap 14 may be formed again. If gap 14 causes undue resistance to the continuation of the removal of delivery system 29 from the body, delivery system 29 can be rotated once again to minimize and/or eliminate gap 14 and allow for minimal resistance to delivery system 29 removal.

Figure 14:
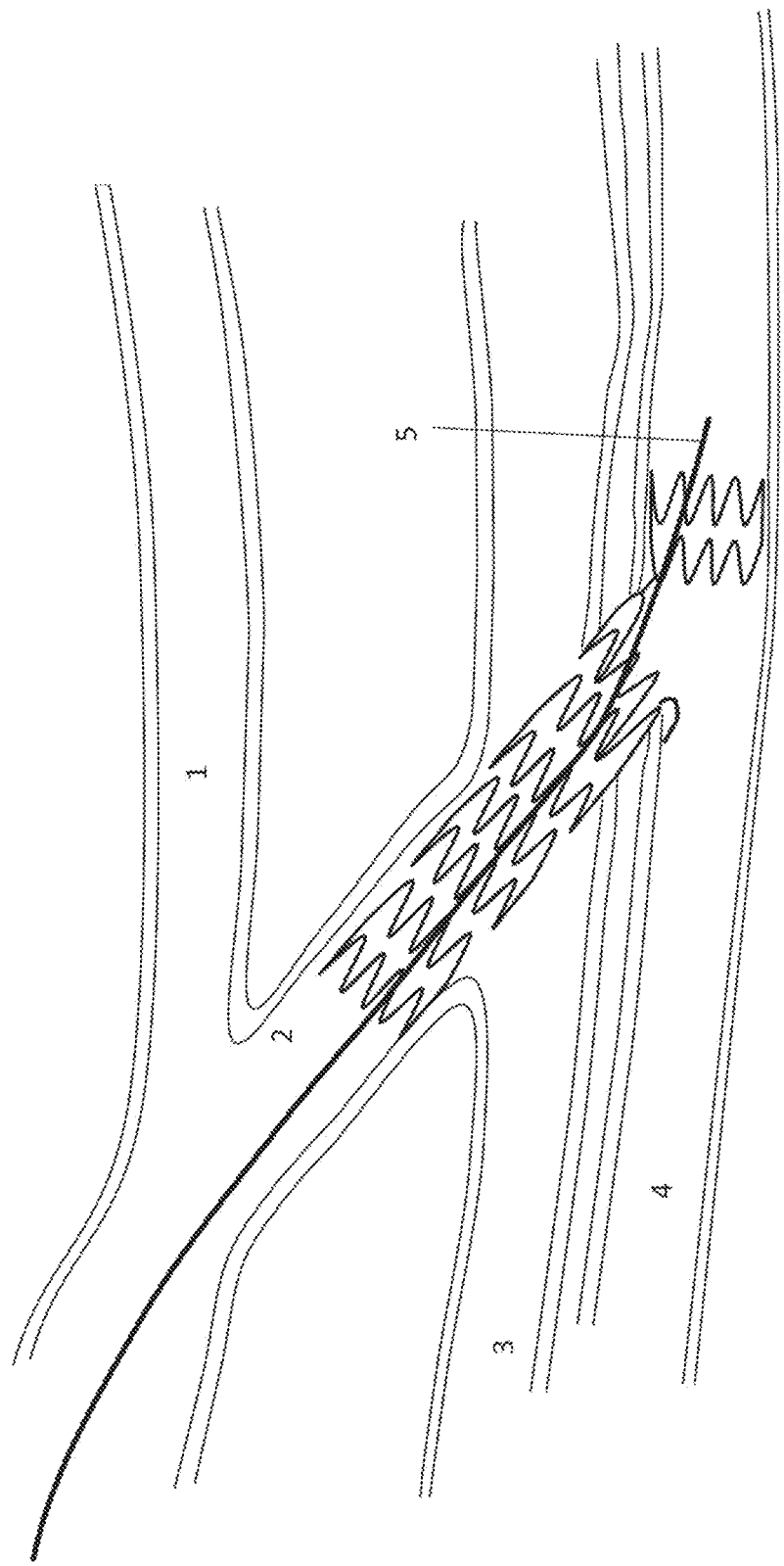

FIG. 14 depicts the initiation of removal of guide wire 5 from the body. Prior to removal of guidewire 5, it may be desirable or advantageous to advance a balloon dilatation catheter appropriately sized for implant 13 and the vasculature to facilitate complete expansion of implant 13. In some embodiments with a proximal implant segment 19 and a distal implant segment 18 of different diameters, cross-sectional areas, and/or perimeters, balloon dilation catheters of different sizes may be used to facilitate complete expansion of the proximal implant segment 19 and the distal implant segment 18.

Figure 15:
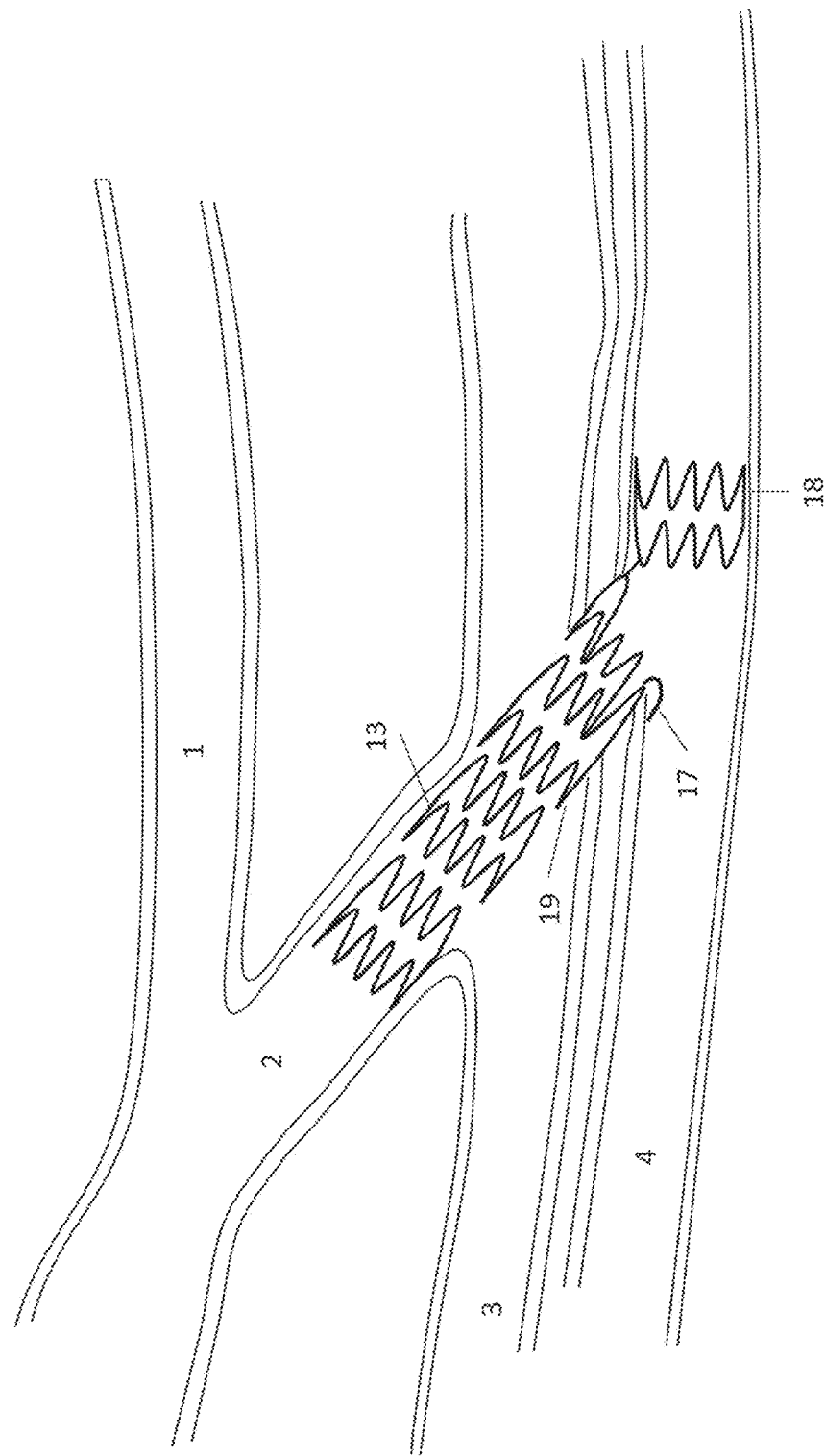

FIG. 15 depicts the completed delivery of implant 13 with distal implant segment 18 in deep artery 4 and proximal segment 19 forming an AVF between deep vein 3 and deep artery 4. In this embodiment implant 13 is at least partially anchored in place with proximal anchor(s) 17 and distal implant 18. Alternative anchoring features such as barbs may also be used with some embodiments. In a preferred embodiment, implant 13 is covered or encapsulated with a biocompatible graft material such as, for example, ePTFE which can facilitate endovascular healing while minimizing stenosis of the lumen due to hyperplasia. In some embodiments, the graft material encapsulation can be constructed with a lamination of an inner layer of porous graft material, such as ePTFE, covering the inner surface of implant 13 and an outer layer of porous graft material, such as ePTFE, covering the outer surface of implant 13 that have been bonded together. In some embodiments, the bonding of the inner layer and outer layer of porous graft material encapsulates the struts of implant 13 and may be accomplished by fusing the outer and inner layers together with heat and compression. In other embodiments, a laminating layer of thermoplastic, such as fluorinated ethylene propylene (FEP) film, Polyethelyne (PE), or thermoplastic polyurethane film (TPU), may be placed between the inner and outer layer of porous graft material to facilitate the bonding. In some embodiments, the thermoplastic laminating layer may be porous and in other embodiments the laminating layer may be non-porous. In some embodiments, the porosity of the encapsulated implant 13 may be maintained by wrapping a strip of non-porous thermoplastic laminating layer in a helical fashion between the inner and outer layer of porous graft material and leaving gaps between each wrap of the thermoplastic laminating layer. In some embodiments, no gaps are left between each wrap of the thermoplastic laminating layer, leaving the final assembly non-porous, but with a porous surface. Covering or encapsulating proximal implant segment 19 with a graft material may prevent infiltration of blood into the or any interstitial tissues between deep vein 3 and deep artery 4 which may cause hematomas, infections and other complications. Covering proximal implant segment 19 with a graft material may also help divert blood flow from deep artery 4 into superficial vein 1.

Figure 16B:
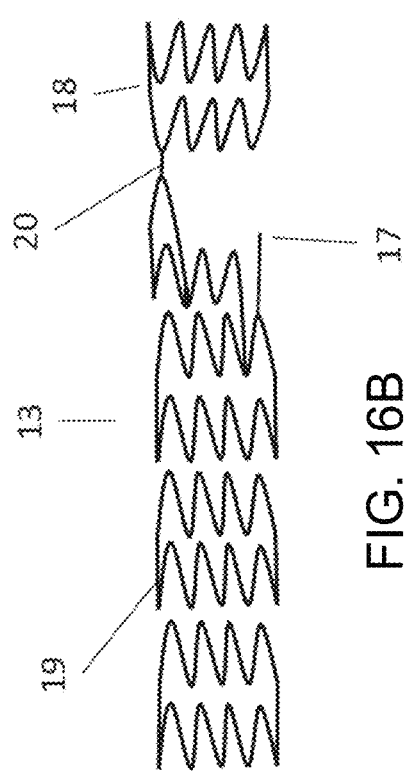
FIGS. 16A-16C depict an endovascular implant according to some embodiments.
Figure 16C:
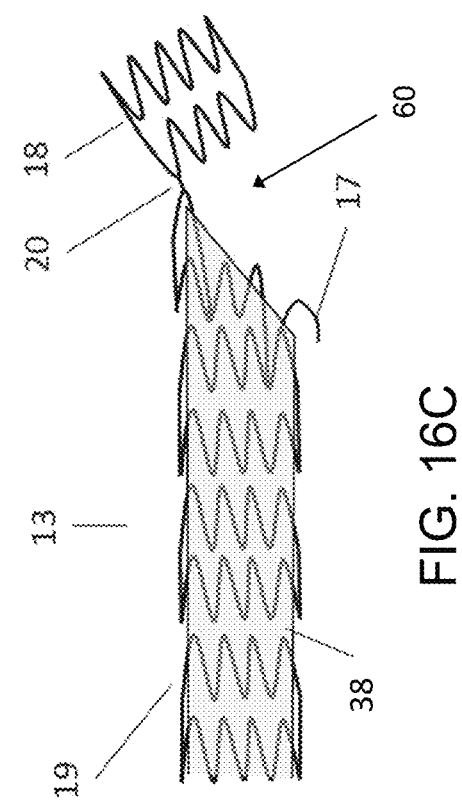
Figure 16A:
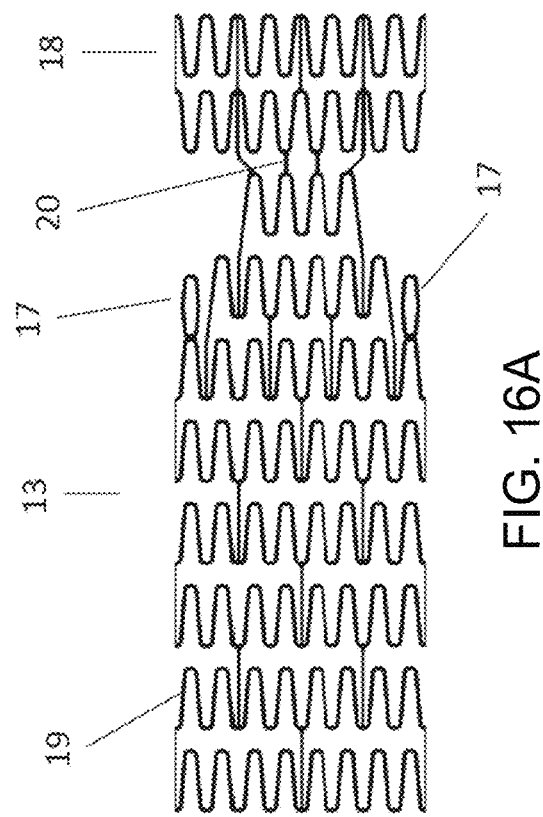

FIGS. 16A, 16B and 16C depict an embodiment of implant 13. FIG. 16A depicts a pattern that is intended to be cut from superelastic tubing, such as superelastic NiTi tubing, to form the features of implant 13. The sections of the cut pattern that form proximal implant segment 19, distal implant segment 18, proximal anchor(s) 17 and connector struts 20 are shown. In some embodiments, implant 13 may alternatively be made of superelastic wire or formed from rolling cut superelastic sheet stock. FIG. 16B depicts the shape of implant 13 after the pattern in FIG. 16A has been cut out of a tube. FIG. 16C depicts implant 13 with distal implant segment 18, proximal implant segment 19 and connector struts 20 after it has been shape-set from superelastic tubing, such as superelastic NiTi tubing, using techniques that are well known. Also depicted in FIG. 16C is a graft material 38 covering the inner diameter of proximal segment 19. Graft material 38 may be used to cover the inner diameter or outer diameter or both the inner and outer diameter of any portion (e.g., its entirety or less than its entirety) of implant 13 depending on the specific needs for the application. Expanded Polytetrafluoroethylene, also known as ePTFE has been shown to be an advantageous graft covering for endovascular implants. Other materials such as polyester mesh may also be suitable for certain embodiments. Implant 13 may be covered or encapsulated with a biocompatible graft material as described elsewhere herein. In some embodiments, the proximal implant segment 19 may comprise an elongate tubular member or body with a proximal end, a distal end, and a flow path therethrough. In some embodiments, the distal implant segment 18 may comprise an elongate tubular member or body with a proximal end, a distal end, and a flow path therethrough. In some embodiments, the distal implant segment 18 may be positioned downstream of the location of the distal end of the proximal implant segment 19 (e.g., downstream in regard to the direction of arterial blood flow). In some embodiments, implant 13 may not have proximal segments, distal segments, and/or anchoring features, and may have more basic structures that simply require accurate placement within the body. In some embodiments, anchoring features of implant 13, such as proximal anchor(s) 17, may form an angle relative to the body of the implant 13 of between about 10 degrees to about 90 degrees. In some embodiments, anchoring features of implant 13, such as proximal anchor(s) 17, may form an angle relative to the body of the implant 13 of between about 35 degrees to about 40 degrees. Implant 13 may also be made from bioresorbable materials such as PLA, PGA, PLLA or other suitable materials for a specific application. Implant 13 may also be coated on its internal surface, external/outer surface, or both internal and external/outer surface, with heparin and/or therapeutic agents, including drugs and compounds that are well known to reduce intimal hyperplasia and/or vascular stenosis in endovascular implant applications. In some embodiments, implant 13 according to FIGS. 16A-16C may be only partially covered or encapsulated with a biocompatible graft material 38, include a laminating layer and/or a coating, for example, only proximal implant segment 19 may be covered/encapsulated with a biocompatible graft material, have a laminating layer, and be coated.

Figure 17A:
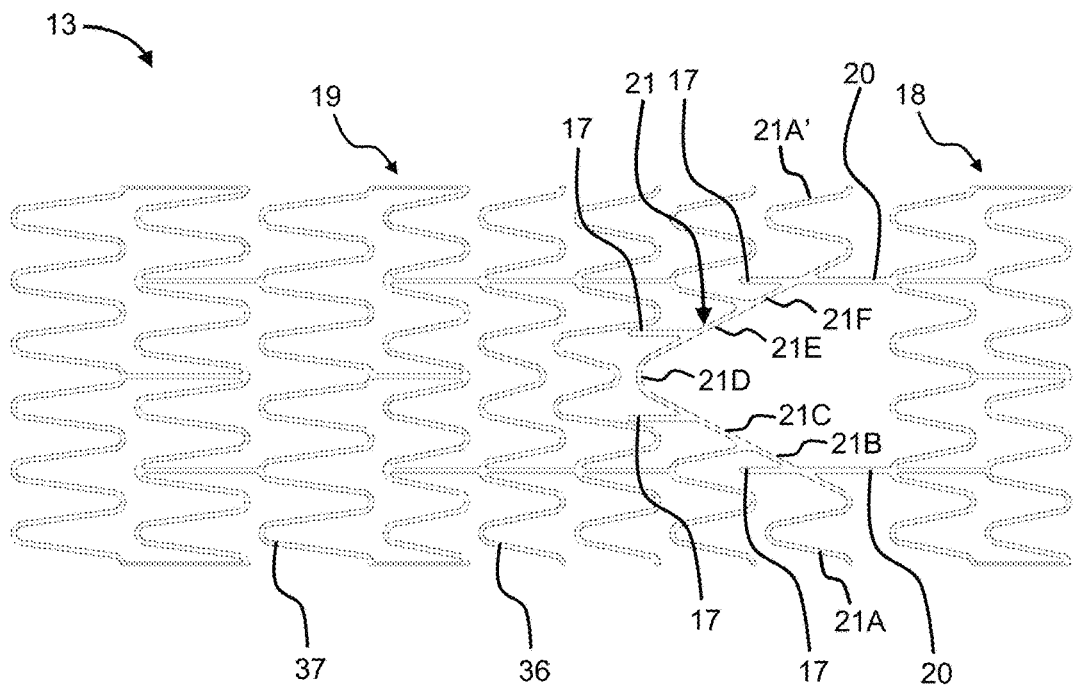
FIGS. 17A-17I depict an endovascular implant according to some embodiments.
Figure 17B:
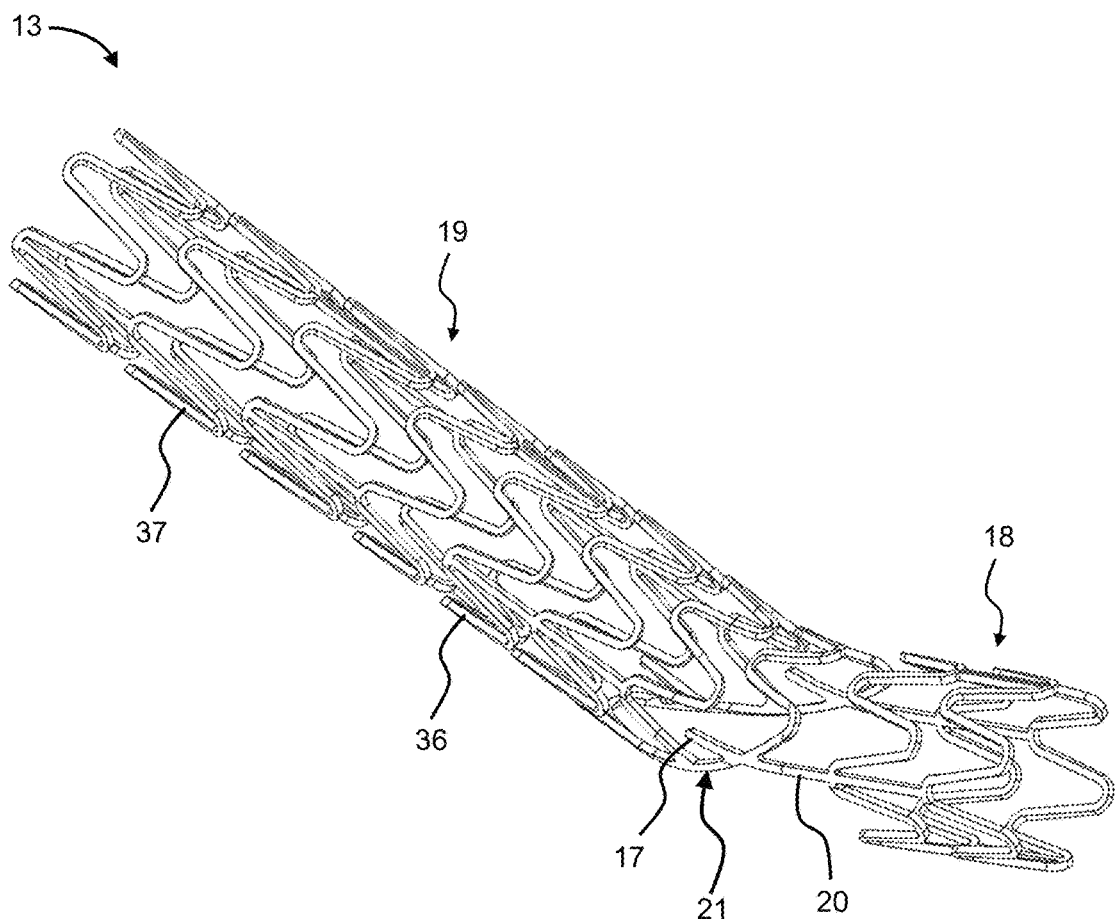
Figure 17C:
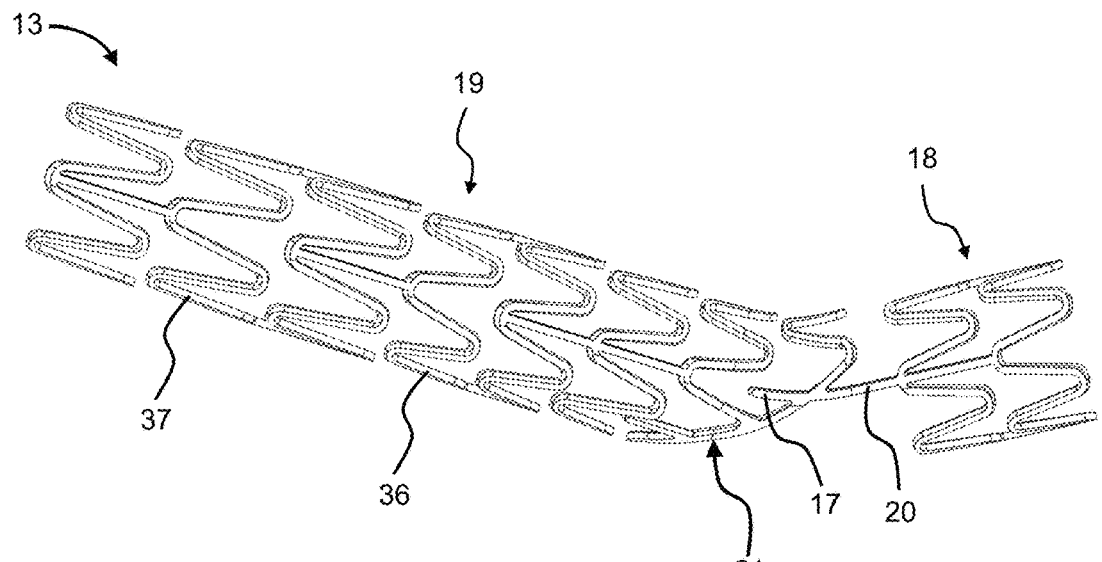
Figure 17D:
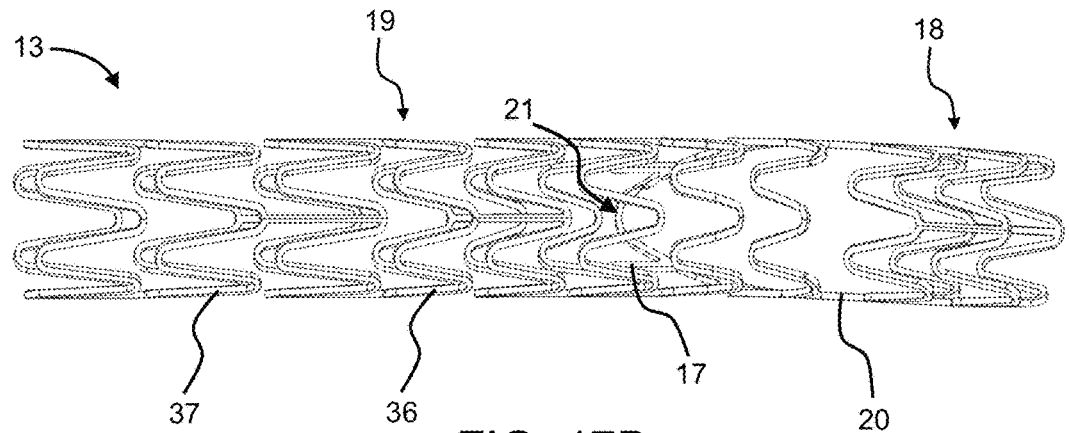
Figure 17E:
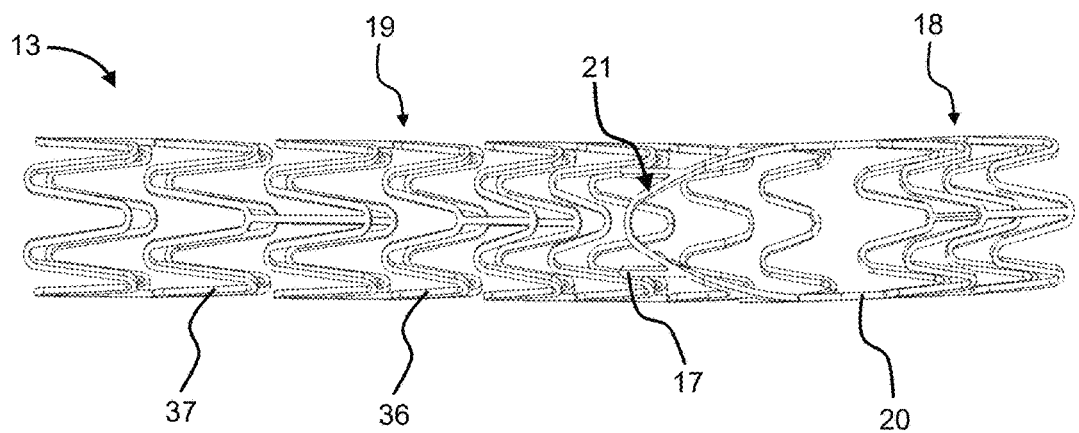
Figure 17F:
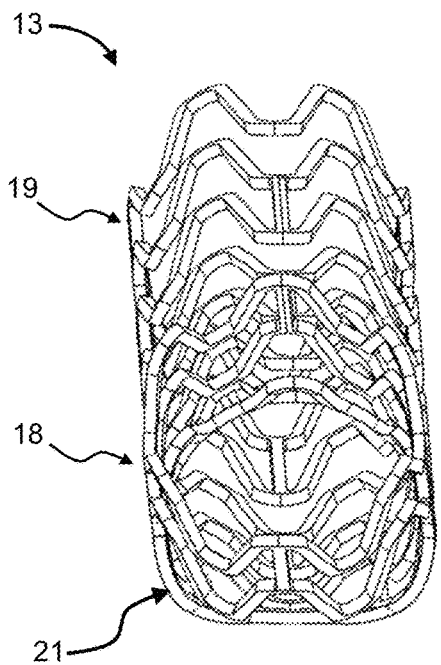
Figure 17G:
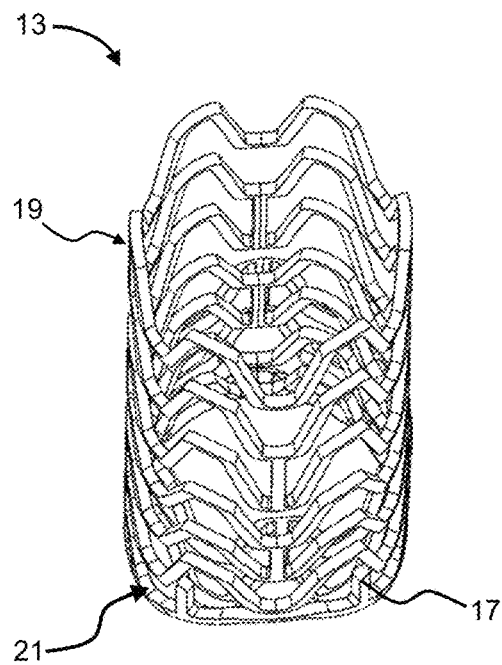
Figure 17H:
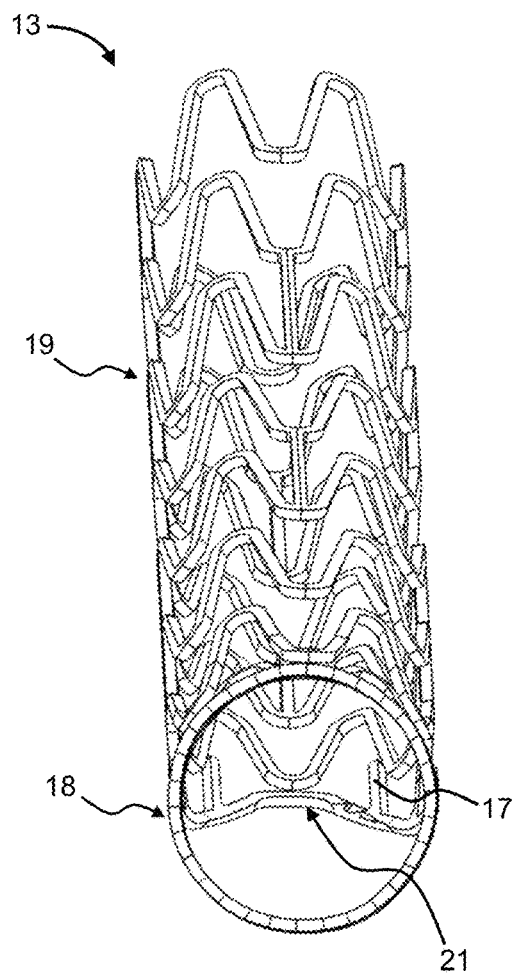
Figure 17I:
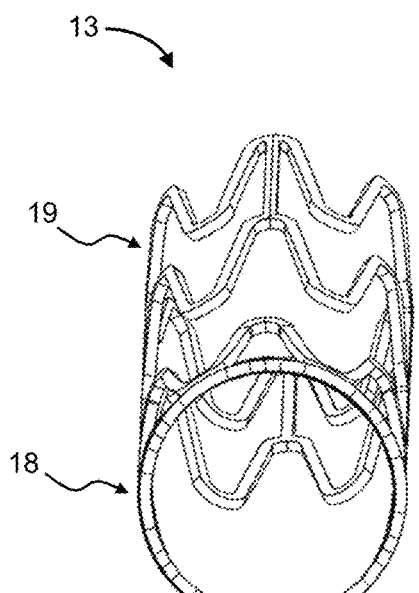

FIGS. 17A-17I depict an embodiment of implant 13. FIG. 17A depicts a pattern that is intended to be cut from superelastic tubing, such as superelastic NiTi tubing, to form the features of implant 13. The sections of the cut pattern that form proximal implant segment 19, distal implant segment 18, and connector struts 20 that connect the proximal implant segment 19 to the distal implant segment 18 are shown. In some embodiments implant 13 comprises proximal anchor(s) 17 as additionally shown in the cut pattern. In some embodiments, the proximal implant segment 19 may comprise an elongate tubular member or body with a proximal end, a distal end, and a flow path therethrough. In some embodiments, the distal implant segment 18 may comprise an elongate tubular member or body with a proximal end, a distal end, and a flow path therethrough. In some embodiments, the distal implant segment 18 may be positioned downstream of the location of the distal end of the proximal implant segment 19 (e.g., downstream in regard to the direction of arterial blood flow). In some embodiments implant 13 comprises a continuous strut/ring 21 (also referred to as an anastomotic ring) at the distal edge of proximal implant segment 19 as additionally shown in the cut pattern (e.g., at the distal edge of the distal end of the proximal implant segment 19). As shown in FIG. 17A, continuous strut/ring 21 may comprise strut elements 21A, 21B, 21C, 21D, 21E, 21F, and 21A', wherein strut elements 21A and 21A' are continuous with one another (i.e., they are shown separate in FIG. 17A because it is a cut pattern; when cut into tubing, strut elements 21A and 21A' are continuous with one another). In some embodiments, a continuous strut/ring 21 may provide a continuous distal edge to the proximal implant segment 19 to reduce wrinkles in an encapsulating graft material. In some embodiments, a continuous strut/ring 21 may provide a continuous distal edge to the proximal implant segment 19 to improve sealing of the implant 13 at the inner wall of deep artery 4. In some embodiments, a continuous strut/ring 21 may increase the radial stiffness of the distal edge of the proximal implant segment 19 to help maintain a fistula diameter and/or cross-sectional area (e.g., increased radial stiffness may lead to increased radial expansion of the fistula). In some embodiments proximal implant segment 19 may comprise struts of different lengths, and additionally shown are the sections of the cut pattern that form struts 36 of a shorter length and struts 37 of a longer length. In some embodiments, in addition to being longer, struts 37 may have a greater thickness/width than struts 36. In some embodiments, the location of the longer and/or thicker/wider struts 37 may allow for a larger diameter and/or cross-sectional area of the implant 13 to be formed relative to the diameter and/or cross-sectional area of implant 13 where struts 36 are located. In some embodiments, the location of the longer and/or thicker/wider struts 37 may allow for an increased radial stiffness of the implant 13 relative to the radial stiffness of implant 13 where struts 36 are located. In some cases, thinner struts may used to reduce the radial stiffness of the implant where located. Sometimes, longer struts may decrease the radial stiffness of the implant where located. In some embodiments, the distal and/or proximal ends of the proximal and/or distal implant segments may comprise a reduced radial stiffness compared to a radial stiffness along their axial lengths (e.g., to reduce mechanical stress concentrations at the vessel/implant interface). In some embodiments, implant 13 may alternatively be made of superelastic wire or formed from rolling cut superelastic sheet stock. FIG. 17B depicts a perspective view, FIG. 17C depicts a side view, FIG. 17D depicts a top view, and FIG. 17E depicts a bottom view of implant 13 with distal implant segment 18, proximal implant segment 19, connector struts 20, proximal anchor(s) 17, continuous strut/ring 21, shorter struts 36, and longer struts 37 after it has been cut in superelastic tubing, such as NiTi tubing, from the pattern of FIG. 17A and shape-set. FIG. 17F depicts a front (distal end) view, FIG. 17G depicts a back (proximal end) view, FIG. 17H depicts a front (distal end) view through a longitudinal axis of distal implant segment 18, and FIG. 17I a back (proximal end) view through a longitudinal axis of proximal implant segment 19 of implant 13 with some of the various features identified in FIGS. 17A-17E after it has been cut in superelastic tubing, such as NiTi tubing, from the pattern of FIG. 17A and shape-set. Although not shown in FIGS. 17A-17I, the implant 13 of FIGS. 17A-17I may include any one or more of the features as described relative to an implant 13 described herein, including to implants of FIG. 8, FIG. 15 and FIGS. 16A-16C, such as being covered or encapsulated with a biocompatible graft material, having a laminating layer, and being coated with heparin and/or other therapeutic agents. In some embodiments, implant 13 according to FIGS. 17A-17I may be only partially covered or encapsulated with a biocompatible graft material, include a laminating layer and/or a coating, for example, only proximal implant segment 19 may be covered/encapsulated with a biocompatible graft material, have a laminating layer, and be coated.

Figure 18A:
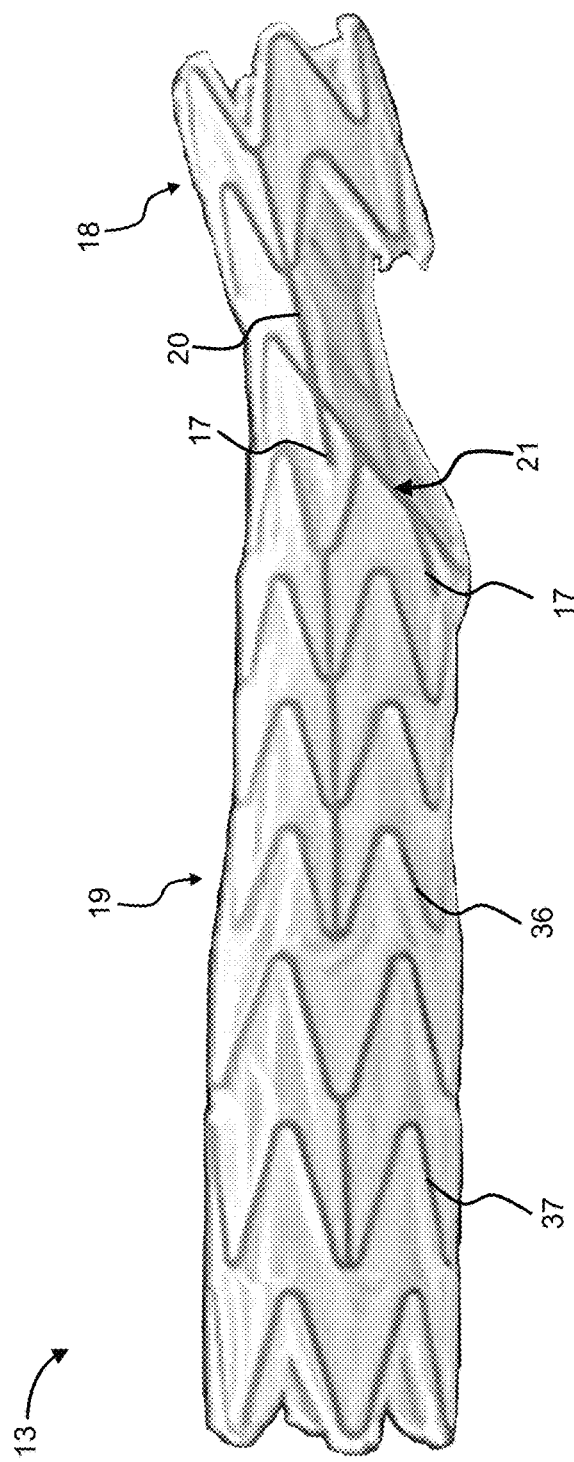
FIGS. 18A-18B depict endovascular implants according to some embodiments.
Figure 18B:
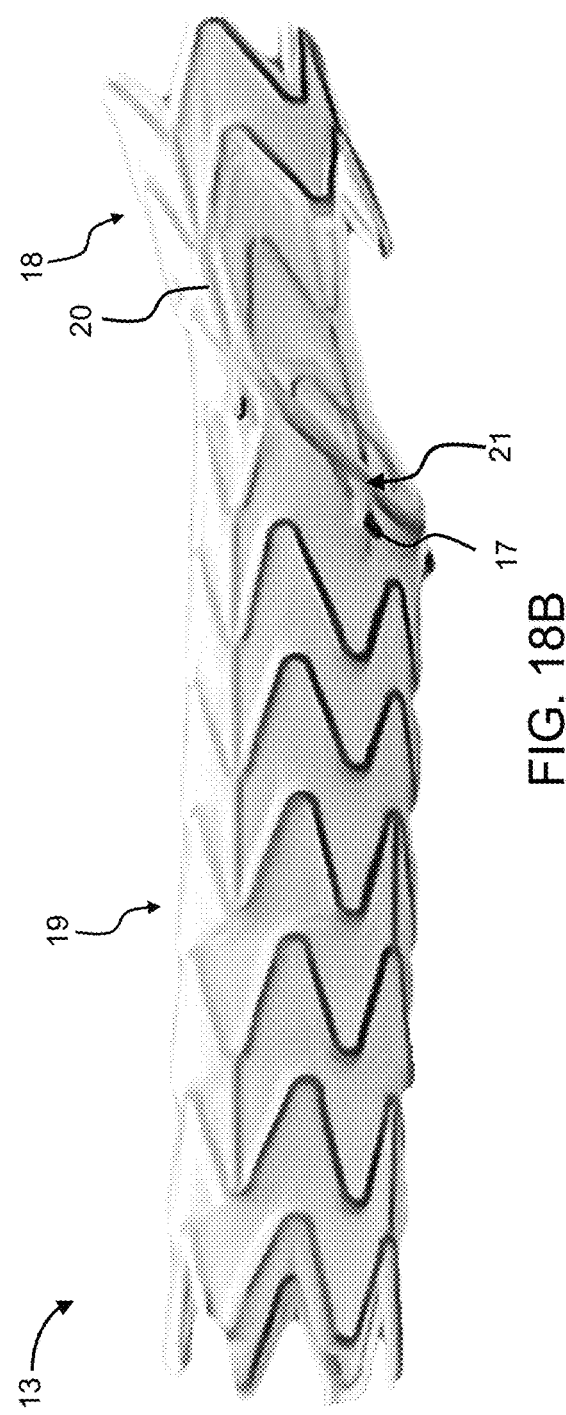

FIGS. 18A-18B depict various embodiments of implant 13 after being shape-set and encapsulated with a biocompatible graft material as described herein. Implant 13 of FIG. 18A may correspond to implant 13 as described in FIGS. 17A-17I and is shown including distal implant segment 18, proximal implant segment 19, connector struts 20, proximal anchor(s) 17, continuous strut/ring 21, shorter struts 36, and longer struts 37. As shown, and according to some embodiments, the section of proximal implant segment 19 where longer struts 37 are located has been formed to a diameter that is greater than a diameter of proximal implant segment 19 where shorter struts 36 are located. In alternative embodiments, such as shown in FIG. 18B, the proximal implant segment 19 of implant 13 may comprise struts of substantially similar length and have a substantially uniform diameter. FIG. 18B also shows various features of implant 13 as described herein, including distal implant segment 18, the afore mentioned proximal implant segment 19, connector struts 20, proximal anchor(s) 17, continuous strut/ring 21.

Figure 19:
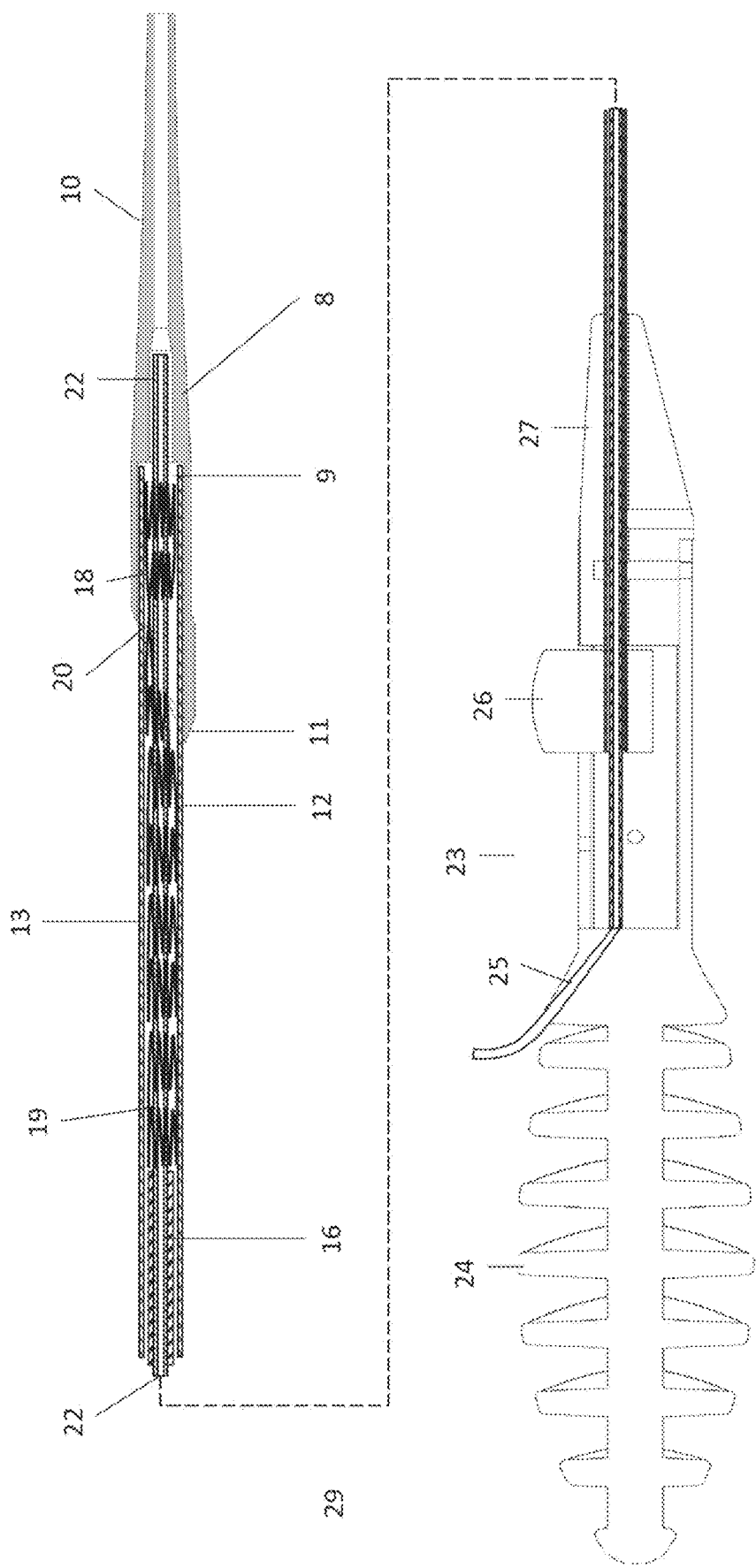
FIG. 19 depicts a partial cross-sectional view of various elements of a delivery system according to some embodiments.

FIG. 19 depicts a partial cross-sectional view of the various elements of one embodiment of delivery system 29. Nose cone 8 with distal taper 10 and tapered proximal end 11 is shown connected to guidewire shaft 22. Guidewire shaft 22 has an internal lumen which accommodates guidewire 5 (shown elsewhere). Middle shaft 16 is slidably deposed over guidewire shaft 22 and slidably deposed within outer sheath 12 and abuts the proximal end of constrained implant 13. The proximal end of middle shaft 16 terminates where it may be fixed to the proximal handle 23 or allowed to move relative to handle 23. Middle shaft 16 prevents implant 13 from moving relative to guidewire shaft 22 during retraction of outer sheath 12 during delivery of implant 13. Implant 13 is elastically constrained within outer sheath 12. Outer shaft 12 is attached to control knob 26 which is slidably attached to handle 23 so that a controlled retraction of outer sheath 12 can be achieved by sliding control knob 26 proximally. The distal end of outer sheath 12 terminates within cavity 9 of nose cone 8. At its proximal end, guidewire shaft 22 is fixed to handle 23 and is luminally connected to tube 25 which provides conduit for guidewire 5 to travel completely through delivery system 29. A hemostatic valve may be fitted on the proximal end of tube 25 to prevent bleed back when delivery system 29 is inserted in the vasculature. Also depicted in FIG. 19 are proximal handle 24 which facilitates manipulation of delivery system 29 and some of the constrained elements of implant 13 including distal implant segment 18, proximal implant segment 19 and connector struts 20. Handle nose cone 27 provides a guide path and support for outer sheath 12 which is slidably deposed within handle nose cone 27. FIG. 19 depicts a preferred embodiment of delivery system. Alternative preferred embodiments for delivery system 29 could include thumb wheel control of outer sheath 12 and pull wire features to allow active deflection of nose cone 8 to create gap 14 rather than relying on the curvature 6 of guidewire 5 as shown in FIG. 6. The materials of construction of delivery system 29 can be any of the materials well known to be used for catheter construction such as PEEK, HDPE, PeBax, nylon, PTFE, combinations thereof, and others. The diameter and length of delivery system 29 should be suited to the particular application. In one embodiment, the profile of nose cone 8 is between 6 Fr. and 9 Fr. for an implant 13 diameter of between 3 mm and 6 mm. In one embodiment, the distance between handle 23 and nose cone 8 is between about 15 cm and about 30 cm. Various lengths and diameters of delivery system 29 can be used in various embodiments of this invention to satisfy the needs of the particular application.

Figure 20:
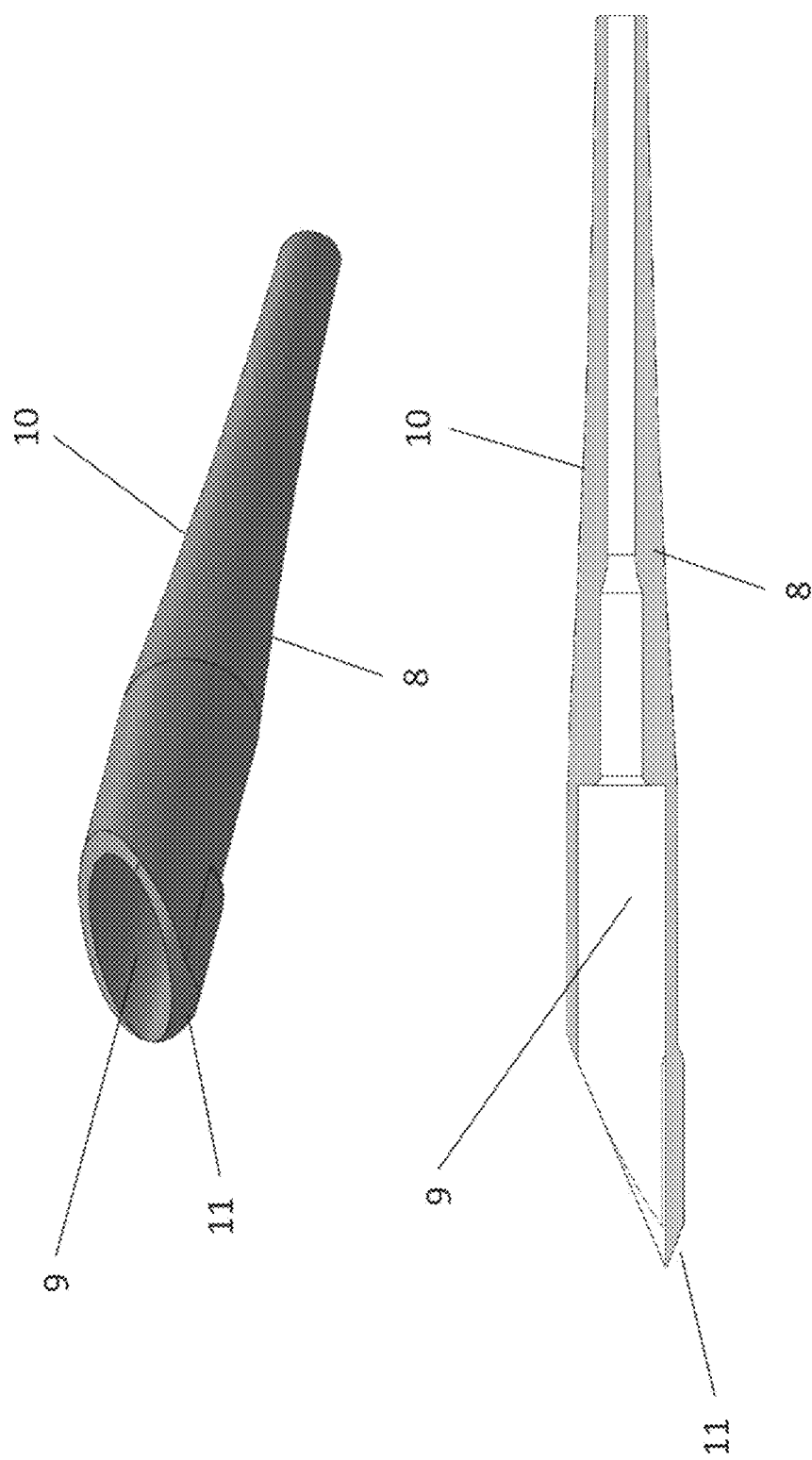
FIG. 20 depicts a perspective view and a cross-sectional view of a nose cone of a delivery system according to some embodiments.

FIG. 20 depicts a 3-D view and cross-sectional view of nose cone 8. According to some embodiments, tapered proximal end 11 is shown with a profile intended to engage tissue when gap 14 is created (shown above) and to not engage tissue or implant structures when gap 14 is eliminated. In some embodiments, tapered proximal end 11 may engage tissue without a gap 14. In some cases, tapered proximal end 11 may engage tissue when it is oriented substantially on the outside of a curve (e.g., such as the curvature 6), and may otherwise not engage tissue when it is oriented substantially on the inside of a curve. Cavity (e.g., central lumen) 9 is shown with dimensions sufficient to accept outer sheath 12 (not shown) and can include a proximal opening. The proximal opening can in some embodiments be oblique to the longitudinal axis of the nose cone 8. To improve the flexibility between nose cone 8 and outer sheath 12, a slit or slot may be included in the wall that forms cavity 9, preferably in the region of the shorter wall segment forming cavity 9 shown in the cross sectional view of nose cone 8. Nose cone 8 includes a tapered section 10 which facilitates sliding over guide wire 5 (not shown) and passing through anatomical structures that have not yet been dilated to a diameter equal to or greater to the outer diameter of nose cone 8. The tapered section 10 can taper distally in some cases as illustrated. Nose cone 8 can be constructed from materials well known to be suitable for catheters such as, for example, PEEK, HDPE and Polypropylene. In some embodiments, nose cone 8 may include echogenic features to aid in ultrasound visualization.

FIGS. 21A-21B depicts a 3-D view and cross-sectional view of handle 23 and its various elements. Handle nose cone 27 is shown attached to the distal end of handle 23 with a thru-lumen that slidably accommodates outer sheath 12 (not shown). Control knob 26 is slidably constrained within handle 23 and is used to control the axial position of outer sheath 12 (not shown). Tube 25 allows for passage of guidewire 5 (not shown) through handle 23.

Figure 22C:
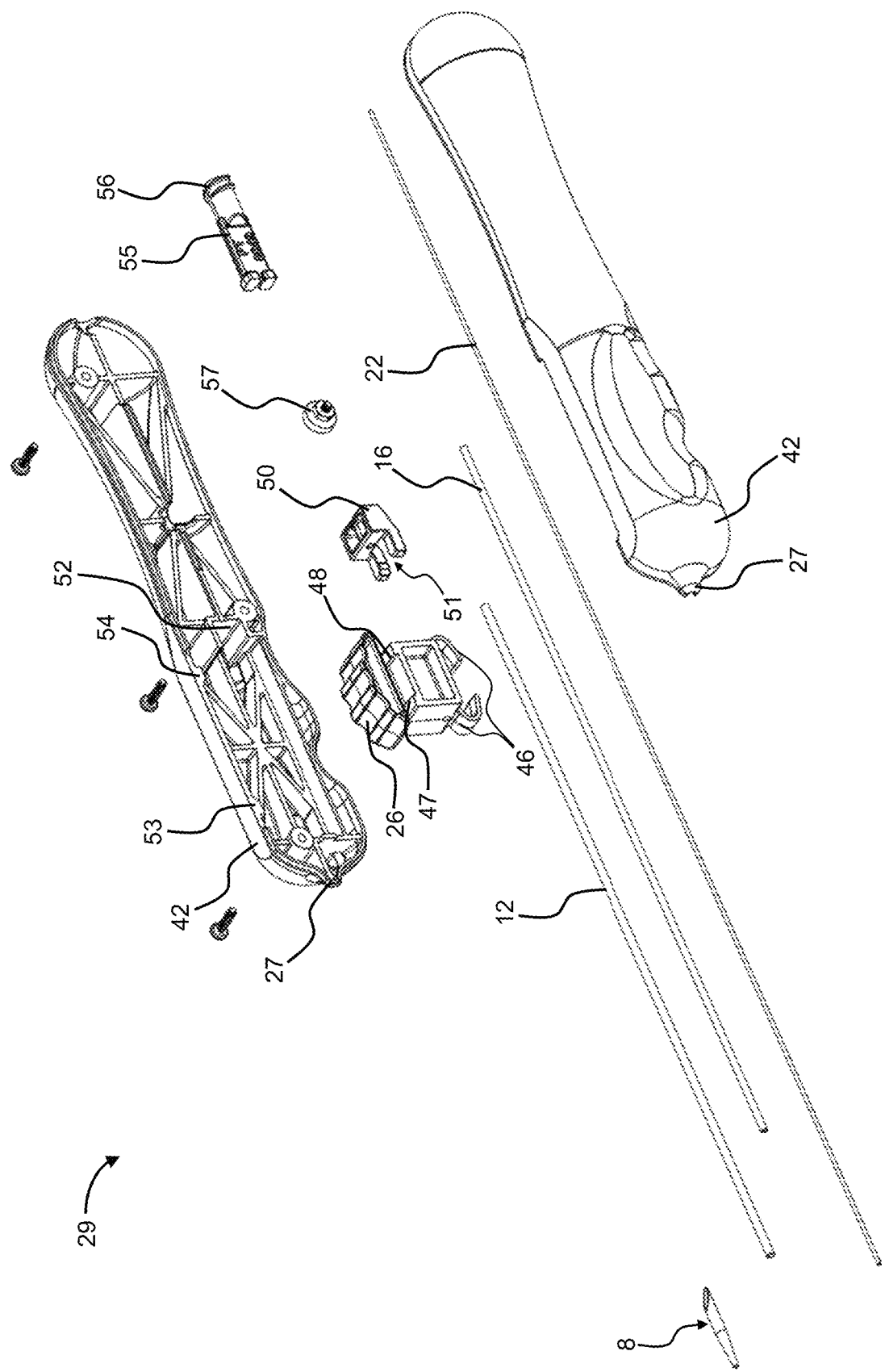
FIG. 22C depicts an exploded perspective view of a delivery system according to some embodiments.
Figure 22D:
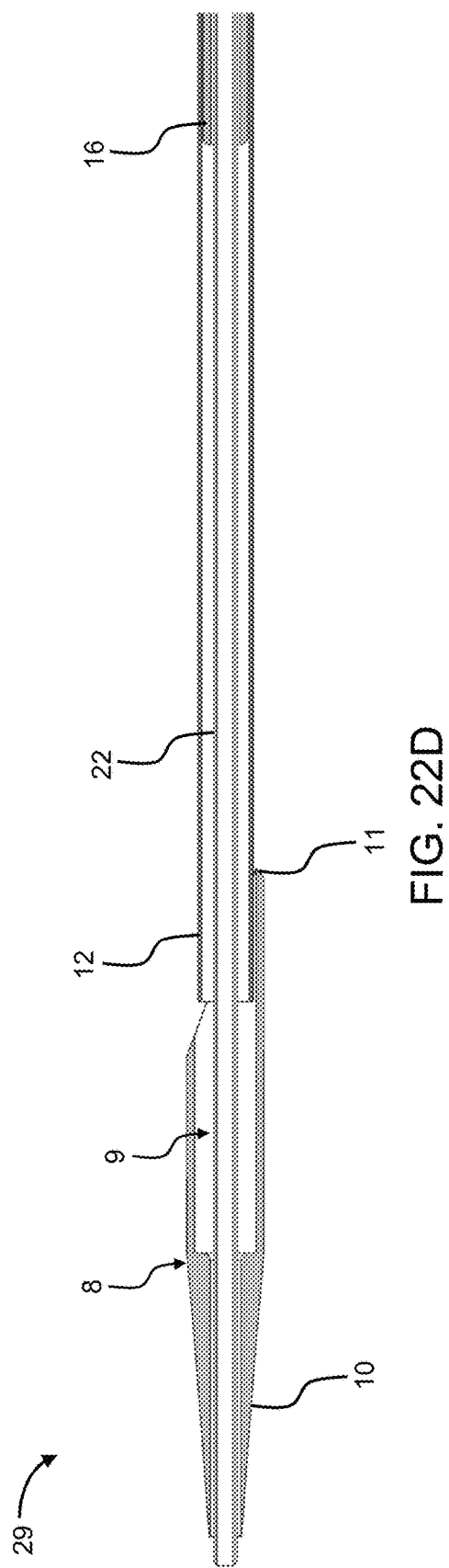
FIG. 22D depicts a cross-sectional view of a distal end of a delivery system according to some embodiments.
Figure 22E:
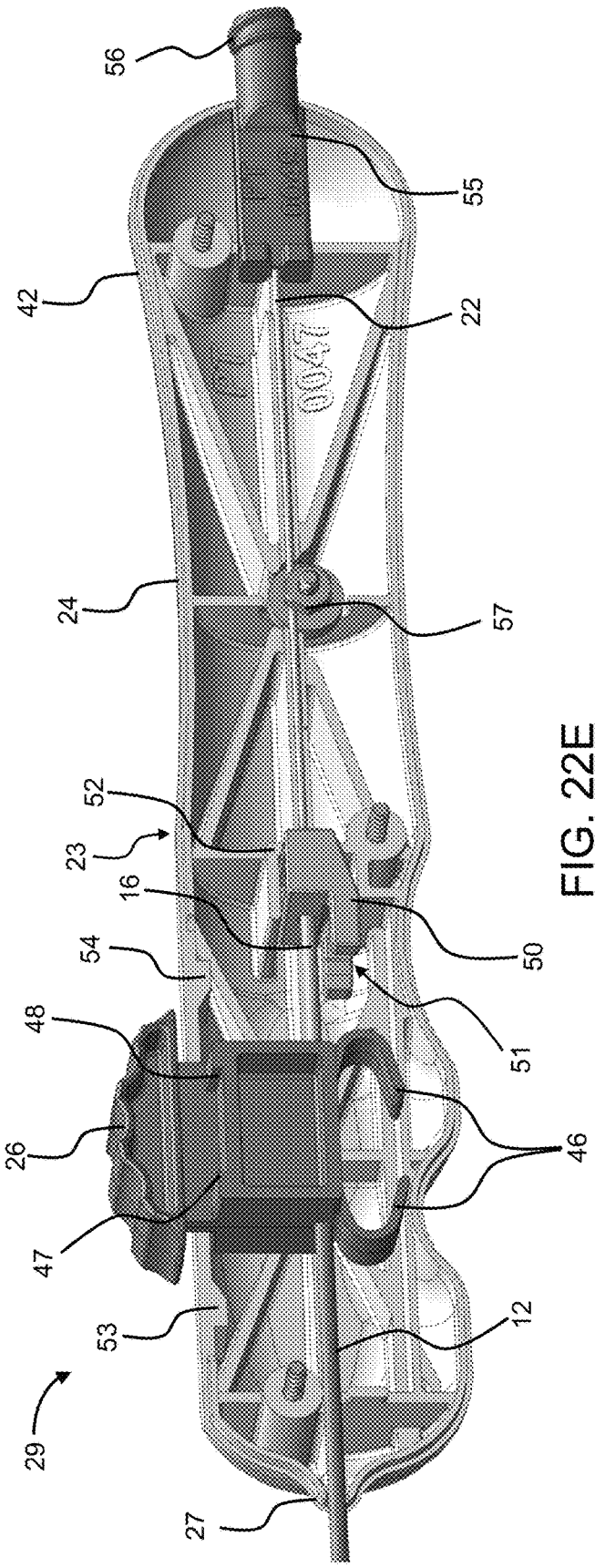
FIG. 22E depicts a perspective view of a delivery system according to some embodiments with part of a handle housing of the delivery system removed from view.

FIGS. 22A-22E depict another embodiment of a delivery system or device 29. The delivery device may be configured for percutaneous access into the arm or into another location of a patient. FIG. 22A shows a perspective view, FIG. 22B shows a cross-sectional perspective view, and FIG. 22C shows an exploded perspective view of the delivery device 29 according to this and some embodiments. Additionally, FIG. 22D shows a cross-sectional view of a distal end of the delivery device 29, and FIG. 22E shows a perspective view of the delivery device 29 with part of a handle housing of the delivery device 29 removed from view. The delivery device 29 depicted through FIGS. 22A-22E may share common elements with and may function similarly to the delivery device 29 depicted through FIGS. 19-21B; as such, common elements may share common reference numbers to indicate a general correspondence between referenced elements.

As shown in FIGS. 22A-22E, a delivery device 29 may comprise a handle 23, a control knob 26, a guidewire shaft 22, a middle shaft 16, an outer sheath 12, and a nose cone 8. The handle 23 may comprise a right housing 42 and a left housing 44, which may be secured together by mechanical fasteners, adhesive, or molded so as to snap fit or press fit together. As shown in FIG. 22A, the handle 23 may, at its proximal end, comprise a proximal handle 24, which can facilitate manipulation of the delivery device 29. Also shown in FIG. 22A, the handle 23 may, at its distal end, comprise a nose cone 27 with a thru-lumen, which can provide a guide path and support for the outer sheath 12 which is slidably disposed within the handle 23 and the nose cone 27. Also shown in FIG. 22A, the control knob 26 may be slidably constrained within a longitudinal opening of the handle 23, with a portion of the control knob 26 extending outside the handle 23 as shown for manipulation by a user. The nose cone 8 may be disposed at a distal end of the delivery device 29 and comprise features as described herein.

The perspective cross-sectional view of FIG. 22B and the exploded perspective view of FIG. 22C show additional details of the delivery device 29 shown in FIG. 22A according to some embodiments. As shown, the guidewire shaft 22 may traverse a longitudinal length of the handle 23. The guidewire shaft 22 may fluidly connect at its proximal end to a guidewire shaft connector 55 disposed partially within the handle 23 at the proximal end of the handle 23. The guidewire shaft connector 55 may be similar to the tube 25 as described herein. The guidewire shaft connector 55 may extend proximally beyond the handle 23 and terminate with a guidewire shaft connector fitting 56 that may be coupled to a valve and/or tubing for controlling bleed back when the delivery device 29 is inserted in the vasculature. The guidewire shaft connector 55, in being fluidly connected to guidewire shaft 22, may form a common lumen with the guidewire shaft 22 to allow for a guidewire 5 as described herein to be inserted into the proximal end of the guidewire shaft connector 55 (e.g., through the guidewire shaft connector fitting 56), travel through the guidewire shaft connector 55, and then travel through the guidewire shaft 22 as the guidewire 5 is translocated distally. Also shown, a guidewire shaft housing connector 57 may be disposed distal to the guidewire shaft connector fitting 56 within the handle 23, the guidewire shaft housing connector 57 configured to attach to the guidewire 22 and provide support (e.g., mechanical support) for the guidewire 22. Also shown, the delivery device 29 may further comprise a middle shaft connector 50 disposed within the handle 23 and configured to connect to a proximal end of the middle shaft 16. The delivery device 29 may further comprise a middle shaft connector stop 52, which as shown may be a feature of the handle 23 (e.g., a molded feature). Also shown, the control knob 26 may comprise a distal catch 47 and a proximal catch 48, which may interact with features of the handle 23 including, in some embodiments, a distal housing catch 53 and a proximal housing catch 54. Further, the control knob 26 may comprise spring elements 46, which may also interact with features of the handle 23.

Further connections of elements and operation of delivery device 29 according to some embodiments will be discussed next in reference to the cross-sectional view of FIG. 22D and the perspective view of FIG. 22E (which shows the delivery device 29 with left housing 44 of the delivery device 29 removed from view). As shown, the guidewire shaft 22 may extend substantially longitudinally within the handle 23 and may connect, as described above, at its proximal end to guidewire shaft connector 55. Further, the guidewire may extend distally through the handle nose cone 27 and end distally at a connection with nose cone 8. Thus, the guidewire shaft 22, in combination with the guidewire connector 55 and the nose cone 8, may form a central lumen configured to slidably accommodate a guidewire 5 as described herein (e.g., the guidewire 5 may be slid within the delivery device 29, and/or the delivery device may be slid along the guidewire 5).

The middle shaft 16 as described herein may be disposed coaxial with and slidably along the guidewire shaft 22, and as shown may have a proximal end that connects with the middle shaft connector 50 disposed within the handle 23 and a distal end that may terminate short of the nose cone 8. Thus, the middle shaft 16 and the middle shaft connector 50 may slidably move together distally/proximally along the guidewire shaft 22. The middle shaft connector 50 may have a proximal end configured to abut the middle shaft connector stop 52 when in its proximal-most position, and a distal end configured to interact with the control knob 26. In some embodiments, the middle shaft connector 50 may comprise a middle shaft connector recess 51 configured to engage the control knob 26 when the control knob 26 is slid to its proximal-most position in the handle 23. For example, the middle shaft connector recess 51 may frictionally engage the control knob 26 when the control knob 26 is slid proximally and brought within the recess. As another example, the middle shaft connector recess 51 may comprise protrusions that aid the middle shaft connector 50 in holding onto/engaging the control knob 26 when the control knob 26 is slid proximally and brought within the recess past the protrusions.

The outer sheath 12 as described herein may be disposed coaxial with and slidably along the middle shaft 16, and as shown may have a proximal end that connects with the control knob 26 and a distal end that may terminate within, partially within, or near the nose cone 8. Thus, the outer sheath 12 and control knob 26 may slidably move together distally/proximally along the middle shaft 16. The control knob 26 may comprise spring elements 46 as shown configured to provide an upward force to the control knob 26 by interaction between the spring elements 46 and an inner surface (e.g. a longitudinally-oriented inner surface) of the handle 23. The control knob 26 may also comprise features that may interact with the handle 23 and maintain the control knob 26 is desired positions distally and/or proximally. For example, the control knob 26 may comprise distal catch 47 and proximal catch 48 (which may each be in the form of a step-like edge) disposed near its distal end and its proximal end, respectively, and near where the control knob 26 protrudes through the longitudinal opening of the handle 23 as shown, and the handle 23 may comprise distal housing catch 53 and proximal housing catch 54 configured to interact with the distal catch 47 and the proximal catch 48, respectively. Further and as shown, the distal housing catch 53 and proximal housing catch 54 may be disposed adjacent a distal end and a proximal end, respectively, of the longitudinal opening of the handle 23, and may each comprise a ramp-like surface facing towards the control knob 26 and a step-like edge facing away from the control knob 26. In such embodiments and further to this example, when the control knob 26 is slid distally to its full distal position, the control knob 26 may deflect downward (e.g., inward into the handle 23) as it comes into contact and rides along the ramp-like surface of the distal housing catch 53 until the step-like edge of the distal catch 47 passes the step-like edge of the distal housing catch 53, at which point the control knob 26 can return to its more upward position within the handle 23 and the interaction between the step-like edges of the distal catch 47 and the distal housing catch 53 keep the control knob 26 locked into place. To unlock the control knob 26 from this distal position, the control knob 26 may be pushed inward towards the center of the handle 23 (opposing the upward force provided by the spring elements 46) until the step-like edge of the distal catch 47 is free of the step-like edge of the distal housing catch 53 (e.g., they are no longer overlapping longitudinally) and then the control knob 26 may be slid proximally. Locking and unlocking of the control knob 26 in its proximal-most position may be performed similarly with the corresponding proximal catch 48 and proximal housing catch 54. In some embodiments, when the control knob 26 is slid proximally into its proximal-most position, the control knob 26 may engage with the middle shaft connector recess 51 of the middle shaft connector 50, causing the middle shaft connector 50 to lock onto the control knob 26; subsequent movement/sliding of the control knob 26 may then cause the middle shaft connector 50 and the middle shaft 16 it is connected to move together with control knob 26 and the outer sheath 12. The middle shaft connector stop 52 as described above may aid in the engagement of the middle shaft connector 50 with the control knob 26 by preventing proximal movement of the middle shaft connector 50 as the control knob 26 is moved proximally into the middle shaft connector recess 51. In some embodiments, the control knob 26 and handle 23 may comprise other features that aid in locking the control knob 26 in a desired position. In some embodiments, the distal catch 47, proximal catch 48, distal housing catch 53, and proximal housing catch 54 may comprise features different than described above but that may function similarly.

As described herein and shown also in FIG. 22D, the distal end of delivery device 29 may comprise a nose cone 8 comprising a distal taper 10, a cavity 9, and a tapered proximal end 11. The distal taper 10 may be symmetric along a longitudinal length of the nose cone 8 and may comprise a longitudinal through opening; in some embodiments, the guidewire shaft 22 may attach to the nose cone 8 at the longitudinal through opening. The longitudinal through opening may comprise a diameter and/or cross-sectional area that is smaller than a diameter and/or cross-sectional area of the cavity 9. The cavity 9 may comprise a diameter and/or cross-sectional area that is greater than an outer diameter of the outer sheath 12. The nose cone 8 may comprise a proximal end that is at an angle relative to the longitudinal length of the nose cone 8. For example, and using FIG. 22D as a reference, the nose cone 8 may comprise a proximal end that is at an angle of about 30 degrees relative to the longitudinal length of the nose cone 8, although other angles may be used. In some embodiments, the nose cone 8 may comprise a proximal end that is at an angle of between about 5 degrees to about 90 degrees relative to the longitudinal length of the nose cone 8. In some embodiments, the nose cone 8 may comprise a proximal end that is at an angle of about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees relative to the longitudinal length of the nose cone 8. In some embodiments, the angled proximal end of the nose cone 8 may allow the nose cone 8 to deflect preferentially in one direction and not in another. For example, the nose cone 8 as shown in FIG. 22D may preferentially deflect upwards (i.e., the distal end of the nose cone 8 may deflect upwards) and may not preferentially deflect downwards due to the angled proximal end. In some embodiments, the distal end of the nose cone 8 may be inhibited from movement in a direction due to the angled proximal end of the nose cone 8 substantially inhibiting movement (e.g., the proximal end of the nose cone inhibits movement due to interaction with any one of the guidewire shaft 22, the middle shaft 16, and/or the outer sheath 12). The proximal facing edge of the proximal end of nose cone 8 may comprise a taper, for example as shown in FIG. 20, which may also be known as the tapered proximal end 11 described herein. As shown, the tapered proximal end 11 of the nose cone 8 may taper down to a smaller cross-sectional area in the proximal direction, i.e., it may comprise a taper opposite the distal taper 10. As such, the taper of the tapered proximal end 11 may aid in retraction of the nose cone 8 as described herein. In some embodiments, the proximal end of the nose cone 8 may comprise a transverse cross-sectional shape that is circular, round, oval, oblong, pear-shaped, egg-shaped, or any symmetric or irregular shape. In some embodiments, a width of the proximal end of the nose cone 8 may be larger than a height of the proximal end of the nose cone 8 along the longitudinal axis of the nose cone 8. In some embodiments, the cavity 9 may be sized larger than an outer diameter of the outer sheath 12. In some embodiments, the cavity 9 may have a width that is greater than its height.

The guidewire shaft 22 may provide a semi-rigid semi-flexible conduit that may serve as a catheter extending from the handle 23 of the delivery device and terminate at its distal end with the nose cone 8. Thus, in use, the distal or proximal location of the nose cone 8 in the body may be directly affected by distal or proximal movement of the delivery device 29, such as by a clinician operating the delivery device 29. As described herein, the distal and/or proximal movement of the middle shaft 16 and/or the outer sheath 12 may be controlled by manipulation of the control knob 26 (e.g., by distal and/or proximal sliding of the control knobe 26). The delivery device 29 may be configured for single-handed operation by a clinician/user/operator. Single-handed operation of the delivery device 29 may advantageously allow a clinician/user/operator to keep their other hand free to perform additional aspects related to the procedure. Also, single-handed operation of the delivery device 29 may reduce and/or eliminate the need for additional staff to assist with the procedure. Additionally, single-handed operation of the delivery device 29 may advantageously increase the efficiency of the procedure. Single-handed operation of the delivery device 29 may advantageously allow the clinician/user/operator to simultaneously control an ultrasound imaging probe with their other hand during the procedure.

The delivery device 29 may be used to percutaneously deliver an intraluminal implant 13 as described herein. In some embodiments and as described herein, at least a portion of the implant 13 may be disposed within the cavity 9 of the nose cone 8. In some embodiments, at least a portion of the implant 13 may be disposed within the outer sheath 12. In some embodiments, the middle shaft 16 may abut an end of the implant 13 when the implant is disposed within the delivery device 29. In some embodiments, the implant 13 may be slidably disposed over the guidewire shaft 22. In some embodiments, the implant may be disposed at least partially within the cavity 9 of the nose cone 8 while also being at least partially disposed within the outer sheath 22. In some embodiments, the implant 13 may be disposed within the delivery device 29 in a radially compressed configuration and packaged as a kit. In some embodiments, a kit may comprise a delivery device 29 and an implant 13. In some embodiments, the kit may further comprise a needle access tool 35 and/or a guidewire 5. In some embodiments, the delivery device 29 may be single-use. In some embodiments, the delivery device 29 may be reusable. In some embodiments, any of the components and devices described herein may be provided sterile or non-sterile.

Provided next is a description, according to some embodiments, of how the delivery device 29 described above and in reference to FIGS. 22A-22E may percutaneously deliver an implant 13 after a guidewire 5 has already been placed through a vasculature and an adjacent vasculature desired to be connected by an AVF, however the description provided may be applicable to the delivery devices and methods described previously. In some embodiments, the delivery device 29 may be provided with an implant 13 in a radially compressed configuration slidably disposed over the guidewire sheath 22, slidably disposed within the outer sheath 12, at least partially within the cavity 9 of the nose cone 8, and with the middle shaft 16 abutting its proximal end. Furthermore, the control knob 26 of the delivery device 29 as provided may be in its distal most position relative to the handle 23 of the delivery device 29 (and, in some embodiments, may be locked in the distal most position via the interaction between the distal catch 47 of the control knob 26 and the distal housing catch 53 of the handle 23). After being slid distally over a guidewire 5 until the nose cone 8 is positioned past the desired AVF location within a lumen of the vasculature (see FIG. 4), the delivery device may be pulled back proximally to engage the nose cone 8 against the near wall of the vasculature as described herein (see FIG. 5). With the delivery device 29 and its nose cone 8 in this position, the control knob 26 may be moved (e.g., slid) to its proximal most position relative to the handle 23 of the delivery device 29 to proximally retract the outer sheath 12 (see FIGS. 6A-6B). In some embodiments, this may comprise unlocking of the distal catch 47 of the control knob 26 from the distal housing catch 53 of the handle 23 before the control knob 26 can be moved proximally, and may also include locking the control knob 26 in its proximal most position via the interaction between the proximal catch 48 of the control knob 26 and the proximal housing catch 54 of the handle 23. The proximal retraction of the outer sheath 12 may allow at least a portion of the implant 13 to radially expand within a lumen of an adjacent vasculature as well as at least a portion of the implant to expand within the cavity 9 of the nose cone 8. In some embodiments, the control knob 26 may engage with the middle shaft connector 50 when moved into its proximal most position within the handle 23 of the delivery device 29 and lock the middle shaft connector 50 to the control knob 26. With the control knob 26 kept in its proximal most position, the delivery device 29 may be advanced distally over the guidewire 5 to fully release the implant 13 from the cavity 9 of the nose cone 8 and allow the implant to fully radially expand within the lumen of the vasculature (see FIG. 8). The control knob 26 may be moved (e.g., slid) from its proximal most position to its distal most position relative to the handle 23 (which in some embodiments may include unlocking of the proximal catch 48 from the proximal housing catch 54 and again locking of the distal catch 47 to the distal housing catch 54), which can cause both the middle shaft 16 and the outer sheath 12 to advance distally through the radially expanded implant and engage the nose cone 8 as described herein (see FIG. 9). The delivery device 29 may be rotated (e.g., rotated about 180 degrees) to create a smooth transition between the nose cone 8 and the outer sheath 12 (e.g., eliminate any gap 14 as described herein, see FIG. 10A or 10B) and retracted proximally until it is completely removed from the body (see FIGS. 11-14).

The materials of construction of delivery device 29 can be any of the materials well known to be used for catheter construction such as PEEK, HDPE, PeBax, nylon, PTFE, combinations thereof, and others. The diameter and length of delivery device 29 can be suited to the particular application. In some embodiments, the profile of nose cone 8 may be between 6 Fr. and 9 Fr. for an implant 13 diameter of between 3 mm and 6 mm. In some embodiments, the distance between handle 23 and nose cone 8 may be between about 15 cm and about 30 cm. Various lengths and diameters of delivery device 29 can be used in various embodiments to satisfy the needs of the particular application. Nose cone 8 can be constructed from materials well known to be suitable for catheters such as, for example, PEEK, HDPE and Polypropylene. In some embodiments, nose cone 8 may include echogenic features to aid in ultrasound visualization.

In some embodiments, the delivery device 29 may comprise a mesh or other wrapping disposed around the implant 13 to maintain the implant 13 in a radially compressed (e.g., elastically constrained) configuration. In such embodiments, the implant 13 may be released from its radially compressed configuration and expanded into its radially expanded configuration by pulling a thread or wire of the mesh or wrapping configured to tear the mesh or wrapping, thus releasing the implant 13. Furthermore, in such embodiments the delivery device 29 may not require an outer sheath 12 or a middle shaft 16.

Returning to the simplified representation of a portion of the vasculature of the human arm shown FIG. 1, the location 7 that is a potential area to create an anastomotic connection may be where a radial artery is adjacent to a branching point between a brachial vein and a radial vein in the proximity of a perforator vein. For example, as depicted in FIG. 1, artery 4 may comprise a radial artery, deep vein 3 may comprise a brachial vein and/or a radial vein (e.g., to the left of location 7 the vein may be the brachial vein, and to the right of location 7 the vein may be the radial vein), perforator vein 2 may comprise a perforator vein, and superficial vein 1 may comprise a cephalic vein. Prior to implantation of implant 13, blood flow may be as follows as described relative to FIG. 1: blood flow in the radial artery (e.g., artery 4) may be from left to right; blood flow in the brachial vein and the radial vein (e.g., deep vein 3) may be from right to left; blood flow in the perforator vein (e.g., perforator vein 2) may be from the brachial vein and/or the radial vein and diagonally upwards and to the left to the cephalic vein; and blood flow in the cephalic vein (e.g., superficial vein 1) may be from right to left.

Returning to FIGS. 2A-2D, in some embodiments the guidewire 5 may be placed percutaneously through a wall of the cephalic vein (e.g., superficial vein 1), through the perforator vein (e.g., perforator vein 2), through the brachial vein or the radial vein (e.g., deep vein 3), through a wall of the brachial vein or the radial vein (e.g., deep vein 3), through the or any interstitial tissues between the brachial vein or the radial vein and the radial artery (e.g., artery 4), through a wall of the radial artery (e.g., artery 4), and into the radial artery (e.g., artery 4).

Returning to FIG. 15, in some embodiments the implant 13 may be implanted with the distal implant segment 18 (which may also be referred to herein as the arterial implant segment) positioned within the radial artery (e.g., artery 4) and the proximal segment 19 (which may also be referred to herein as the venous implant segment) extending through the brachial vein or the radial vein (e.g., deep vein 3) and the perforator vein (e.g., perforator vein 2). After implantation of implant 13 as such, blood flow may be as follows as described relative to FIG. 15: blood flow in the radial artery (e.g., artery 4) may be from left to right and enter the side opening or port (e.g., the side opening or port between the proximal implant segment 19 and the distal implant segment 18) of the implant 13 as shown and (i) flow through the proximal end of the distal implant segment 18 and out the distal end of the distal implant segment 18 to continue through the artery, and (ii) flow through the distal end of the proximal implant segment 19 and out the proximal end of the proximal implant segment 19 to flow into the perforator vein (e.g., perforator vein 2) and into the cephalic vein (e.g., superficial vein 1). In some embodiments and with continued reference to FIG. 15, after implantation of implant 13 as described above, blood flow through the brachial vein and/or the radial vein (e.g., deep vein 3) may be at least partially blocked or completely blocked by the proximal implant segment 19. In some embodiments, the proximal segment 19 blocking blood flow through the brachial vein and/or the radial vein (e.g., deep vein 3) may advantageously send more blood through the cephalic vein (e.g., superficial vein 1) and further enhance the development of the cephalic vein for use in hemodialysis. In some embodiments, the proximal segment 19 of the implant 13 may advantageously send blood from the radial artery (e.g., artery 4) directly into the perforator vein (e.g., perforator vein 2) and/or the cephalic vein (e.g., superficial vein 1) and bypass one or more branch points of the brachial vein and/or the radial vein (e.g., deep vein 3). In some embodiments and with continued reference to FIG. 15, after implantation of implant 13 as described above, blood flow through the cephalic vein (e.g., superficial vein 1) may be from right to left, and may include venous blood as well as arterial blood as provided by the implant 13. Arterial blood may flow through the proximal implant segment 19 of the implant 13 due to the pressure differential between the artery 4 and the perforator vein 2 and/or superficial vein 1. The flow of arterial blood in the cephalic vein (e.g., superficial vein 1) due to the implant 13 may advantageously cause the cephalic vein to increase in at least one of its size (e.g., diameter), thickness, and blood flow rate. For example, the flow of arterial blood in the cephalic vein (e.g., superficial vein 1) due to the implant 13 may advantageously cause the cephalic vein to increase in diameter to at least about 4 mm, at least about 5 mm, or at least about 6 mm. In another example, the flow of arterial blood in the cephalic vein (e.g., superficial vein 1) due to the implant 13 may advantageously cause the blood flow in the cephalic vein (e.g., superficial vein 1) to be at least about 400 cc/min, at least about 500 cc/min, or at least about 600 cc/min. In some embodiments, the implant 13 may lead the superficial vein 1 to develop into a point of single access for hemodialysis (e.g., two needles, one for outflow and the other for return flow, in the same vein). In some embodiments, the implant 13 may lead the superficial vein 1 to develop a diameter of at least about 6 mm and a blood flow rate of at least about 600 cc/min.

In further reference to FIG. 15 and as described herein, the proximal implant segment 19 may be angled relative to the distal implant segment 18. Said another way and as described herein, in some embodiments, an axis (e.g., longitudinal axis) of the proximal implant segment 19 may be angled relative to an axis (e.g., longitudinal axis) of the distal implant segment 18. The proximal implant segment may be angled relative to the axis of the distal implant segment by between about 0 and 90 degrees. In some embodiments, the proximal implant segment may be angled relative to the axis of the distal implant segment by about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees.

In further reference to FIG. 15 as well as to at least FIGS. 16C, 17B, 17C, 18A, and 18B and as described previously herein, the implant 13 may comprise a side opening or port disposed between the proximal implant segment 19 and the distal implant segment 18. The side opening or port may be disposed between the distal end of the proximal implant segment 19 and the proximal end of the distal implant segment 18. As shown in at least some of the figures mentioned above, the side opening or port may be formed by the continuous strut and/or ring 21 of the proximal implant segment 19, the connector struts 20, and the struts comprising the proximal end of the distal implant segment 18. In some embodiments, the distal implant segment 18 may be positioned downstream of the distal end of the proximal implant segment 19 (e.g., downstream in regard to the direction of arterial blood flow as shown).

Figure 23:
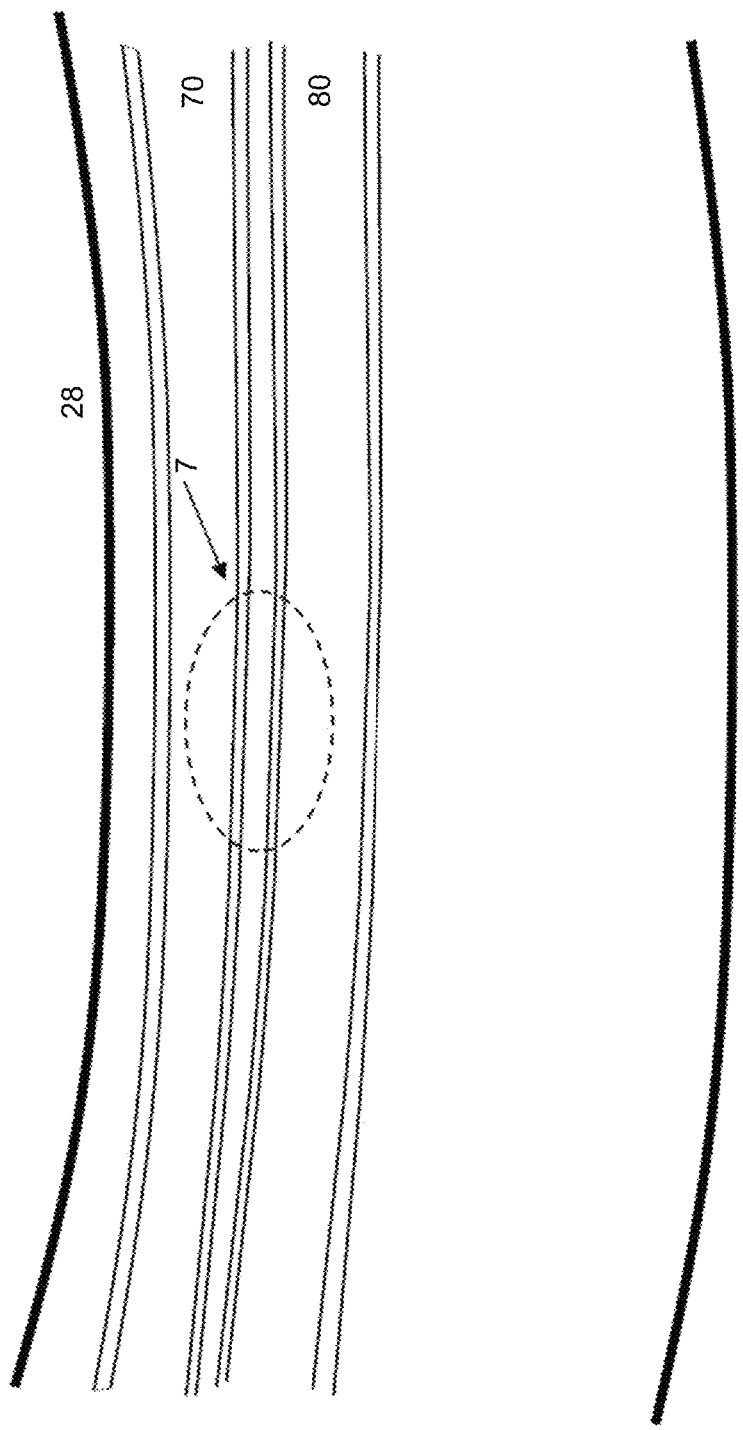
FIG. 23 depicts a simplified representation of a portion of the human vasculature indicating a potential area to create an anastomotic connection according to some embodiments.

FIG. 23 depicts a simplified representation of a portion of the human vasculature indicating a potential location 7 to create an anastomotic connection (e.g., AVF) between an artery 70 and a vein 80 that underly the dermal surface 28 according to some embodiments.

Figure 24:
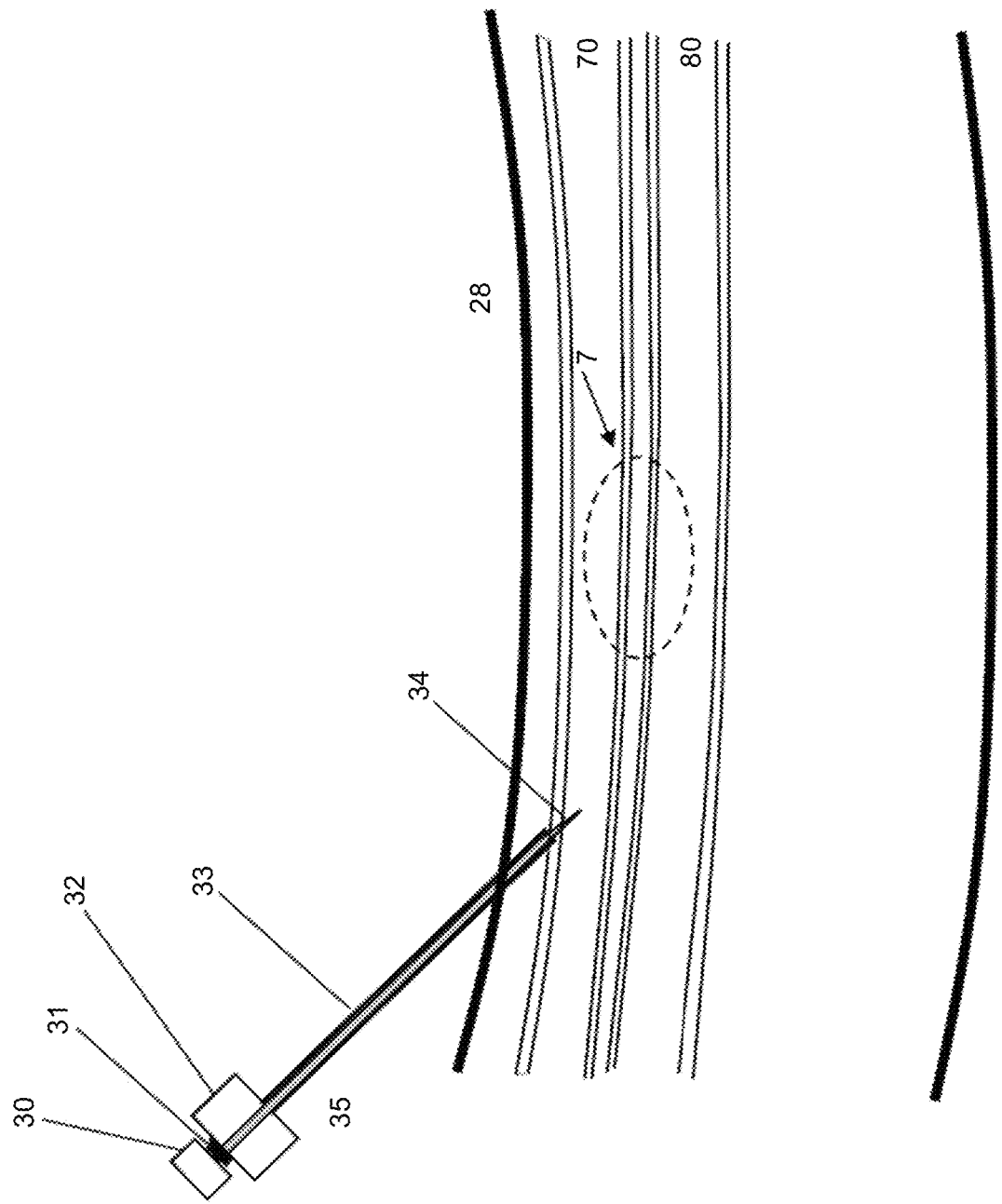
FIGS. 24-27 depict a method of percutaneously introducing an endovascular guidewire according to some embodiments.
Figure 25:
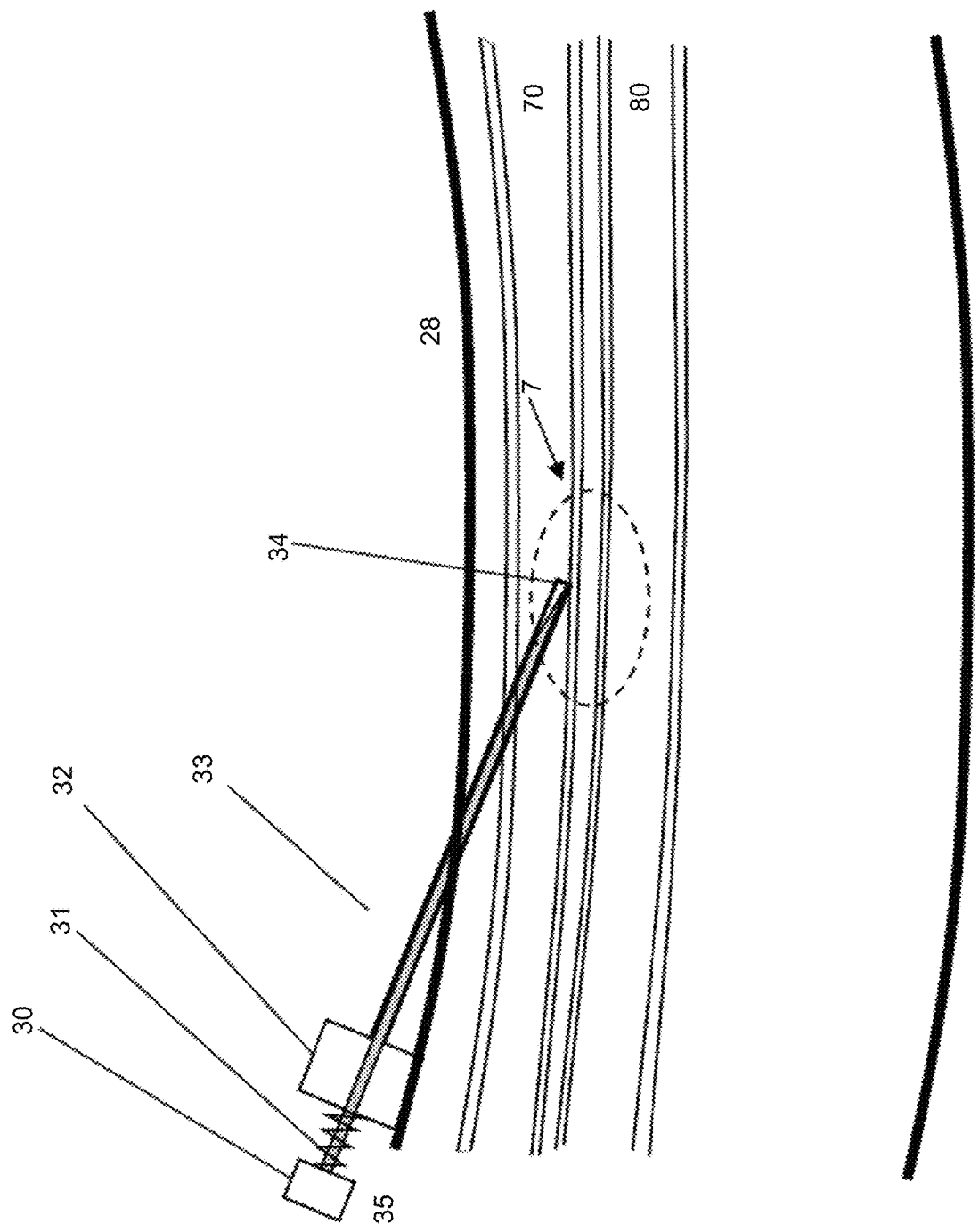
Figure 26:
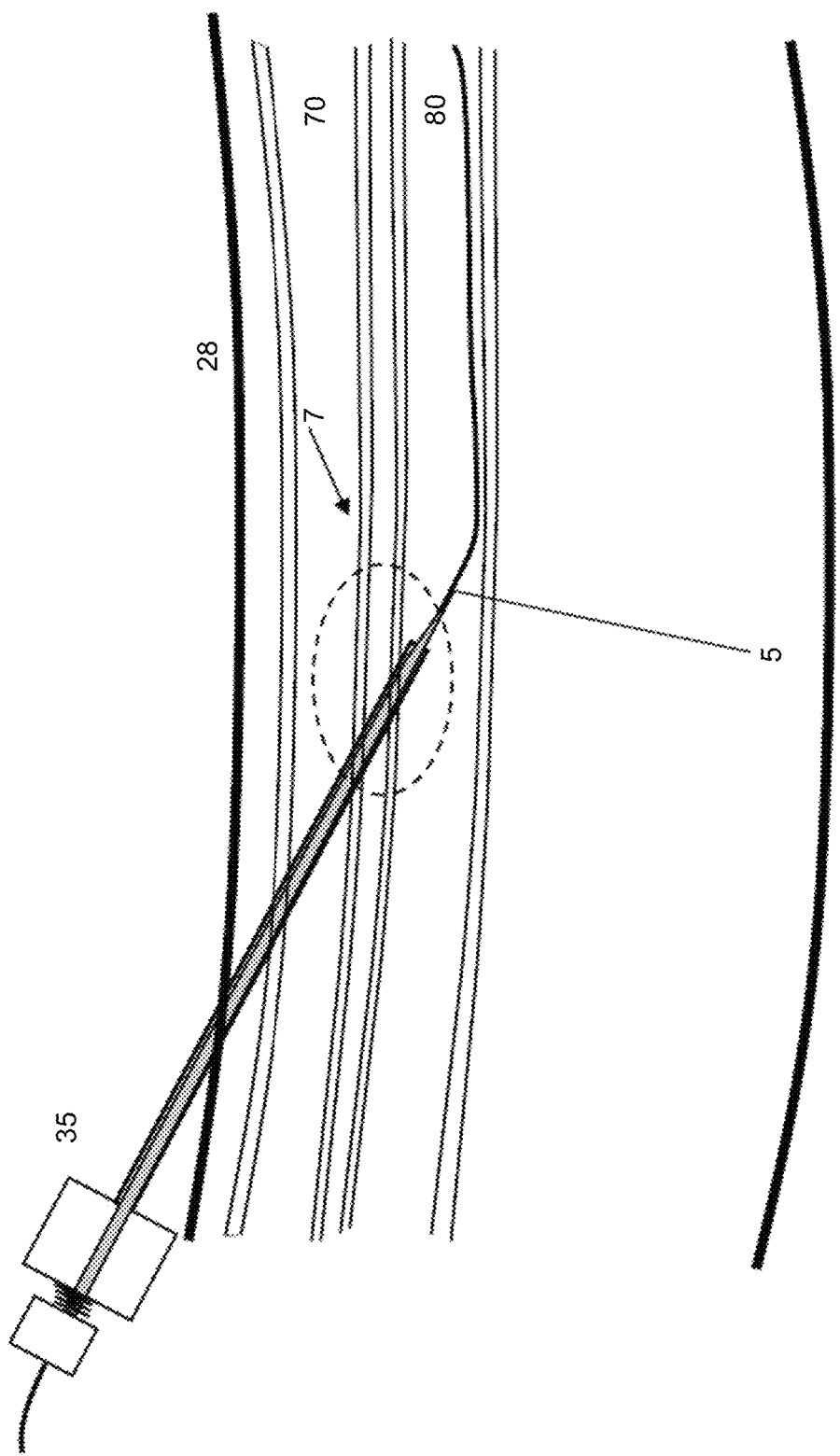
Figure 27:
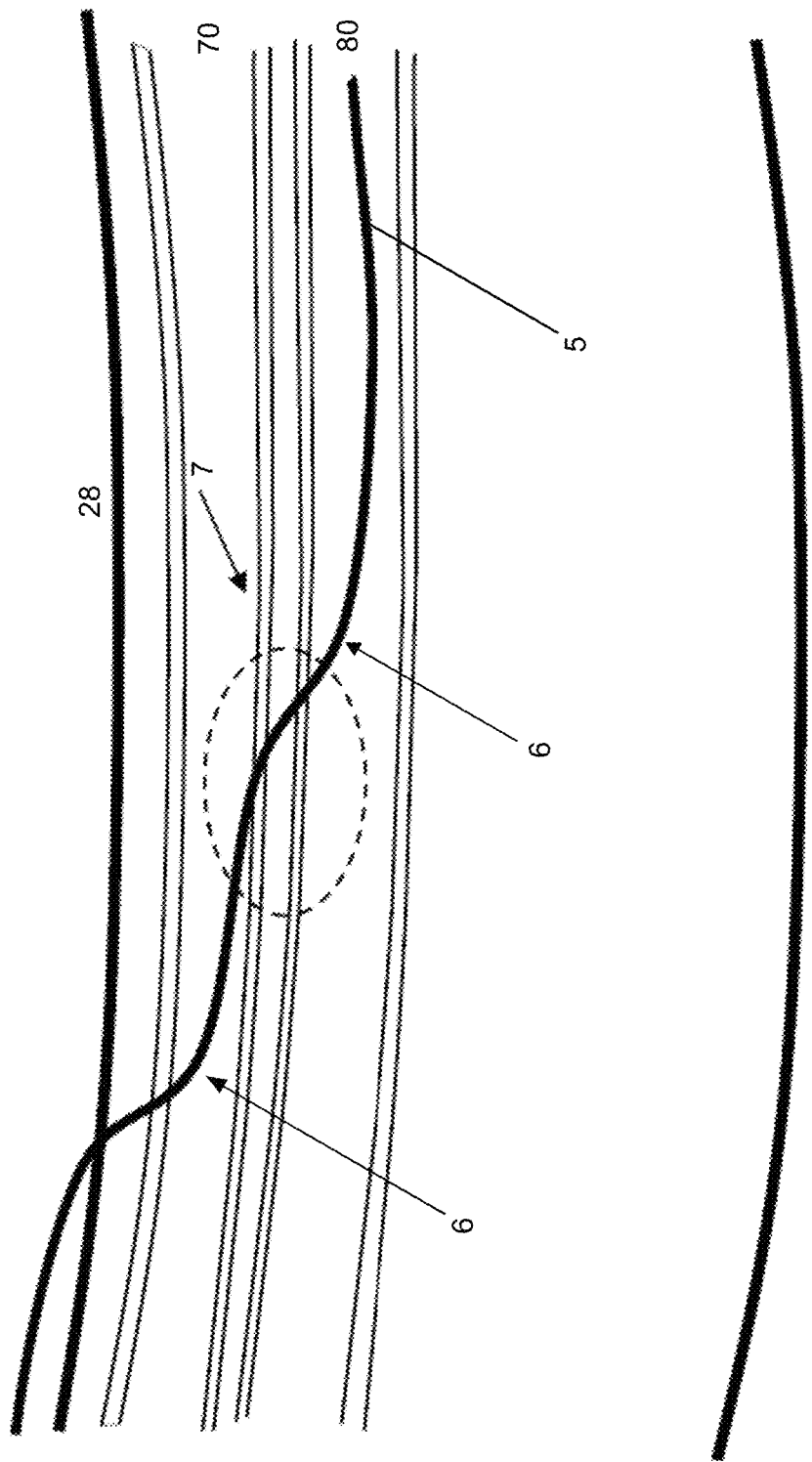

FIGS. 24-27 depict a method of percutaneously introducing an endovascular guidewire 5 according to some embodiments. The method shown and described through FIGS. 24-27 may comprise similar steps and/or aspects to the method previously described through FIGS. 2A-2D herein. As shown in FIGS. 24-27, the guidewire 5 may be percutaneously introduced by the needle access tool 35 as described herein. The needle access tool 35 can include a hollow needle with proximal port 30 and distal sharpened tip 34 slidably disposed within sheath 33. Sheath 33 may be connected to hub 32 that may comprise a compression element, such as compression spring 31 placed between port 30 and hub 32. When port 30 is depressed, needle tip 34 may be exposed distally of the distal end of sheath 33 and be able to puncture tissue such as skin and blood vessels. When port 30 is not depressed, spring 31 may decompress and move needle tip 34 proximally so that it is not exposed. In this configuration, the needle access tool 35 can navigate the vasculature with reduced risk of inadvertent punctures and trauma to the vasculature or other tissues. Using this feature of the needle access tool 35 and appropriate imaging techniques, such as transdermal ultrasound, the needle access tool 35 may be first introduced into artery 70 as shown in FIG. 24. With needle tip 34 retracted within sheath 33, the needle access tool 35 may be navigated to location 7 using appropriate imaging as shown in FIG. 25. While at location 7, the proximal port 30 may be actuated (e.g., depressed) to expose needle tip 34 and the needle access tool 35 may then be advanced to penetrate the vascular walls and the or any interstitial tissues between artery 70 and vein 80 until the distal end of sheath 33 enters the lumen of vein 80. While maintaining this position, guidewire 5 may be introduced into proximal port 30 and advanced through the needle access tool 35 until the distal end of guidewire 5 exits the distal end of the needle access tool 35 and enters the lumen of vein 80 as shown in FIG. 26. FIG. 27 shows guidewire 5 with curvatures 6 which may form when guidewire 5 conforms to the particular vascular anatomy after removal of the needle access tool 35.

Figure 28:
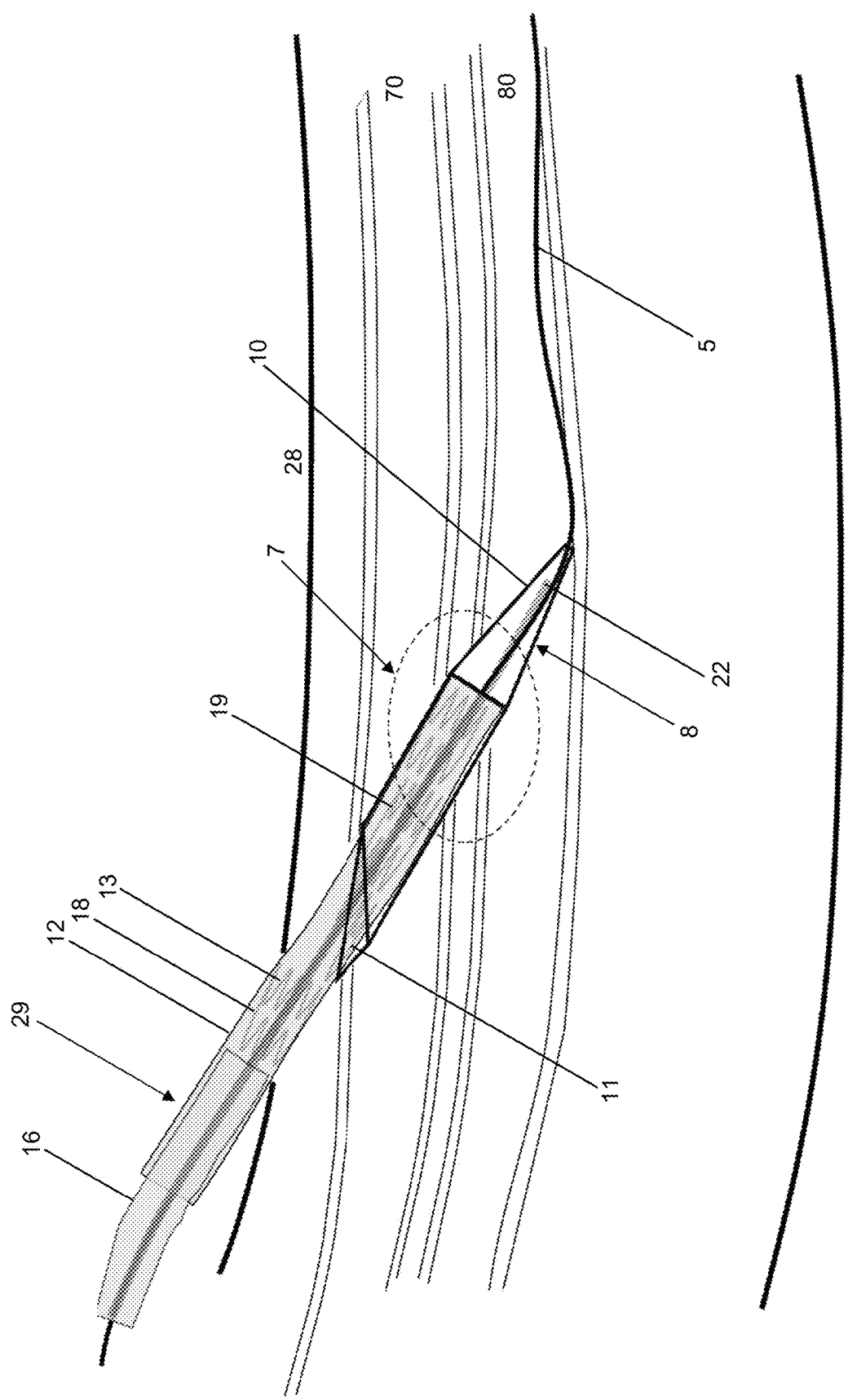
FIGS. 28-38 depict a method of percutaneously implanting an endovascular implant according to some embodiments.

FIGS. 28-38 depict a method of percutaneously implanting an endovascular implant 13 with a delivery device 29 according to some embodiments. FIG. 28 depicts the delivery device 29 after being placed over guidewire 5 and slid along the guidewire 5 distally to cause its distal end (e.g., the nose cone 8 at the distal end of the delivery device 29) to go through the dermal surface 28, through the artery 70, through the or any interstitial space between the artery 70 and the vein 80, and into the vein 80 (e.g., into the lumen of vein 80). As shown, implant 13 may be disposed within the delivery device 29 in a radially compressed configuration. In some embodiments, the proximal implant segment 19 as described herein may be disposed within the distal end of the delivery device 29 in a radially compressed configuration and the distal implant segment 18 may be disposed within the distal end of the delivery device 29 in a radially compressed configuration, however as shown here and opposite the method of implantation described through FIGS. 3-15, the distal implant segment 18 may be oriented more proximal of the distal end of the delivery device 29 than the proximal implant segment 19 (e.g., the implant 13 is reversed relative to its orientation as described through FIGS. 3-15). Thus, as described relative to FIGS. 28-38, the distal implant segment 18 will be referred to as the arterial implant segment 18, and the proximal implant segment 19 will be referred to as the venous implant segment 19; however, when discussing the distal and proximal ends of the implant segments, the convention used thus far herein will remain. Returning to FIG. 28, as shown the implant 13 may be disposed over guidewire shaft 22 and radially compressed within the outer sheath 12, with the venous implant segment 19 disposed at least partially within the nose cone 8 (e.g., within the cavity 9 of the nose cone 8) and the arterial implant segment 18 (i.e., the distal end of the arterial implant segment 18 keeping with prior convention) abutting the distal end of the middle shaft 16.

Figure 29:
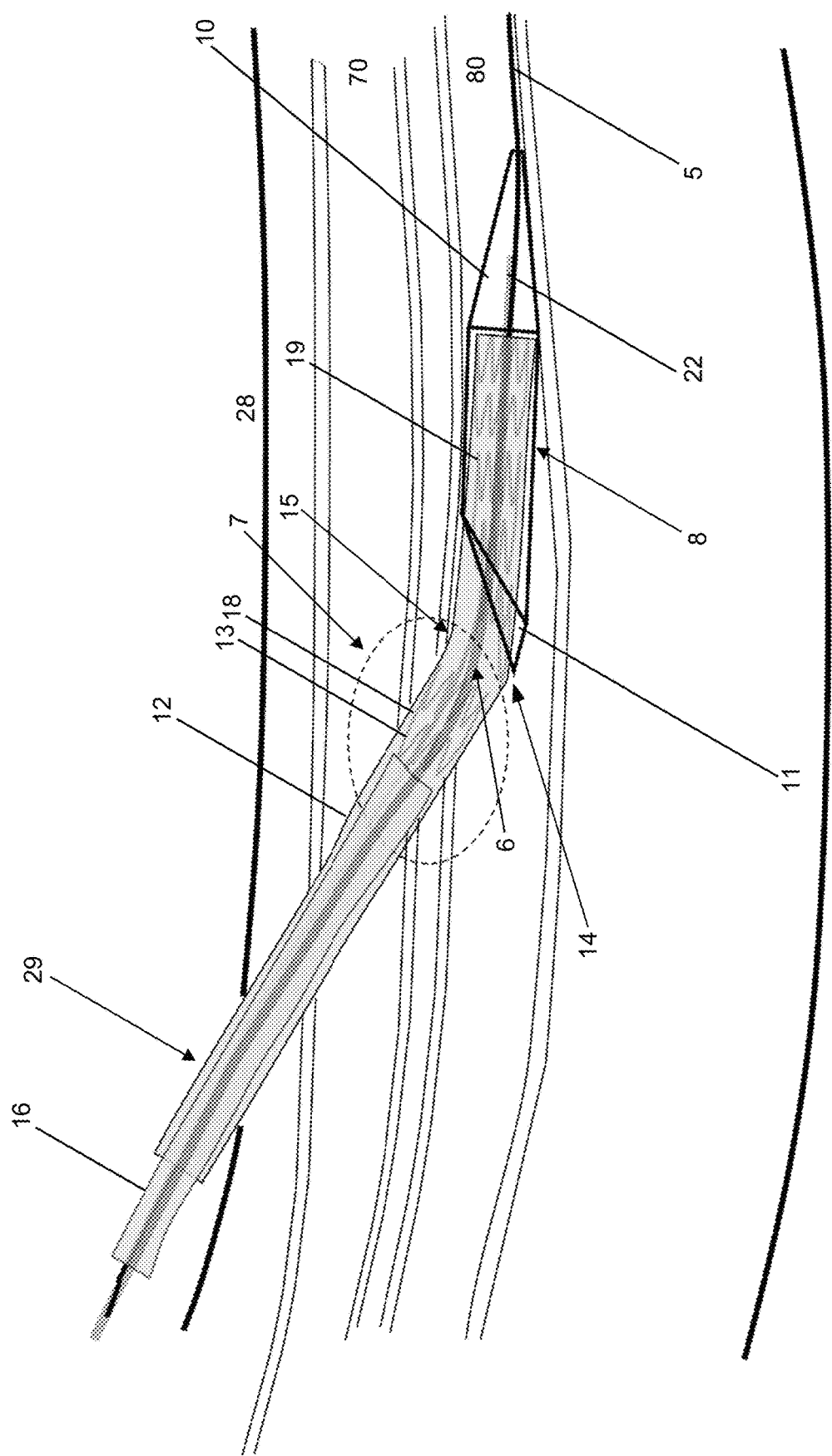

FIG. 29 depicts the nose cone 8 of delivery device 29 advanced across the AVF location 7 and within vein 80. Also shown is the gap 14 which may form when the delivery device 29 follows guidewire curvature 6 and the nose cone 8 and the outer sheath 12 are no longer coaxial. The gap 14 can be defined in some embodiments as an open space between the proximal opening of the nose cone 8 (e.g., the proximal opening of cavity 9 of nose cone 8) and a sidewall of the outer sheath 12 as it enters the proximal opening (e.g., cavity 9) of the nose cone 8. In some embodiments, the gap 14 defines about, at least about, or no more than about 5%, 10%, 15%, 20%, 25%, 30%, 35%, 40%, 45%, 50%, or more or less in length and/or diameter of the respective length and/or diameter of the proximal opening (e.g., cavity 9) of the nose cone 8, or ranges including any two of the foregoing values. Of note and as shown, to form the gap 14 the nose cone 8 may need to be oriented as shown in FIG. 29, e.g., with its longer trailing proximal end (created due to the proximal end being at an angle with the longitudinal length of the nose cone in some embodiments as shown) being oriented on the outside of the curve 6. Further shown, the angle 15 between the central (e.g., longitudinal) axis of nose cone 8 and the central (e.g., longitudinal) axis of outer sheath 12 may form when the nose cone 8 at the distal end of delivery device 29 is in the curved configuration as shown in FIG. 29 and oriented the same as way as to form gap 14. In some embodiments, the angle 15 can be, for example, about, at least about, or no more than about 5, 10, 15, 20, 25, 30, 35, 40, 45 degrees, or more or less, and ranges including any two of the foregoing values. To facilitate greater flexibility between nose cone 8 and outer sheath 12, nose cone 8 may have a slit in the wall that forms cavity 9. In some embodiments, to facilitate greater flexibility between nose cone 8 and outer sheath 12, cavity 9 of the nose cone 8 may be oversized relative to the outer diameter of the outer sheath 12. In some embodiments, the curvature 6 of guidewire 5 may be used to form angle 15 and gap 14. Alternative means of forming angle 15 and gap 14 can be utilized. An alternative embodiment could be, for example, to use one, two, or more pull wires to deflect the distal end of delivery device 29 so that gap 14 is formed. A wide variety of steerable and/or deflectable elements can be utilized depending on the desired clinical result. In some embodiments, a gap 14 may not be formed and/or be required.

Figure 30:
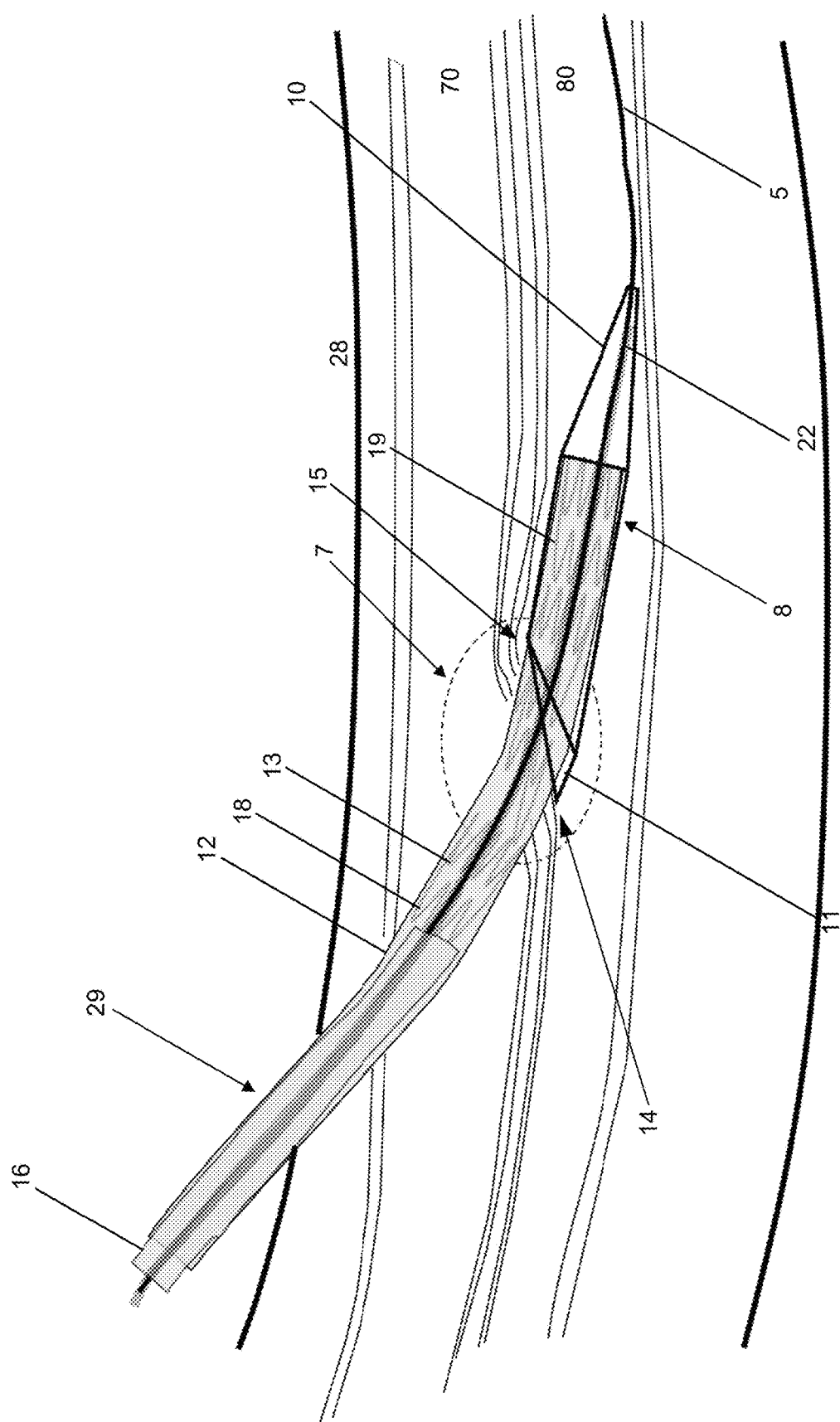

FIG. 30 depicts the nose cone 8 engaging the near wall of the vein 80 after delivery device 29 has been pulled proximally from its location in FIG. 29 according to some embodiments. The engagement between nose cone 8 (e.g., the proximal end of nose cone 8) and the near wall of the vein 80 may be due to the gap 14 which formed when delivery device 29 was urged into a curved configuration with the tapered proximal end 11 (e.g., the longer trailing proximal end) on the outside of the curvature. In some embodiments, no gap 14 is required for the engagement between nose cone 8 (e.g., the tapered proximal end 11 of nose cone 8) and the near wall of the vein 80. For example, the tapered proximal end 11 of the nose cone 8 may engage the near wall of the vein 80 upon the delivery device 29 being pulled proximally. Also depicted is the deformation of the anatomy at AVF location 7, which is a result of the apposition forces between the near wall of the vein 80 and the tapered proximal end 11 of the nose cone 8. This deformation of the anatomy at AVF location 7 may be visualized by ultrasound and used to verify proper tissue engagement and/or implant placement before delivery.

Figure 31:
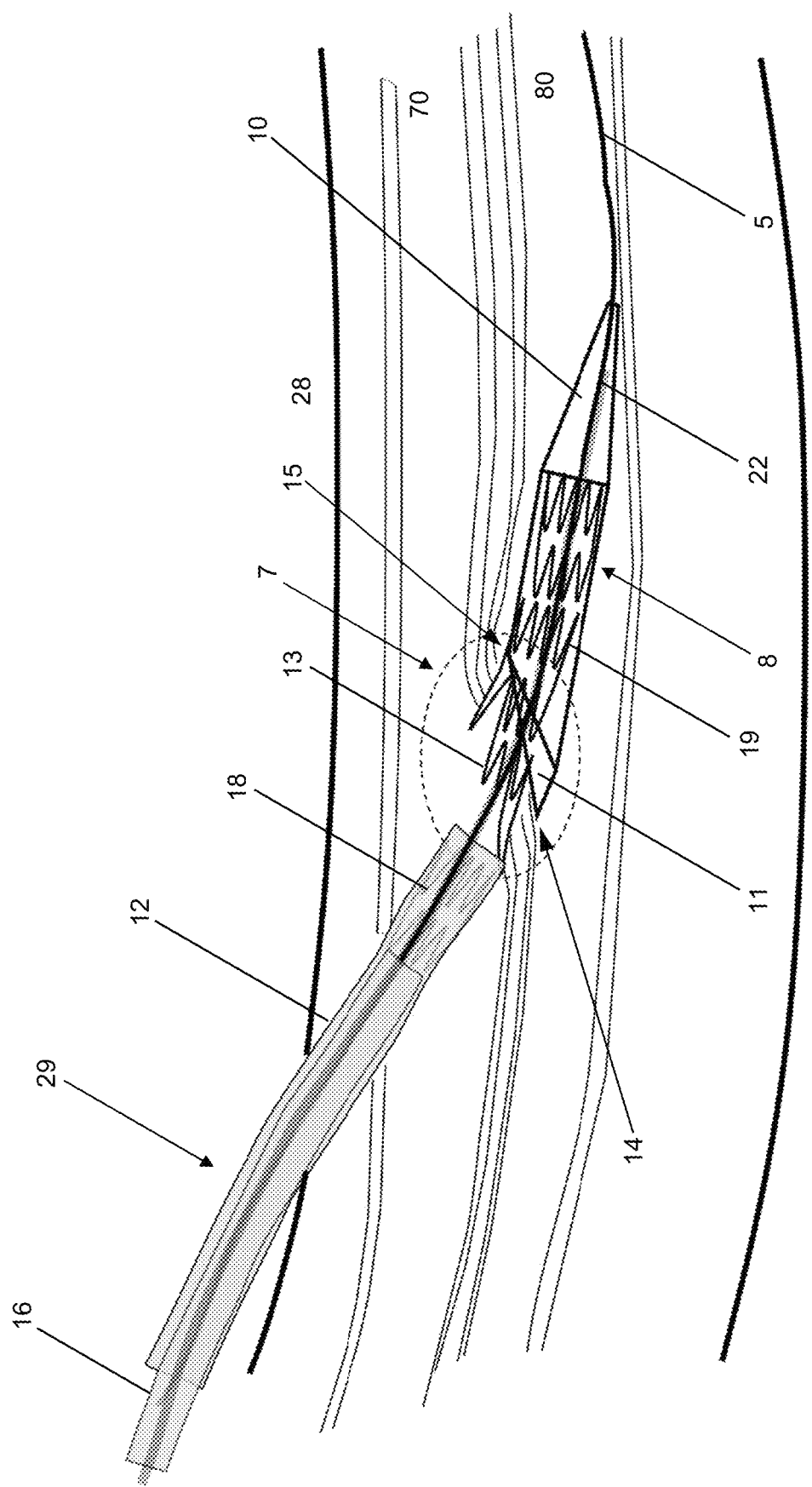

FIG. 31 depicts an initial step of the first stage of delivery of the radially compressed (e.g., elastically constrained) implant 13 according to some embodiments. While nose cone 8 is held in apposition against the near wall of vein 80, the outer sheath 12 may be retracted proximally so that the radially compressed implant 13 is allowed to expand with the precise location defined due to the engagement between nose cone 8 and the near wall of the vein 80. The distal end of the middle shaft 16 may be held fixed during retraction of the outer sheath 12 so that the radially compressed implant 13 does not slip proximally during the retraction of the outer sheath 12. Also depicted is the venous implant segment 19 being held at least partially constrained by cavity 9 of the nose cone 8, which can occur upon retraction of the outer sheath 12 (e.g., the outer sheath 12 no longer keeps the venous implant segment 19 radially compressed, so the venous implant segment 19 expands into the cavity 9). In some embodiments and also depicted is a portion of the venous implant segment 19 (e.g., the distal end but here oriented proximally) radially expanding at AVF location 7 due to the radial stiffness of the implant 13. Also depicted is the arterial implant segment 18 still radially compressed within the outer sheath 12. To retract the outer sheath 12, the control knob 26 of the delivery device 29 may be slid proximally from its distal most position with initial delivery of the implant 13 while the handle 23 of the delivery device 29 is held in position to maintain the nose cone 8 in apposition against the near wall of vein 80. In some embodiments, the middle shaft 16 may be held fixed during retraction of the outer sheath 12 by the middle shaft connector 50 being prevented from moving proximally by its interaction with middle shaft connector stop 52 of the delivery device 29.

Figure 32:
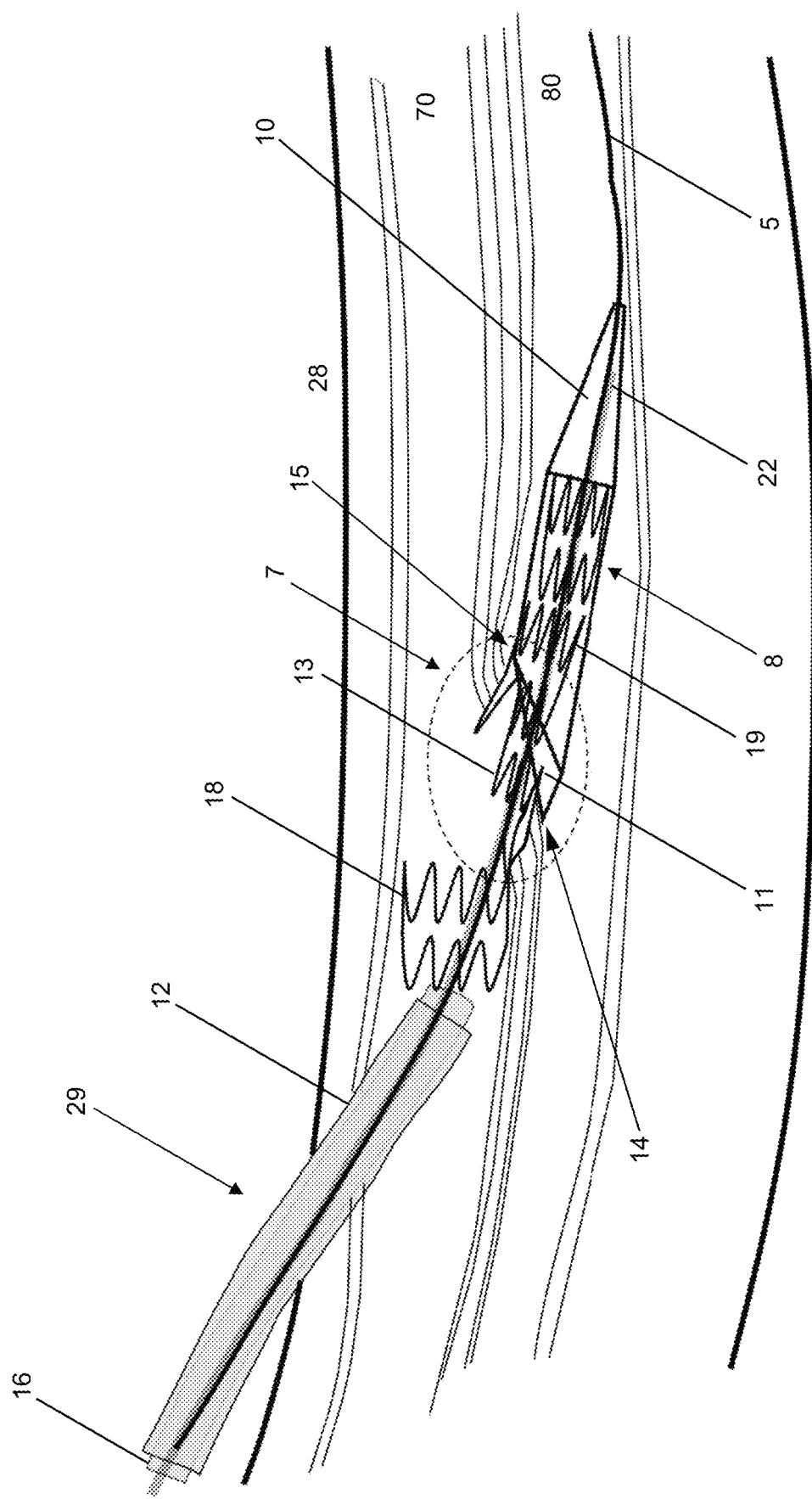

FIG. 32 depicts the continuing delivery of the radially compressed (e.g., elastically constrained) implant 13 with further retraction of the outer sheath 12 until the arterial implant segment 18 is fully released from the outer sheath 12 according to some embodiments. As shown, upon full retraction of the outer sheath 12, the arterial implant segment 18 may radially expand within the artery 70. Upon radially expanding within the artery 70, the arterial implant segment 18 may radially engage the wall of the artery 70. Also shown and in some embodiments, upon full retraction of the outer sheath 12, the arterial implant segment 18 may form an angle relative to the venous implant segment as described herein (e.g., the longitudinal axis of the arterial implant segment 18 may form an angle relative to the longitudinal axis of the venous implant segment 19). To further retract the outer sheath 12, the control knob 26 of the delivery device 29 may be slid further proximally to its proximal most position while the handle 23 of the delivery device 29 is held in position to maintain the nose cone 8 in apposition against the near wall of vein 80. In some embodiments, the middle shaft 16 may be held fixed during retraction of the outer sheath 12 by the middle shaft connector 50 being prevented from moving proximally by its interaction with middle shaft connector stop 52 of the delivery device 29. It is to be understood that while the actions of FIG. 31 and FIG. 32 have been described discretely, in practice the actions depicted and described in FIG. 31 and FIG. 32 may follow one another in a smooth fashion. For example, the outer sheath 12 may be retracted fully in one motion by movement (e.g., sliding) of the control knob 26 of the delivery device 29 from its initially distal most position to its proximal most position, which may fully release the implant 13 from the outer sheath 12 in the one motion.

Figure 33:
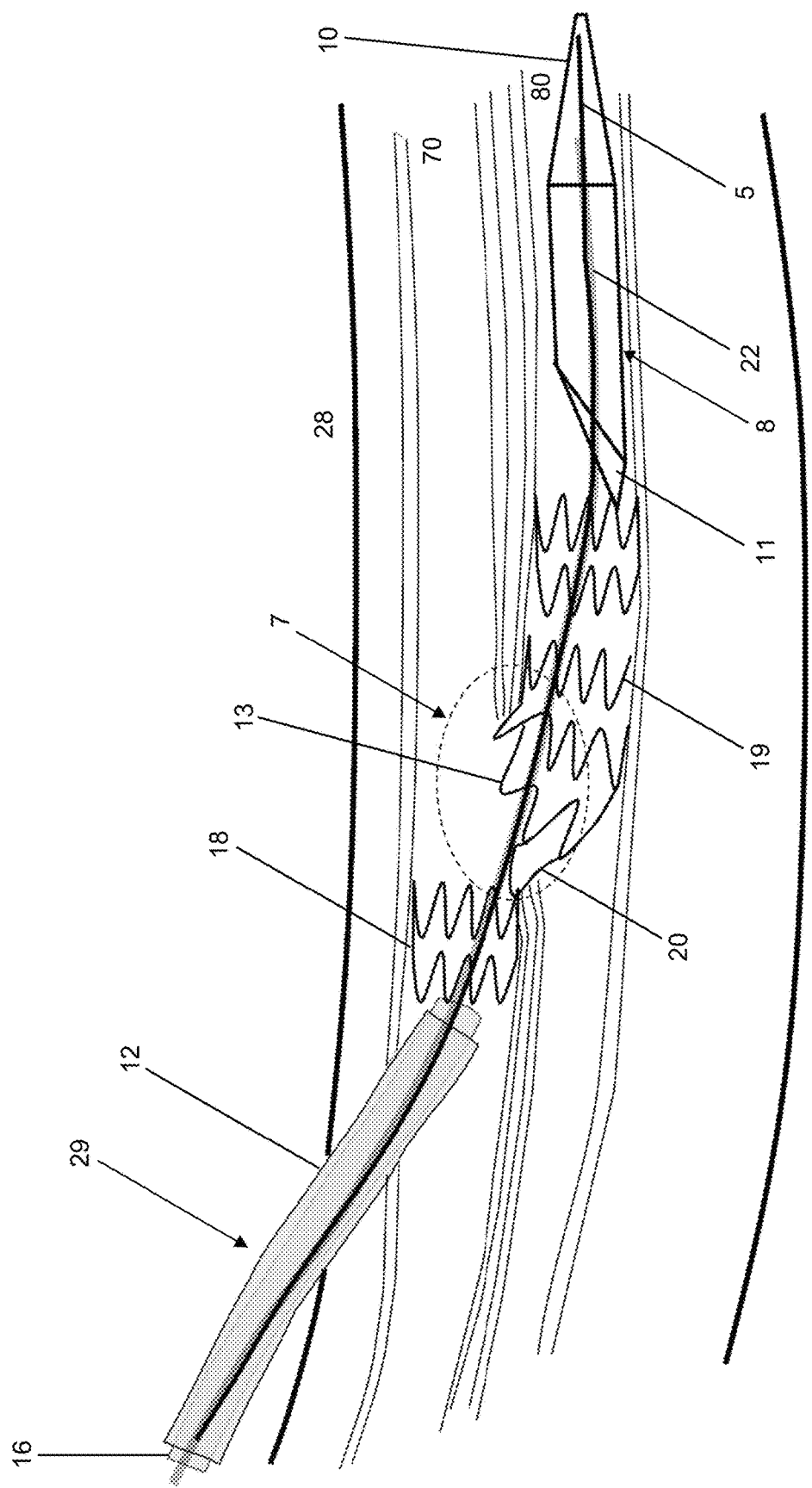

FIG. 33 depicts the delivery of the radially compressed (e.g., elastically constrained) venous implant segment 19 according to some embodiments. As shown, when nose cone 8 is advanced distally by advancing guidewire shaft 22 distally (e.g., by advancing the delivery device 29 distally), the venous implant segment 19 may be held in place by connector struts 20 connected to the arterial implant segment 18 and is thus slidably released from cavity 9 of the nose cone 8. Furthermore and as shown, when the venous implant segment 19 is released from cavity 9, it may radially expand within the vein 80. Upon radially expanding within the vein 80, the venous implant segment 19 may radially engage the wall of the vein 80. Also as shown, the arterial implant segment 18 may provide a means of securing the most distal portion of the distal edge (as oriented here the most proximal portion of the proximal edge) of the venous implant segment 19 so that it does not encroach into the luminal space of artery 70. Additionally as shown, upon radially expanding, the distal end (as oriented here the proximal end) of the venous implant segment 19 may radially expand at the far wall of the artery 70 and form a fluidic seal with the far wall of the artery 70. The arterial implant segment 18 may also provide radial support for the artery 70 to ensure patency and sufficient blood flow in the artery 70 after implantation of the implant 13.

Figure 34:
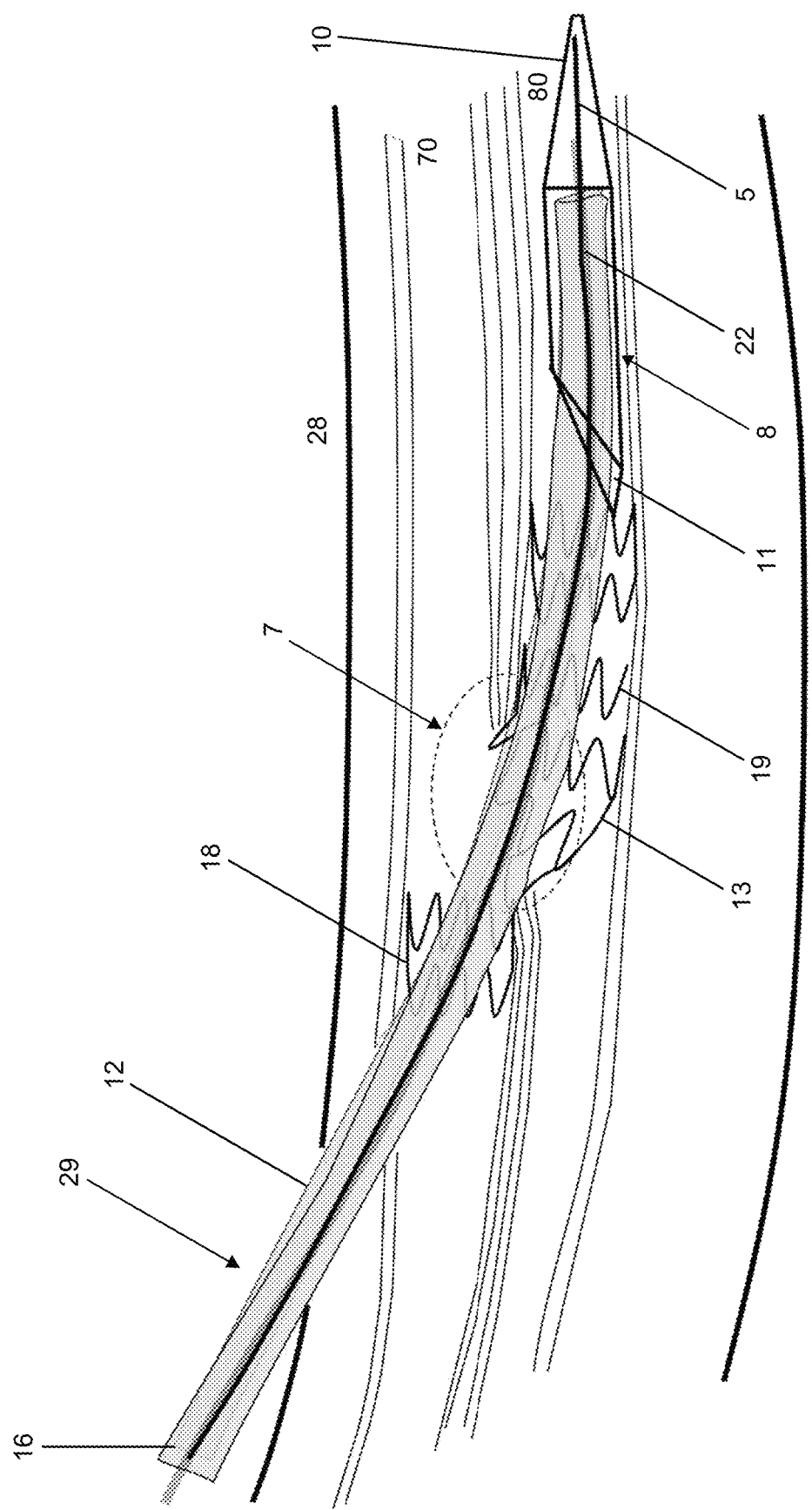

FIG. 34 depicts the initial step of removal of the delivery device 29 with the advancement of the outer sheath 12 and the middle shaft 16 distally through the delivered (e.g., radially expanded) implant 13 and into cavity 9 of the nose cone 8 according to some embodiments. In some embodiments, the middle shaft 16 may lead the outer sheath 12 during this advancement step to facilitate reliable engagement of the outer sheath 12 into the cavity 9 without the outer sheath 12 catching the proximal end 11 of the nose cone 8. To move/advance the outer sheath 12 distally, the control knob 26 of the delivery device 29 may be moved (e.g., slid) distally to its distal most position within handle 23 while the handle 23 of the delivery device 29 is maintained in position. Furthermore and in some embodiments, the middle shaft 16 may be made to lead and advance with the outer shaft 12 by the middle shaft connector 50 engaging with the control knob 26 after the control knob 26 has been moved (e.g., slid) into its proximal most position from an earlier step in the delivery process and the middle shaft connector 50 moving distally with the control knob 26 upon the control knob 26 being moved distally.

Figure 35:
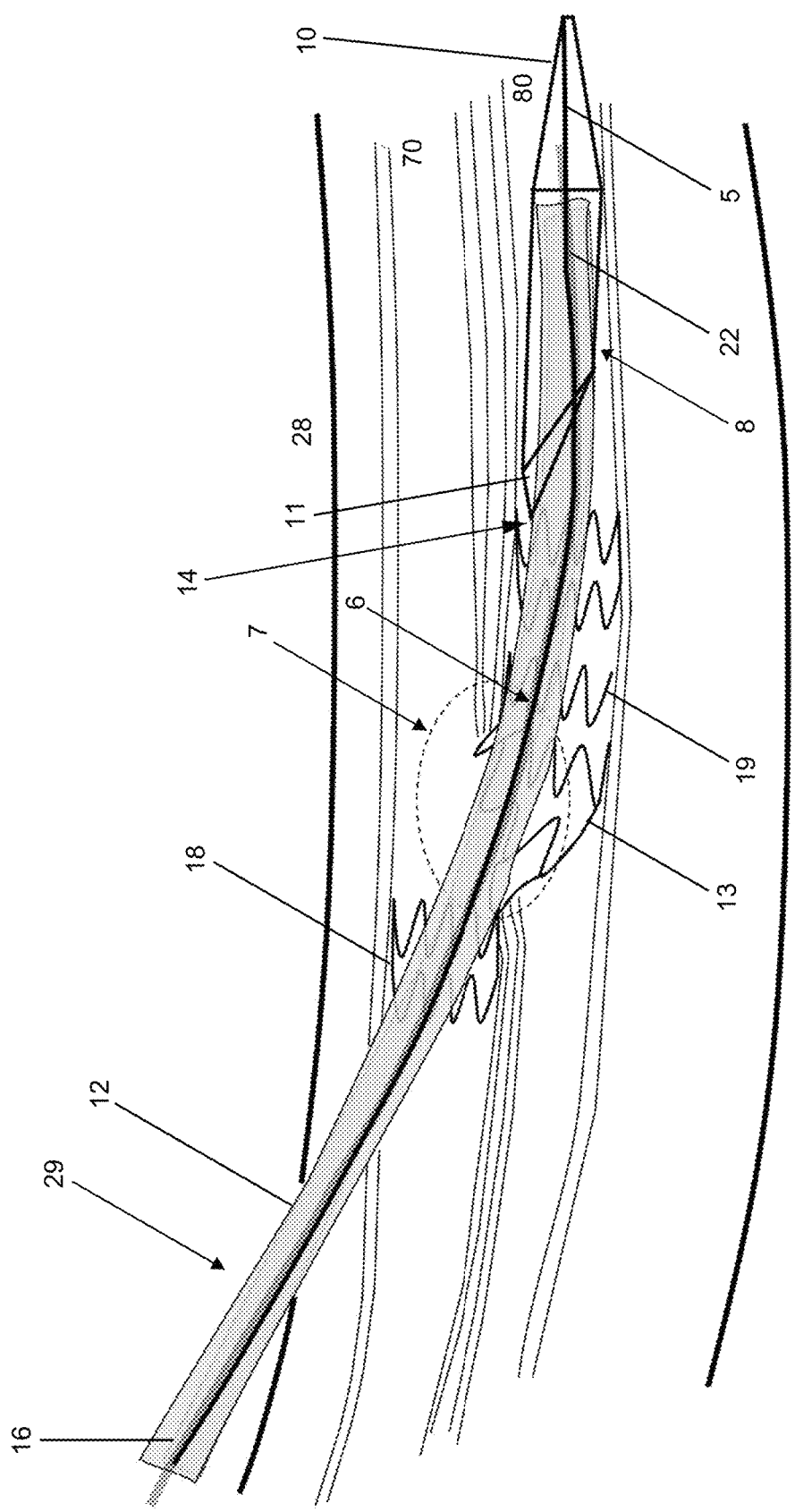

FIG. 35 depicts a continuation of the removal of the delivery device 29 with the rotation of the delivery system 29 around its axis of, e.g., approximately 180 degrees such that the proximal portion of the tapered proximal end 11 of the nose cone 8 is on the inside of curvature 6 according to some embodiments. In this orientation, the gap 14 may be minimized, eliminated, or substantially eliminated and there may be flush contact between the proximal tapered end 11 and the outer sheath 12. This low-profile configuration may facilitate removal of the nose cone 8 without engagement of the delivered implant 13 or any of the anatomical features near AVF location 7. In some embodiments, the engagement between the outer sheath 12 and the proximal end of the nose cone 8 may follow as shown and described relative to FIG. 10B herein, e.g., the proximal tapered end of the nose cone 8 may be received within the lumen of the outer sheath 12 upon advancement of the outer sheath 12 distally, creating a smooth transition between the outer sheath 12 and the proximal end of the nose cone 8 and thus aiding in removal of the delivery device 29.

Figure 36:
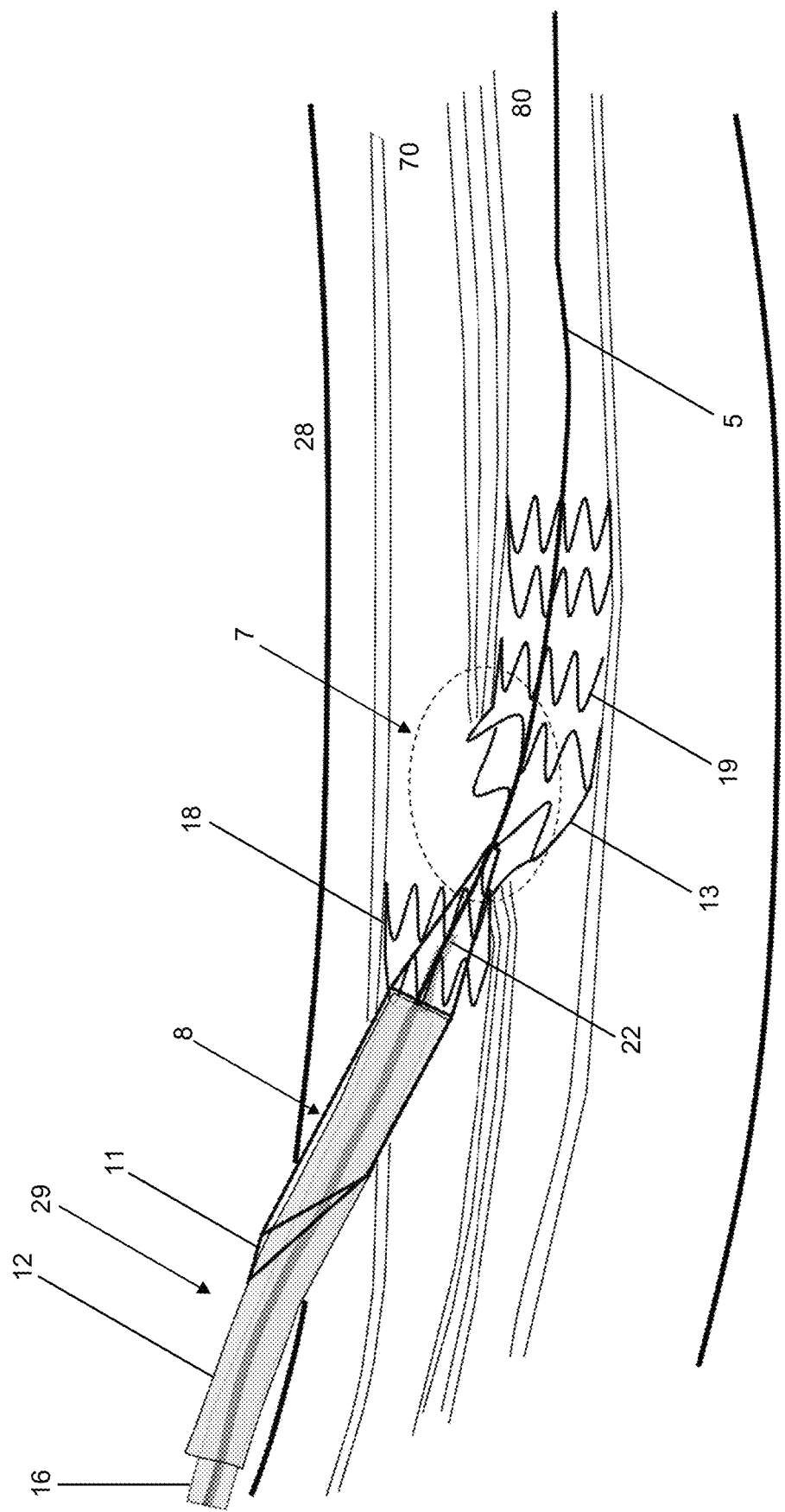

FIG. 36 depicts a continuation of the removal of the delivery device 29 according to some embodiments. As shown, with proximal retraction of the delivery device 29, the nose cone 8 has passed through the majority of the implant 13 without interference. The implant 13 may have unconstrained (e.g., radially expanded) delivered internal dimensions that are greater than the outer dimension of nose cone 8 so that nose cone 8 does not experience excessive resistance or interference with the implant 13 upon removal through implant 13. In some embodiments and as described relative to FIG. 13 herein, if the gap 14 has formed again during retraction of the delivery device 29, the delivery device can be rotated again to minimize and/or eliminate the gap 14 to facilitate delivery device 29 removal.

Figure 37:
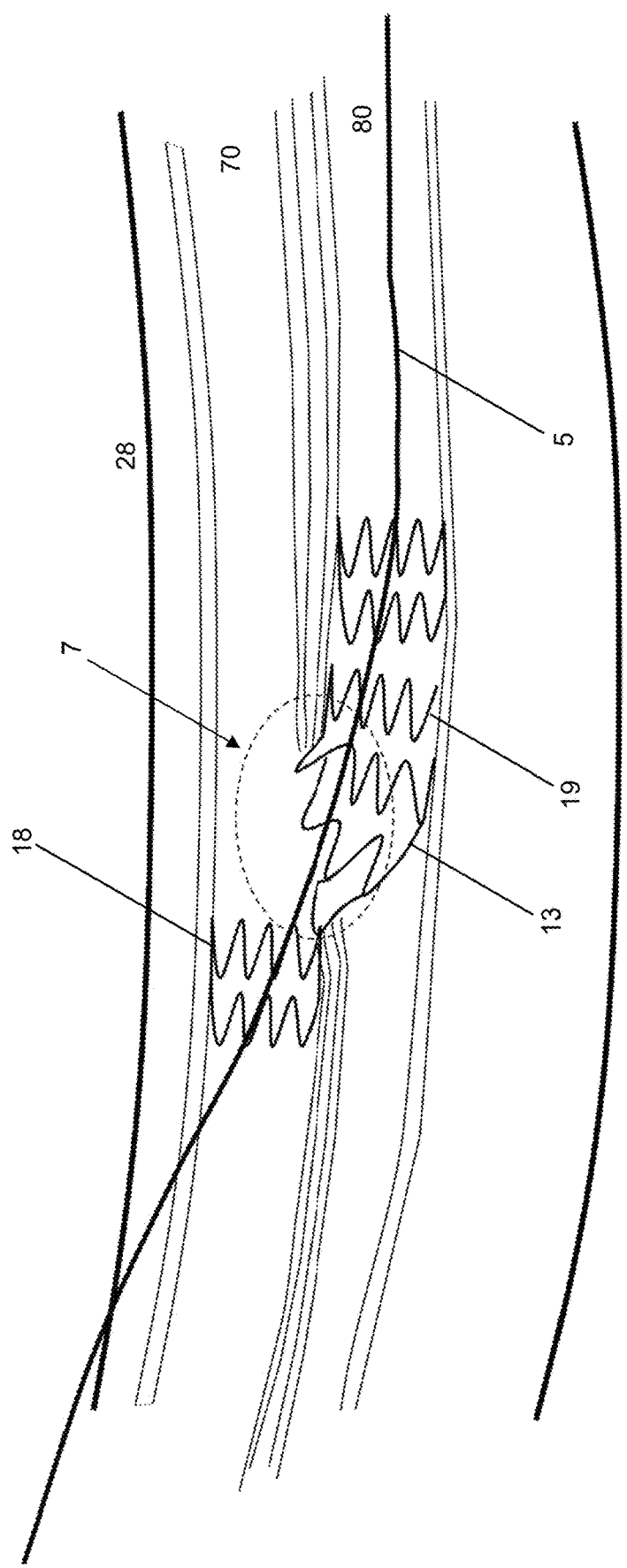

FIG. 37 depicts the complete removal of the delivery device 29 and only the guidewire 5 remaining according to some embodiments. Prior to removal of the guidewire 5, it may be desirable or advantageous to advance a balloon dilation catheter appropriately sized for implant 13 and the vasculature to facilitate complete expansion of the implant 13. In some embodiments with a venous implant segment 19 and an arterial implant segment 18 of different diameters, cross-sectional areas, and/or perimeters, balloon dilation catheters of different sizes may be used to facilitate complete expansion of the venous implant segment 19 and an arterial implant segment 18.

Figure 38:
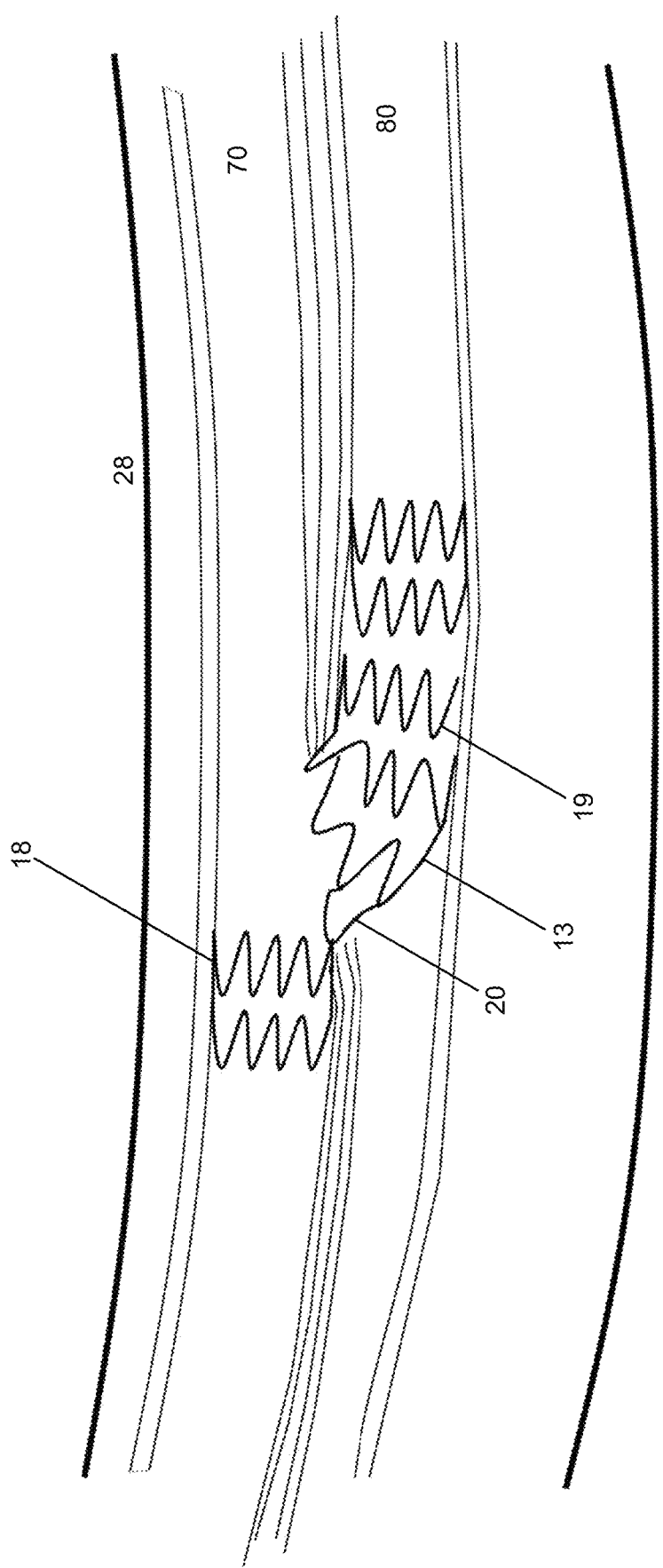

FIG. 38 depicts the completed delivery of the implant 13 with the arterial implant segment 18 in the artery 70, the venous implant segment 19 in the vein 80, and the venous implant segment 19 forming an AVF between the artery 70 and the vein 80. As described herein, the implant 13 may be at least partially anchored in place by any one or more of: (i) the engagement between the wall of the artery 70 and the radially expanded arterial implant segment 18; (ii) the engagement between the wall of the vein 80 and the radially expanded venous implant segment 19; (iii) the engagement between any anatomical structures, such as any portion of the walls of the artery 70 and/or vein 80, and any anchor(s) and/or barb(s) of the implant 13 (not shown in FIG. 38); and (iv) the engagement between the far wall of the artery 70 and the continuous strut/ring 21 (e.g., anastomotic ring) of the implant 13 in embodiments wherein the implant 13 comprises a continuous strut/ring 21. As shown and as described herein, the distal end (as oriented here the proximal end) of the venous implant segment 19 may not obstruct the lumen of artery 70. In some embodiments, the arterial implant segment 18, through connector struts 20, may locate the venous implant segment 19 such that the distal end (as oriented here the proximal end) of the venous implant segment 19 may not obstruct the lumen of artery 70. In embodiments wherein the implant 13 comprises a continuous strut/ring 21, the continuous strut/ring 21 may form a fluidic seal with the far wall of the artery 70. Also shown in FIG. 38 and as described herein, in some embodiments, the venous implant segment 19 (e.g., an axis, such as the longitudinal axis, of the venous implant segment) may be at an angle of between about 0 degrees to about 90 degrees with respect to the arterial implant segment 18 (e.g., an axis, such as the longitudinal axis, of the arterial implant segment). Furthermore, the implant 13 may comprise any one or more of the features, sizes, characteristics, or the like of any of the embodiments of an implant 13 as described herein.

Referring to FIG. 23, prior to implantation of the implant 13, blood flow in the artery 70 may be from right to left, and blood flow within the vein 80 may be from left to right. Referring to FIG. 38, after implantation of the implant 13, blood flow may be as follows: blood flow in the artery 70 may be from right to left and enter the side opening or port (e.g., the side opening or port between the venous implant segment 19 and the arterial implant segment 18) of the implant 13 as shown and (i) flow through the proximal end (as oriented here, distal end) of the arterial implant segment 18 and out the distal end (as oriented here, proximal end) of the arterial implant segment 18 to continue through the artery, and (ii) flow through the distal end (as oriented here, proximal end) of the venous implant segment 19 and out the proximal end (as oriented here, distal end) of the venous implant segment 19 to flow into the vein 80 (and, e.g., flow from left to right in the vein 80 after exiting the venous implant segment 19). In some embodiments and with continued reference to FIG. 38, after implantation of the implant 13 as shown, blood flow through the vein 80 may be at least partially blocked or completely blocked by the venous implant segment 19 (e.g., the blood flow from left to right to the left of the implant 13). Arterial blood may flow through the venous implant segment 19 of the implant 13 due to the pressure differential between the artery 70 and the vein 80. The flow of arterial blood in the vein 80 due to the implant 13 may advantageously cause the vein to increase in at least one of its size (e.g., diameter), thickness, and blood flow rate. For example, the flow of arterial blood in vein 80 due to the implant 13 may advantageously cause the vein 80 to increase in diameter to at least about 4 mm, at least about 5 mm, or at least about 6 mm. In another example, the flow of arterial blood in the vein 80 due to the implant 13 may advantageously cause the blood flow in the vein 80 to be at least about 400 cc/min, at least about 500 cc/min, or at least about 600 cc/min. In some embodiments, the implant 13 may lead the vein 80 to develop into a point of single access for hemodialysis. In some embodiments, the implant 13 may lead the vein 80 to develop a diameter of at least about 6 mm and a blood flow rate of at least about 600 cc/min.

The methods and devices described through FIGS. 23-38 may apply to the creation of an AVF in the vasculature of any relevant area of the human body and for any purpose, including but not limited to the creation of an access point for hemodialysis. For example, the methods and devices described through FIGS. 23-38 may apply to the creation of an AVF between a femoral artery and a femoral vein.

Figure 39:
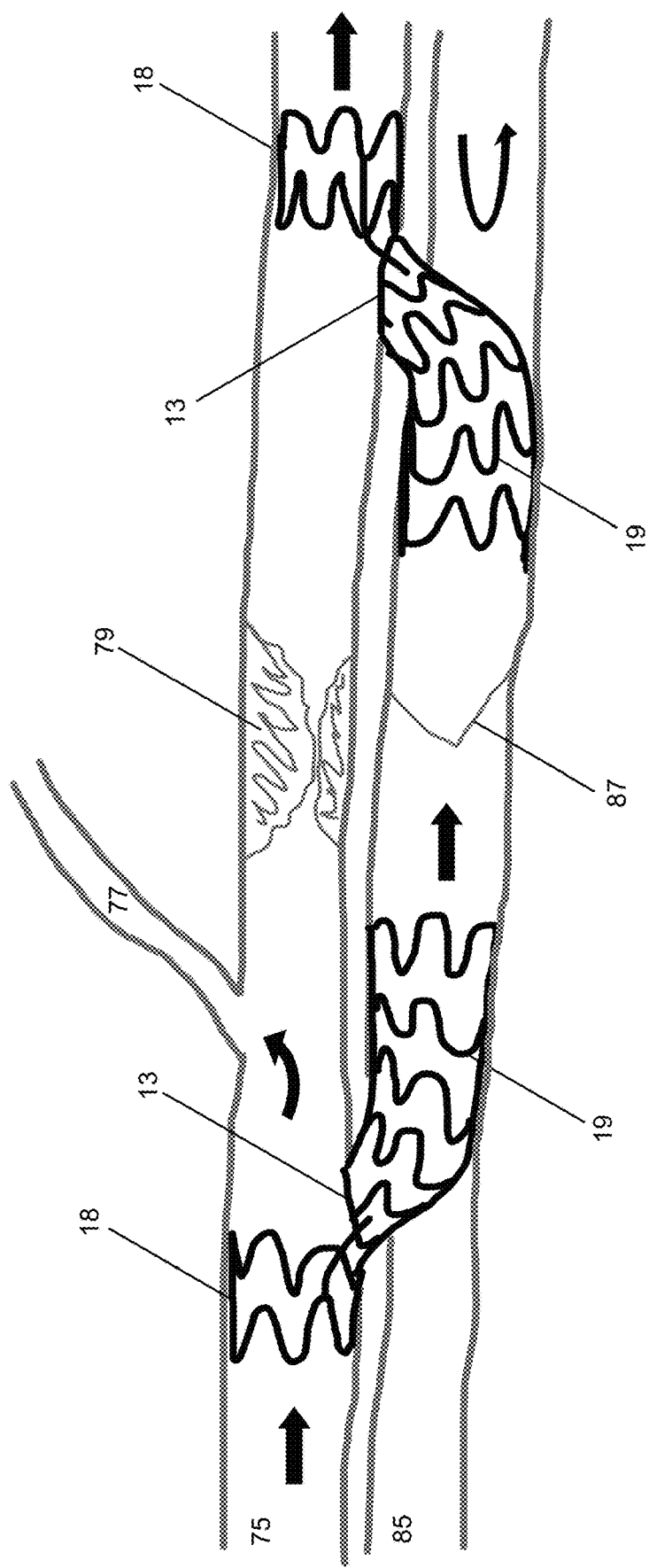
FIG. 39 depicts a method of bypassing a section of an artery with endovascular implants according to some embodiments.

FIG. 39 depicts a method of bypassing a section of an artery with endovascular implants according to some embodiments. Shown is an artery 75 with an arterial branch 77 and an arterial occlusion 79. Also shown is a vein 85 adjacent the artery 75, which may in some embodiments include a vein valve 87. Also shown are two implants 13 implanted such that one (e.g., the left one) creates an AVF between the artery 75 and the vein 85 to the left of (e.g., upstream) of the arterial occlusion 79, and one (e.g., the right one) creates an AVF between the artery 75 and the vein 85 to the right of (e.g., downstream) of the arterial occlusion 79.

Prior to the implantation of the implants 13, blood flow in the artery 75 may be from left to right and may be blocked, substantially blocked, or partially blocked by the arterial occlusion 79, preventing the normal flow of blood through the artery 75. The arterial branch 77 may receive blood flow from the artery, as indicated by the arrow in FIG. 39, as it is positioned to the left (e.g., upstream) of the arterial occlusion 79. Also prior to the implantation of the implants 13, blood flow in the vein 85 may be from right to left, and if a vein valve 87 is present the blood may flow through the vein valve 87 in the same direction.

After the implantation of the implants 13 as shown, arterial blood flow may be as follows: blood flow in the artery 75 may be from left to right and flow through the distal end (per the convention used herein) of the arterial segment 18 of the left implant 13 and out the proximal end (per the convention used herein) of the arterial segment 18 of the left implant 13 and (i) continue to flow through the artery from left to right and either flow through the arterial branch 77 or be blocked by the arterial occlusion 79, and (ii) flow through the distal end (per the convention used herein) of the venous segment 19 and out the proximal end (per the convention used herein) of the venous segment 19 to flow into the vein 85. If a vein valve 87 is positioned in the vein 85 as shown between the left implant 13 and the right implant 13, before or during implantation of the implants a valvulotome or other device may be used to destroy the vein valve 87 so that after implantation of the implants, the arterial blood directed to the vein 85 from the artery 75 by the left implant 13 may continue past the (now destroyed) vein valve 87. Continuing with the arterial blood flow after being directed to the vein 85 by the left implant 13 and any interfering vein valves 87 being destroyed, the arterial blood flow may continue as follows: the arterial blood may continue through the vein 85 after flowing through the venous implant segment 19 of the left implant 13, past any destroyed vein valves 87 if present, flow through the proximal end of the venous implant segment 19 of the right implant 13, flow out of the distal end of the venous implant segment 19 of the right implant 13, flow through the side opening or port of the right implant 13, and (i) flow to the left towards the arterial occlusion 79 before being blocked by the arterial occlusion 79, and (ii) flow to the right through the proximal end of the arterial implant segment 18 of the right implant and out the distal end of the arterial implant segment 18 of the right implant and continue through artery 75. In this way, two implants 13 may be used to restore arterial blood flow in an artery with an arterial occlusion 79. After the implantation of the implants 13 as shown, venous blood flow in the vein 85 may be blocked by the venous implant segment 19 of the right implant 13 as indicated by the return arrow in FIG. 39. The two implants 13 may be covered with a graft material as described herein to facilitate the re-direction of blood flow as discussed relative to FIG. 39.

In continued reference to FIG. 39, in some embodiments the venous implant segment 19 of an implant 13 may traverse a vein valve 87 and obviate the need to destroy the vein valve 87 prior to implantation (e.g., the radial stiffness of the implant may alone be sufficient to open the vein valve 87 and allow for desired blood flow through the vein valve 87). In some embodiments, the delivery device 29 comprises enough axial stiffness to traverse a vein valve 87 and allow for a venous implant segment 19 of the implant 13 to be implanted across the vein valve 87. In some embodiments, the two implants 13 may be overlapped, for example, the venous implant segment 19 of the left implant may be implanted within the venous implant segment 19 of the right implant or vice versa. In some embodiments, the two implants 13 may be spaced apart taking into consideration the vascular anatomy (such as any arterial branches 77) and any arterial occlusions 79. Any of the delivery methods described herein may be used to implant more than one implant 13 as shown in FIG. 39, including the methods described relative to FIGS. 1-15 wherein the delivery device may first access a vein before an artery and the methods described relative to FIGS. 23-38 wherein the delivery device may first access an artery before a vein. Furthermore and as shown in and described relative to FIG. 39, an implant 13 may be used to divert blood flow within the body in multiple ways and is not limited to any one description provided herein. For example, blood flow may enter or exit the distal end of the distal implant segment 18 (i.e., arterial implant segment 18), blood flow may enter or exit the side opening or port between the proximal end of the distal implant segment 18 (i.e., arterial implant segment 18) and the distal end of the proximal implant segment 19 (venous implant segment 19), blood flow may enter or exit the proximal end of the distal implant segment 18 (i.e., arterial implant segment 18), blood flow may enter or exit the distal end of the proximal implant segment 19 (i.e., venous implant segment 19), and blood flow may enter or exit the proximal end of the proximal implant segment 19 (i.e., venous implant segment 19).

As described herein, delivery system 29 may be used interchangeably with delivery device 29. Also as described herein, distal implant segment 18 may be used interchangeably with arterial implant segment 18. Also as described herein, proximal implant segment 19 may be used interchangeably with venous implant segment 19. In some embodiments, the delivery device 29 may be configured to percutaneously deliver the implant 13 into the patient. In some embodiments, the delivery device 29 may be configured to deliver the implant 13 into the patient after a surgical cut down to the AVF location and/or to near the AVF location.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Where term "about" is utilized before a range of two numerical values, this is intended to include a range between about the first value and about the second value, as well as a range from the first value specified to the second value specified.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems, devices, and methods for endovascular implants and accurate placement thereof have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems, devices and methods for endovascular implants and accurate placement thereof. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of endovascular implants and devices and methods for accurate placement have been disclosed. Although the systems, devices and methods for endovascular implants and accurate placement thereof have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A method of creating an arteriovenous fistula in a patient, comprising:
   delivering an intraluminal implant in a collapsed configuration into the patient, the intraluminal implant comprising a proximal implant segment and a distal implant segment, wherein the proximal implant segment is connected to the distal implant segment, and wherein the intraluminal implant comprises a side opening between a distal end of the proximal implant segment and a proximal end of the distal implant segment;
   extending the intraluminal implant between a vein and an artery, wherein the proximal implant segment extends at least partially through the vein and the distal implant segment is positioned within the artery; and
   radially expanding the proximal implant segment to cause the proximal implant segment to engage a wall of the vein and radially expanding the distal implant segment to cause the distal implant segment to engage a wall of the artery and provide radial support for the artery, such that the proximal implant segment does not substantially obstruct a lumen of the artery, and such that blood flowing through the artery enters the intraluminal implant through the side opening and is diverted from the artery along the proximal implant segment.

2. The method of claim 1, wherein blood flowing through the artery enters the side opening and (i) flows through the proximal end of the distal implant segment and a distal end of the distal implant segment to continue through the artery, and (ii) flows through the distal end of the proximal implant segment and out a proximal end of the proximal implant segment to flow into the vein.

3. The method of claim 1, wherein the proximal implant segment and the distal implant segment comprise tubular bodies.

4. The method of claim 1, further comprising anchoring a distal end of the proximal implant segment to the wall of the artery.

5. The method of claim 1, wherein after the proximal implant segment is radially expanded to engage the wall of the vein and the distal implant segment is radially expanded to engage the wall of the artery, the proximal implant segment is angled relative to an axis of the distal implant segment.

6. The method of claim 5, wherein the proximal implant segment is angled relative to an axis of the distal implant segment by between about 0 degrees to about 90 degrees.

7. The method of claim 1, wherein the intraluminal implant is delivered into the patient within a sheath constraining the intraluminal implant at a distal end of the sheath.

8. The method of claim 7, wherein the distal end of the sheath is advanced into the artery within a cavity of a nose cone.

9. The method of claim 8, wherein the proximal implant segment is released from the sheath to radially expand into engagement with the wall of the vein by proximally retracting the sheath relative to the nose cone.

10. The method of claim 9, wherein the distal implant segment is radially expanded into engagement with the wall of the artery by distally advancing the nose cone relative to the distal implant segment.

11. The method of claim 10, further comprising distally advancing the sheath through the radially expanded proximal implant segment and the radially expanded distal implant segment into engagement with the nose cone, and proximally retracting the sheath engaged with the nose cone through the radially expanded proximal implant segment and the radially expanded distal implant segment.

12. The method of claim 9, further comprising engaging a proximal end of the nose cone with a wall of the artery while the sheath is proximally retracted to release the proximal implant segment.

13. The method of claim 11, wherein the nose cone is rotated within the artery after the nose cone has been distally advanced to release the distal implant segment and before proximally retracting the sheath engaged with the nose cone through the radially expanded proximal implant segment and the radially expanded distal implant segment.

14. The method of claim 1, wherein the distal implant segment is positioned within the artery downstream of the side opening in regard to a direction of arterial blood flow.

15. The method of claim 1, wherein all blood diverted from the artery is directed along the proximal implant segment and into a superficial vein.

16. The method of claim 1, wherein the intraluminal implant comprises a continuous ring at the distal end of the proximal implant segment to increase a radial stiffness of the distal end of the proximal implant segment.

17. The method of claim 1, wherein after the distal implant segment is radially expanded to engage the wall of the artery, the distal implant segment, by its connection to the proximal implant segment, prevents the proximal implant segment from obstructing the lumen of the artery.

18. A method of creating an arteriovenous fistula in a patient, comprising:
    delivering an intraluminal implant in a collapsed configuration into the patient, the intraluminal implant comprising a proximal implant segment and a distal implant segment, wherein the proximal implant segment is connected to the distal implant segment, and wherein the intraluminal implant comprises a side opening between a distal end of the proximal implant segment and a proximal end of the distal implant segment;
    extending the intraluminal implant between a vein and an artery, wherein the proximal implant segment extends at least partially through the vein and the distal implant segment is positioned within the artery downstream of the side opening in regard to a direction of arterial blood flow; and
    radially expanding the proximal implant segment to cause the proximal implant segment to engage a wall of the vein and radially expanding the distal implant segment to cause the distal implant segment to engage a wall of the artery, such that blood flowing through the artery enters the intraluminal implant through the side opening and (i) is diverted from the artery to flow along the proximal implant segment into the vein, and (ii) flows along the distal implant segment to continue through the artery.

19. The method of claim 18, wherein the distal implant segment provides radial support for the artery.

20. The method of claim 18, wherein all blood diverted from the artery is directed along the proximal implant segment and into a superficial vein.

21. The method of claim 18, wherein the proximal implant segment and the distal implant segment comprise tubular bodies.

22. The method of claim 18, wherein blood flowing through the artery enters the side opening and (i) flows through the proximal end of the distal implant segment and a distal end of the distal implant segment to continue through the artery, and (ii) flows through the distal end of the proximal implant segment and out a proximal end of the proximal implant segment to flow into the vein.

23. The method of claim 18, wherein after the proximal implant segment is radially expanded to engage the wall of the vein and the distal implant segment is radially expanded to engage the wall of the artery, the proximal implant segment is angled relative to an axis of the distal implant segment by between about 0 degrees to about 90 degrees.

24. The method of claim 18, wherein the intraluminal implant is delivered into the patient within a sheath constraining the intraluminal implant at a distal end of the sheath, and wherein the distal end of the sheath is advanced into the artery within a cavity of a nose cone.

25. The method of claim 24, wherein the proximal implant segment is released from the sheath to radially expand into engagement with the wall of the vein by proximally retracting the sheath relative to the nose cone, and wherein the distal implant segment is radially expanded into engagement with the wall of the artery by distally advancing the nose cone relative to the distal implant segment.

26. The method of claim 25, further comprising engaging a proximal end of the nose cone with a wall of the artery while the sheath is proximally retracted to release the proximal implant segment.

27. The method of claim 18, wherein the intraluminal implant comprises a continuous ring at the distal end of the proximal implant segment to increase a radial stiffness of the distal end of the proximal implant segment.

28. The method of claim 18, wherein after the proximal implant segment is radially expanded to engage the wall of the vein, the proximal implant segment does not substantially obstruct a lumen of the artery.

29. The method of claim 18, wherein after the distal implant segment is radially expanded to engage the wall of the artery, the distal implant segment, by its connection to the proximal implant segment, prevents the proximal implant segment from obstructing the lumen of the artery.

30. The method of claim 18, wherein the intraluminal implant is delivered, extended, and expanded without radiographic imaging.

* * * * *